(12) United States Patent
Dunetz

(10) Patent No.: US 9,771,328 B2
(45) Date of Patent: Sep. 26, 2017

(54) PROCESSES FOR PREPARING ASK1 INHIBITORS

(71) Applicant: Gilead Sciences, Inc., Foster City, CA (US)

(72) Inventor: Joshua R. Dunetz, Burlingame, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 15/413,154

(22) Filed: Jan. 23, 2017

(65) Prior Publication Data

US 2017/0233350 A1    Aug. 17, 2017

Related U.S. Application Data

(62) Division of application No. 14/757,663, filed on Dec. 22, 2015, now Pat. No. 9,586,933.

(60) Provisional application No. 62/096,391, filed on Dec. 23, 2014, provisional application No. 62/269,064, filed on Dec. 17, 2015.

(51) Int. Cl.
  *C07D 233/64*    (2006.01)

(52) U.S. Cl.
  CPC ........ *C07D 233/64* (2013.01); *C07B 2200/13* (2013.01)

(58) Field of Classification Search
  CPC .................................................... C07D 233/64
  USPC ...................................................... 548/341.5
  See application file for complete search history.

(56) References Cited

U.S. PATENT DOCUMENTS

2011/0009410 A1    1/2011  Corkey et al.
2013/0197037 A1*   8/2013  Notte .................... C07D 213/56
                                                  514/341

OTHER PUBLICATIONS

Intl. Search Report—Written Opinion dated Mar. 11, 2016 for PCT/US2015/067511.

* cited by examiner

*Primary Examiner* — Patricia L Morris
(74) *Attorney, Agent, or Firm* — Briana R. Barron

(57) ABSTRACT

The present disclosure provides processes for the preparation of a compound of formula:

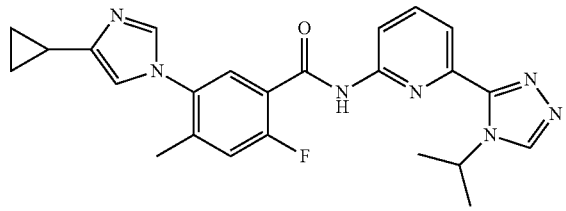

which exhibits apoptosis signal-regulating kinase ("ASK1") inhibitory activity and is thus useful in the treatment of diseases such as kidney disease, diabetic nephropathy and kidney fibrosis. The disclosure also provides compounds that are synthetic intermediates.

5 Claims, 18 Drawing Sheets

PROCESSES FOR PREPARING ASK1 INHIBITORS

CROSS-REFERENCE TO RELATED APPLICATIONS

This application is a divisional of U.S. patent application Ser. No. 14/757,663 filed Dec. 22, 2015, which claims the benefit under 35 U.S.C. 119(e) of U.S. Provisional Patent Application No. 62/096,391 filed Dec. 23, 2014 and U.S. Provisional Patent Application No. 62/269,064 filed Dec. 17, 2015, the entireties of each of which are herein incorporated by reference.

FIELD

The present disclosure relates generally to the field of organic synthetic methodology for the preparation of compounds for the treatment of apoptosis signal-regulating kinase 1 ("ASK1") mediated diseases and the synthetic intermediates prepared thereby.

BACKGROUND

Therapeutic agents that function as inhibitors of ASK1, signaling have the potential to remedy or improve the lives of patients in need of treatment for diseases or conditions such as neurodegenerative, cardiovascular, inflammatory, autoimmune, and metabolic disorders. In particular, ASK1 inhibitors have the potential to treat cardio-renal diseases, including kidney disease, diabetic kidney disease, chronic kidney disease, fibrotic diseases (including lung and kidney fibrosis), respiratory diseases (including pulmonary arterial hypertension (PAH), chronic obstructive pulmonary disease (COPD) and acute lung injury), acute and chronic liver diseases. There is a need for improved or alternate processes to prepare compounds that are potent and exhibit improved pharmacokinetic and/or pharmacodynamic profiles for the treatment of diseases related to ASK1, activation.

SUMMARY 5-(4-Cyclopropyl-1H-imidazol-1-yl)-N-(6-(4-isopropyl-4H-1,2,4-triazol-3-yl)pyridin-2-yl)-2-fluoro-4-methylbenzamide, also known as 5-((4-cyclopropyl-1H-imdazol-1-yl)-2-fluoro-N-(6-(4-isopropyl-4H-1,2,4-triazole-3-yl)pyridine-2-yl)-4-methylbenzamide (Compound of formula (A)), has the formula:

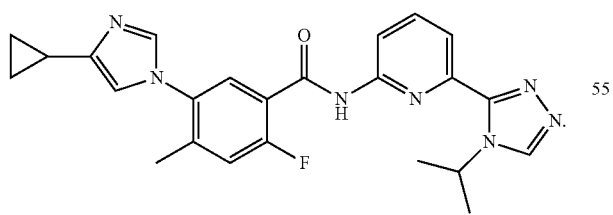

This compound has been shown to exhibit ASK-1 inhibitory activity (U.S. Pat. No. 8,742,126, which is hereby incorporated by reference in its entirety). The present disclosure provides processes for making a compound of formula (A) or a salt or solvate thereof.

In one embodiment, provided is a process for preparing a compound of formula (A), salt thereof, or solvate thereof:

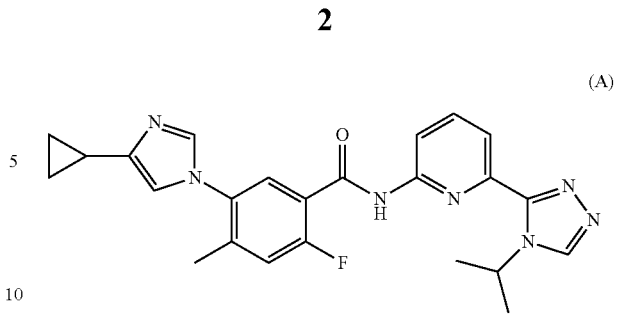

comprising the steps of:
(a) carboxylating a compound of formula (E) or a salt thereof:

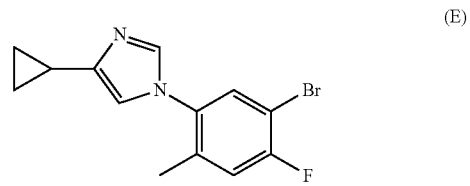

under reaction conditions sufficient to form a compound of formula (D) or a hydrate, solvate or salt thereof:

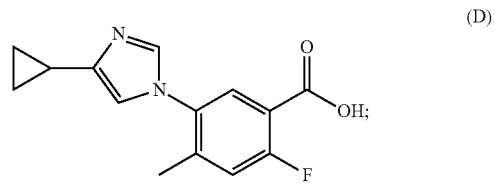 [SMILES: Cc1cc(F)c(C(=O)O)cc1-n1cnc(C2CC2)c1]

(b) chlorinating a compound of formula (D) or a hydrate, solvate or salt thereof under reaction conditions sufficient to form a compound of formula (B) or a salt thereof:

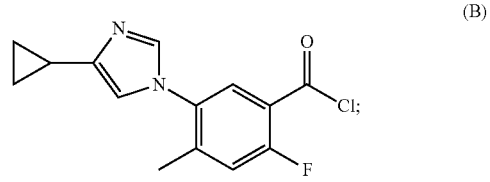 [SMILES: Cc1cc(F)c(C(=O)Cl)cc1-n1cnc(C2CC2)c1]

and
(c) contacting a compound of formula (B) or a salt thereof with a compound of formula (C) or a salt thereof:

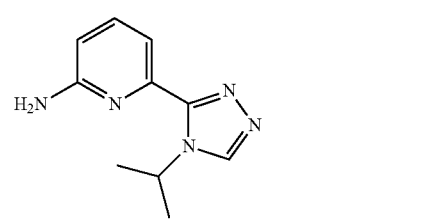

under reaction conditions sufficient to yield a compound of formula (A).

In another embodiment, provided is a process for preparing a compound of formula (A) or salt or solvate thereof:

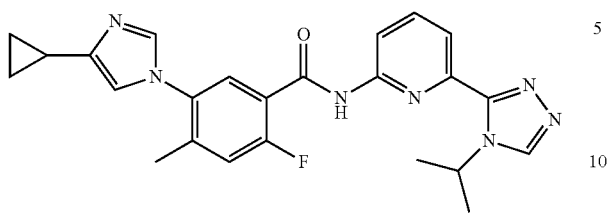
(A)

comprising the steps of:
(a) cyclizing a compound of formula (F):

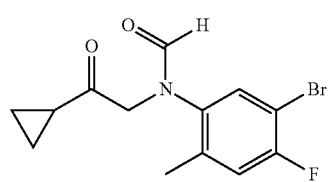
(F)

under reaction conditions sufficient to form a compound of formula (E) or a salt thereof:

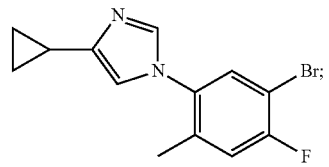
(E)

(b) carboxylating a compound of formula (E) or a salt thereof under reaction conditions sufficient to form a compound of formula (D) or a hydrate, solvate or salt thereof:

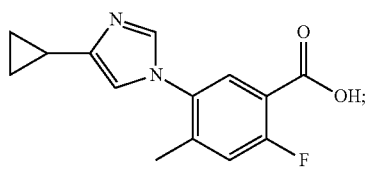
(D)

(c) chlorinating a compound of formula (D) or a hydrate, solvate or salt thereof under reaction conditions sufficient to form a compound of formula (B) or a salt thereof:

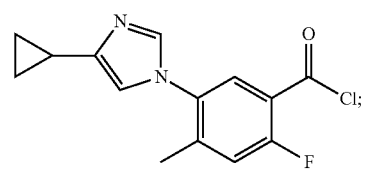
(B)

and
(d) contacting a compound of formula (B) or a salt thereof with a compound of formula (C) or a salt thereof:

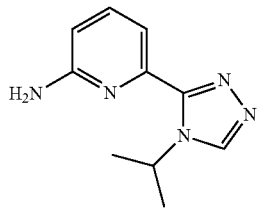
(C)

under reaction conditions sufficient to yield a compound of formula (A).

In another embodiment, provided is a process for preparing a compound of formula (A) or salt or solvate thereof:

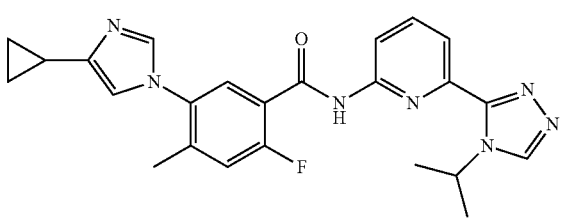
(A)

comprising the steps of:
(a) formylating a compound of formula (G):

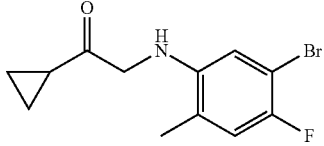
(G)

under reaction conditions sufficient to form a compound of formula (F):

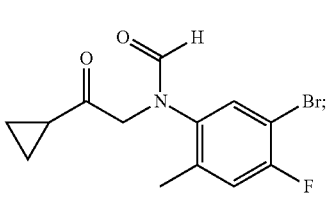
(F)

(b) cyclizing a compound of formula (F) under reaction conditions sufficient to form a compound of formula (E) or a salt thereof:

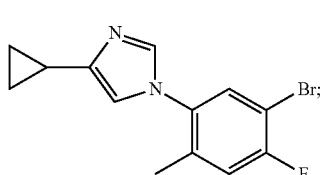
(E)

(c) carboxylating a compound of formula (E) or a salt thereof under reaction conditions sufficient to form a compound of formula (D) or a hydrate, solvate or a salt thereof:

(D)

(d) chlorinating a compound of formula (D) or a hydrate, solvate or a salt thereof under reaction conditions sufficient to form a compound of formula (B) or a salt thereof:

(B)

and (e) contacting a compound of formula (B) or a salt thereof with a compound of formula (C) or a salt thereof:

(C)

under reaction conditions sufficient to yield a compound of formula (A).

In another embodiment, provided is a process for preparing a compound of formula (A) or a salt or solvate thereof:

(A)

(a) contacting a compound of formula (H):

(H)

with a compound of formula (I):

(I)

under reaction conditions sufficient to form a compound of formula (G):

(G)

(b) formylating a compound of formula (G) under reaction conditions sufficient to form a compound of formula (F):

(F)

(c) cyclizing a compound of formula (F) under reaction conditions sufficient to form a compound of formula (E) or a salt thereof:

(E)

(d) carboxylating a compound of formula (E) or a salt thereof under reaction conditions sufficient to form a compound of formula (D) or a hydrate, solvate or salt thereof:

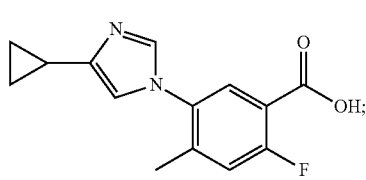

(e) chlorinating a compound of formula (D) or a hydrate, solvate or salt thereof under reaction conditions sufficient to form a compound of formula (B) or a salt thereof:

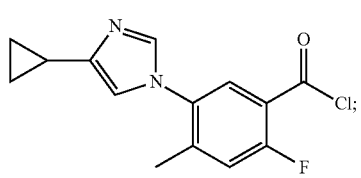

and (f) contacting a compound of formula (B) or a salt thereof with a compound of formula (C) or a salt thereof:

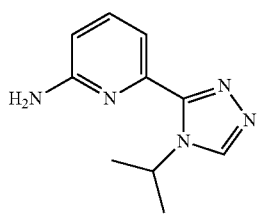

under reaction conditions sufficient to yield a compound of formula (A).

In another embodiment, provided is a process for preparing a compound of formula (A) or a salt or solvate thereof:

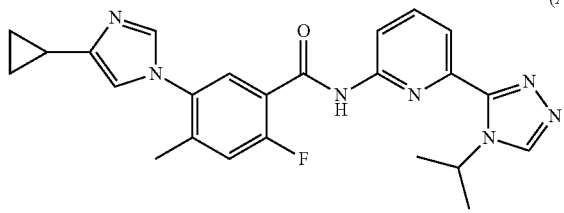

(a) tosyloxylating a compound of formula (J):

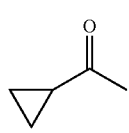

under reaction conditions sufficient to form a compound of formula (H):

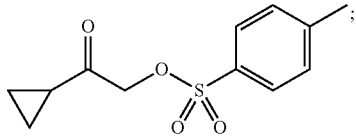

(b) contacting a compound of formula (H) with a compound of formula (I):

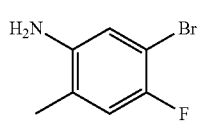

under reaction conditions sufficient to form a compound of formula (G):

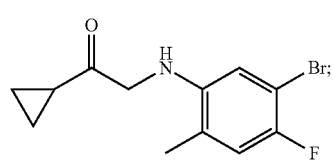

(c) formylating a compound of formula (G) under reaction conditions sufficient to form a compound of formula (F):

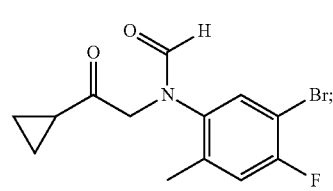

(d) cyclizing a compound of formula (F) under reaction conditions sufficient to form a compound of formula (E) or a salt thereof:

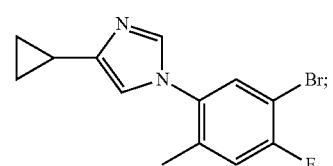

(e) carboxylating a compound of formula (E) or a salt thereof under reaction conditions sufficient to form a compound of formula (D) or a hydrate, solvate or salt thereof:

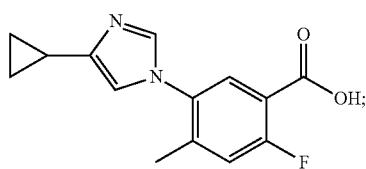
(D)

(f) chlorinating a compound of formula (D) or a hydrate, solvate or salt thereof under reaction conditions sufficient to form a compound of formula (B) or a salt thereof:

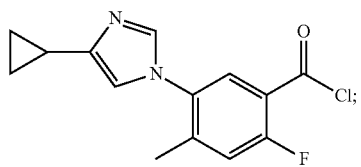
(B)

and
(g) contacting a compound of formula (B) or a salt thereof with a compound of formula (C) or a salt thereof:

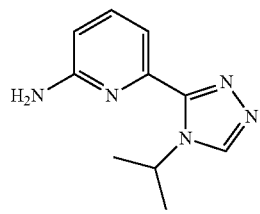
(C)

under reaction conditions sufficient to yield a compound of formula (A).

In another embodiment, provided is a process for preparing a compound of formula (A) or a salt or solvate thereof:

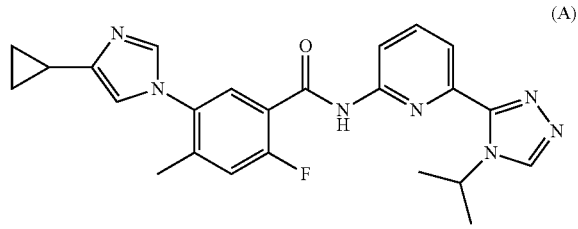
(A)

(a) contacting a compound of formula (K) or a salt thereof:

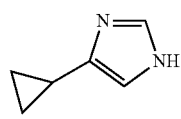
(K)

with a compound of formula (L):

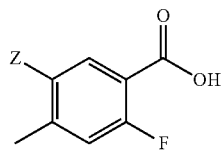
(L)

under reaction conditions sufficient to form a compound of formula (D) or a hydrate, solvate or salt thereof:

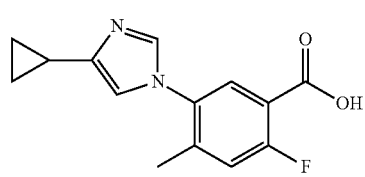
(D)

(b) chlorinating a compound of formula (D) or a hydrate, solvate or salt thereof under reaction conditions sufficient to form a compound of formula (B) or a salt thereof:

(B)

and
(c) contacting a compound of formula (B) or a salt thereof with a compound of formula (C) or a salt thereof:

(C)

under reaction conditions sufficient to yield a compound of formula (A).
wherein Z is a leaving group.

In another embodiment, provided is a process for preparing a compound of formula (D) or a hydrate, solvate or salt thereof:

(D)

comprising the steps of:
(a) carboalkoxylating a compound of formula (E) or a salt thereof:

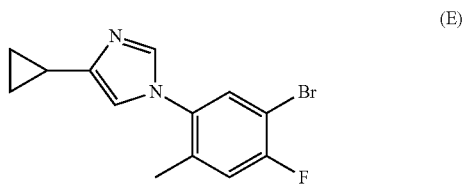 [SMILES: Cc1cc(F)c(Br)cc1-n1cnc(C2CC2)c1]
(E)

under reaction conditions sufficient to form a compound of formula (Q):

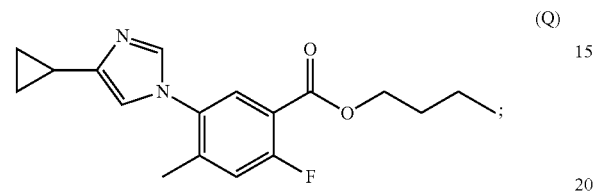
(Q)

and
(b) hydrolyzing a compound of formula (Q) under reaction conditions sufficient to form a compound of formula (D) or a hydrate, solvate or salt thereof.

In another embodiment, provided is a process for preparing a compound of formula (A) or salt or solvate thereof:

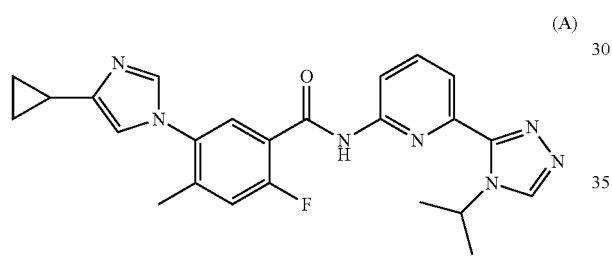
(A)

comprising the steps of:
(a) contacting a compound of formula (E) or a salt thereof:

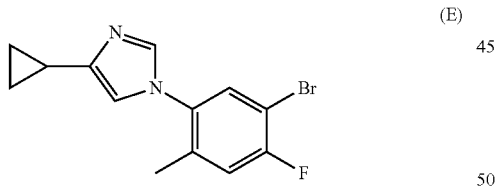
(E)

with a compound of formula (C) or a salt thereof:

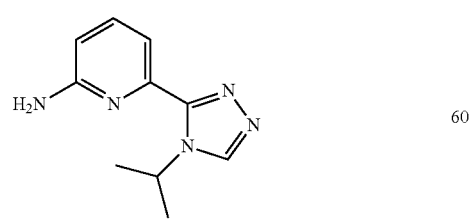
(C)

under reaction conditions sufficient to form a compound of formula (A).

In one embodiment, provided is a process for preparing a compound of formula (A), salt thereof, or solvate thereof:

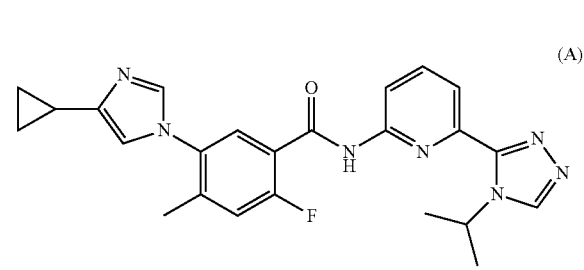
(A)

comprising the steps of:
(a) carboxylating a compound of formula (E) or a salt thereof:

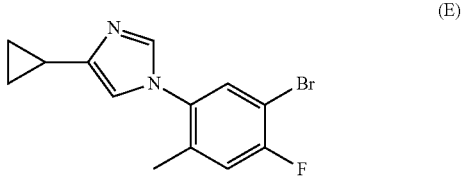 [SMILES: Cc1cc(F)c(Br)cc1-n1cnc(C2CC2)c1]
(E)

under reaction conditions sufficient to form a compound of formula (D) or a hydrate, solvate or salt thereof:

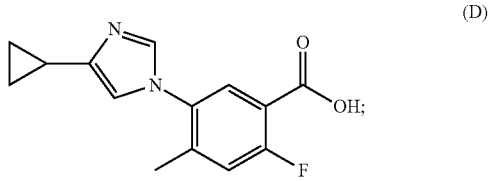 [SMILES: Cc1cc(F)c(C(=O)O)cc1-n1cnc(C2CC2)c1]
(D)

(b) contacting a compound of formula (D) or a hydrate, solvate or salt thereof with propylphosphonic anhydride under reaction conditions sufficient to form a compound of formula (R):

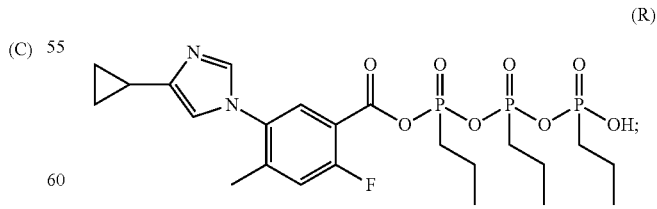
(R)

and
(c) contacting a compound of formula (R) or a salt thereof with a compound of formula (C) or a salt thereof:

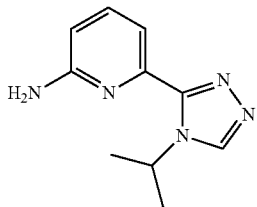

(C)

under reaction conditions sufficient to yield a compound of formula (A).

Another embodiment is crystalline 5-(4-cyclopropyl-1H-imidazol-1-1-2-fluoro-4-methylbenzoic acid hydrochloride (Compound of formula (D-a) Form I) characterized by an X-ray powder diffractogram comprising the following peaks: 7.3, 22.3, 23.4, 23.9, and 26.8° 2θ±0.2° 2θ, as determined on a diffractometer using Cu—Kα radiation at a wavelength of 1.5406 Å.

Another embodiment is crystalline 5-(4-cyclopropyl-1H-imidazol-1-1-2-fluoro-4-methylbenzoic acid hydrochloride (Compound of formula (D-a) Form II) characterized by an X-ray powder diffractogram comprising the following peaks: 8.7, 12.1, 25.7, and 26.3° 2θ±0.2° 2θ, as determined on a diffractometer using Cu—Kα radiation at a wavelength of 1.5406 Å.

Another embodiment is crystalline 5-(4-cyclopropyl-1H-imidazol-1-1-2-fluoro-4-methylbenzoic acid hydrate (Compound of formula (D) hydrate Form I) characterized by an X-ray powder diffractogram comprising the following peaks: 9.5, 20.4, 24.3, 26.5, and 28.7° 2θ±0.2° 2θ, as determined on a diffractometer using Cu—Kα radiation at a wavelength of 1.5406 Å.

Another embodiment is crystalline 5-(4-cyclopropyl-1H-imidazol-1-1-2-fluoro-4-methylbenzoic acid (Compound of formula (D) Form I) characterized by an X-ray powder diffractogram comprising the following peaks: 8.7, 15.2, 21.5, and 23.8° 2θ±0.2° 2θ, as determined on a diffractometer using Cu—Kα radiation at a wavelength of 1.5406 Å.

Another embodiment is crystalline 5-(4-cyclopropyl-1H-imidazol-1-1-2-fluoro-4-methylbenzoic acid (Compound of formula (D) Form II) characterized by a calculated X-ray powder diffractogram comprising the following peaks: 8.4, 13.6, and 15.5° 2θ±0.2° 2θ, as determined on a diffractometer using Cu—Kα radiation at a wavelength of 1.5406 Å.

Another embodiment is crystalline 5-(4-cyclopropyl-1H-imidazol-1-1-2-fluoro-4-methylbenzoic acid (Compound of formula (D) Form III) characterized by an X-ray powder diffractogram comprising the following peaks: 10.3, 17.1, 18.0, and 25.7° 2θ±0.2° 2θ, as determined on a diffractometer using Cu—Kα radiation at a wavelength of 1.5406 Å.

The inventions of this disclosure are described throughout. In addition, specific embodiments of the invention are as disclosed herein.

DETAILED DESCRIPTION

Definitions and General Parameters

Figure 1:
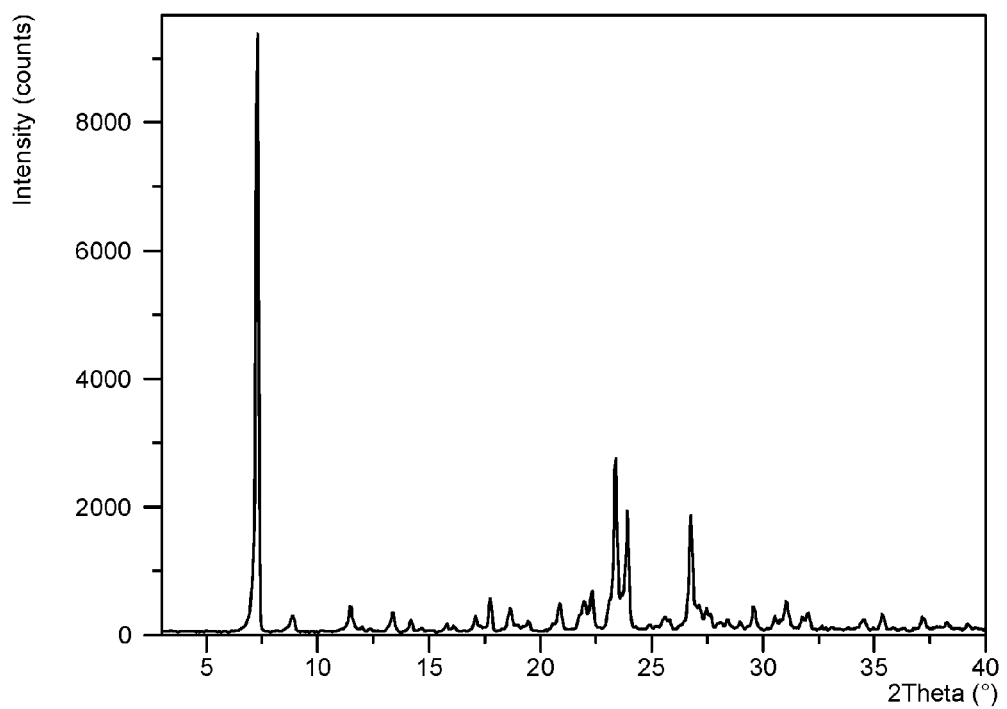
FIG. 1 shows an X-ray powder diffraction (XRPD) of Compound of formula (D-a) Form I.

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "substituted alkylene" refers to an alkylene group as defined above having 1 to 5 substituents (in some embodiments, 1, 2 or 3 substituents) as defined for substituted alkyl.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH=CH$_2$), 1-propylene (or allyl, i.e. —CH$_2$CH=CH$_2$), isopropylene (—C(CH$_3$)=CH$_2$), and the like.

The term "substituted alkenyl" refers to an alkenyl group as defined above having 1 to 5 substituents (in some embodiments, 1, 2 or 3 substituents) as defined for substituted alkyl.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—CCH), propargyl (or propynyl, i.e. —CCCH$_3$), and the like.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group cycloalkyl-O—.

The term "cycloalkenyloxy" refers to the group cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)— heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. In addition, a substituent on the heterocyclic group may be attached to the same carbon atom as, or is geminal to, the attachment of the substituted heterocyclic group to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)— heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "benzyl" refers to the group —CH$_2$—C$_6$H$_5$

The term "amino" refers to the group —NH$_2$.

The term "amine" refers to substituted amino, alkyl amine, dialkylamine, or trialkyl amine groups.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl. The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group —N$^⊕$=N$^⊖$=N.

The term "nitro" refers to a group —NO$_2$.

The term "keto" or "oxo" refers to a group =O.

The term "carboxy" refers to a group —C(O)—OH.

The term "ester" refers to the group —C(O)OR, where R is alkyl, cycloalkyl, aryl, heteroaryl or heterocyclyl, which may be optionally further substituted by alkyl, alkoxy, halogen, $CF_3$, amino, substituted amino, cyano or —$S(O)_nR^a$, in which $R^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "alkoxycarbonylamino" refers to the group —$N(R^d)C(O)OR$ in which R is alkyl and $R^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "aminocarbonylamino" refers to the group —$NR^cC(O)NRR$, wherein $R^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "heterocyclylthio" refers to the group —S-heterocyclyl.

The term "arylthio" refers to the group —S-aryl.

The term "heteroarylthio" refers to the group —S-heteroaryl wherein the heteroaryl group is as defined above including optionally substituted heteroaryl groups as also defined above.

The term "aminosulfonyl" refers to the group —$S(O)_2NRR$, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "hydroxy" or "hydroxyl" refers to the group —OH.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

A "leaving group" includes a molecular fragment that can depart with a pair of electrons from a covalent bond to the reacting carbon atom during a chemical reaction.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given formula is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as "tautomeric isomers" or "tautomers." Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of amide-comprising and imidic acid-comprising tautomers are shown below:

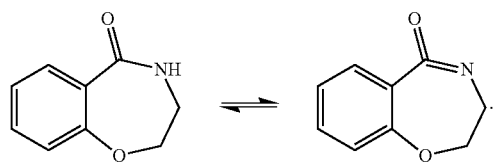

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound and a solvent.

The term "hydrate" refers to the complex formed by the combining of a compound and water.

The term "prodrug" refers to compounds that include chemical groups which, in vivo, can be converted and/or can be split off from the remainder of the molecule to provide for the active drug, a pharmaceutically acceptable salt thereof or a biologically active metabolite thereof.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I when administered to a mammal. See, for example, Foster, "Deuterium Isotope Effects in Studies of Drug Metabolism", Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base "salts" by virtue of the presence of amino and/or carboxyl groups or groups similar thereto. In some cases, the "salt" of a given compound is a pharmaceutically acceptable salt. The term "pharmaceutically acceptable salt" of a given compound refers to salts that retain the biological effectiveness and properties of the given compound, and which are not biologically or otherwise undesirable.

Base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein monosubstituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroayl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to NH(heteroaryl)$_2$, wherein "heteroaryl" is as defined herein and so on. Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. Acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "reaction conditions" is intended to refer to the physical and/or environmental conditions under which a chemical reaction proceeds. The term "under conditions sufficient to" or "under reaction conditions sufficient to" is intended to refer to the reaction conditions under which the desired chemical reaction can proceed. Examples of reaction conditions include, but are not limited to, one or more of following: reaction temperature, solvent, pH, pressure, reaction time, mole ratio of reactants, the presence of a base or acid, or catalyst, radiation, etc. Reaction conditions may be named after the particular chemical reaction in which the conditions are employed, such as, coupling conditions, hydrogenation conditions, acylation conditions, reduction conditions, etc. Reaction conditions for most reactions are generally known to those skilled in the art or can be readily obtained from the literature. Examplary reaction conditions sufficient for performing the chemical transformations provided herein can be found throughout, and in particular, the examples below. It is also contemplated that the reaction conditions can include reagents in addition to those listed in the specific reaction.

The term "reagent" refers to a substance or compound that can be added to bring about a chemical reaction.

The term "chlorinating reagent" refers to a compound that can be added to carry out a chlorination reaction.

The term "ammonium reagent" refers to an ammonium compound, including but not limited to ammonium acetate, ammonium formate, or ammonium hydroxide.

The term "copper reagent" refers to a copper compound, including but not limited to Cu(OAc)$_2$, Cu(OTf)$_2$, Cu$_2$O, and CuBr.

The term "additive" can refer to a compound that can be added to a chemical reaction.

The term "coupling reagent" or "coupling agent" refers to a compound that aids in bringing about a reaction to couple one compound to another compound.

The terms "organolithium reagent" or "organolithium base" refer to an organometallic compound that contains a carbon-lithium bond.

The term "Grignard reagent" refers to a compound having magnesium with an organic radical and a halogen.

The term "ligand" refers to ion or molecule that binds to a central metal atom to form a coordination complex.

The term "organic base" is an organic compound that acts as a base.

The term "organic acid" is an organic compound that acts as an acid.

The term "catalyst" refers to a chemical substance that enables a chemical reaction to proceed at a usually faster rate or under different conditions (such as at a lower temperature) than otherwise possible.

The term "co-catalyst" refers to a chemical substance that improves catalytic activity.

As used herein, the term "about" used in the context of quantitative measurements means the indicated amount ±10%, or alternatively the indicated amount ±5% or ±1%.

In addition, abbreviations as used herein have respective meanings as follows:

| | |
|---|---|
| ° C. | Degree Celsius |
| 2-MeTHF | 2-methyltetrahydrofuran |
| Ac | Acetate |
| Ac$_2$O | Acetic anhydride |
| Ad | 1-adamantyl |
| a-phos | Aromatic amide-derived phosphine |
| aq. | Aqueous |
| ASK 1 | Apoptosis signal-regulating kinase 1 |
| Bu | Butyl |
| CyJohnPhos | (2-Biphenyl)dicyclohexylphosphine |
| d | Doublet |
| dba | dibenzylideneacetone |
| DBU | 1,8-Diazabicyclo[5.4.0]undec-7-ene |
| DCM | Dichloromethane |
| DMAc | N,N-dimethylacetamide |
| DMAP | 4-Dimethylaminopyridine |
| DMF | Dimethylformamide |
| DMF-DPA | Dimethyl formamide di-n-propyl acetal |
| DMSO | Dimethylsulfoxide |
| Dpcb | diphosphinidenecyclobutenes |
| Dppb | 1,4-Bis(diphenylphosphino)butane |
| Dppe | 1,2-Bis(diphenylphosphino)ethane |
| Dppf | 1,1'-Bis(diphenylphosphino)ferrocene |
| Dppp | 1,3-Bis(diphenylphosphino)propane |
| DSC | Differential scanning calorimetry |
| DVS | Dynamic vapor sorption |
| EDC | 1-Ethyl-3-(3-dimethylaminopropyl)carbodiimide |
| Equiv/eq. | Equivalents |
| Et | Ethyl |
| EtOAc | Ethyl acetate |
| g | Gram |
| H or hr(s) | Hour(s) |
| HOBt | Hydroxybenzotriazole |
| HPLC | High-pressure liquid chromatography |
| Hz | Hertz |
| IPA | Isopropanol |
| IPAc/iPrOAc | Isopropyl acetate |
| iPr/i-Pr | Isopropyl |
| J | Coupling constant |
| JohnPhos | (2-Biphenyl)di-tert-butylphosphine |
| KF | Karl Fischer titration |
| Koser's Reagent | Hydroxy(tosyloxy)iodobenzene |
| kV | Kilovolts |
| L | Liter |
| LRMS | Low resolution mass spectrometry |
| m | Multiplet |
| M | Molar |
| mA | Milliamps |
| Me | Methyl |
| Mg or mg | Milligram |
| MHz | Mega hertz |
| min | Minutes |
| mL | Milliliter |
| Mmol or mmol | Millimole |
| MTBE | Methyl-tert-butyl ether |
| NIS | N-iodosuccinimide |
| NMP | N-Methyl-2-pyrrolidone |
| NMR | Nuclear magnetic resonance |
| n-Pr/i-Pr | N-propyl |
| OTf | Triflate |
| PdCl$_2$(AmPhos)$_2$ | Bis(di-tert-butyl(4-dimethylaminophenyl)phosphine)dichloropalladium(II) |
| Ph | Phenyl |
| Pr | Propyl |
| psig | Pound-force per square inch |
| rac-BINAP | (±)-2,2'-Bis(diphenylphosphino)-1,1'-binaphthalene |
| RT | Room temperature |
| S | Singlet |
| Sep | Septet |
| T | Triplet |
| T3P ® | Propylphosphonic Anhydride |
| t-Bu | tert-Butyl |
| TFA | Trifluoroacetic acid |
| TGA | Thermogravimetric analysis |
| THF | Tetrahydrofuran |
| TMEDA | N,N,N',N'-Tetramethylethylenediamine |
| Ts | Tosyl |
| V or vol or vols | Volumes (mL/g) |
| Wt | Weight |
| Xantphos | 4,5-Bis(diphenylphosphino)-9,9-dimethylxanthene |
| XRPD | X-ray powder diffraction |
| Δ | Chemical shift |
| μL | Microliter |

Processes

The present processes may be performed using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula A, B, C, D, D-a, E, F, G, H, I, J, K, L, L-a, L-b, M, N, N-a, O, P, P-a, P-b, Q, R, or other formulas or compounds disclosed herein (e.g. numbered compounds 2-1, 2-2, etc.), may be accomplished as described in the following examples. If available, reagents may be purchased commercially, e.g. from Sigma Aldrich or other chemical suppliers.

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller, C. H., (1975) *J. Chromatogr.,* 113, 3) 283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (Chiral Liquid Chromatography (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

As described generally above, the disclosure provides in some embodiments processes for making a compound of formula (A).

Scheme 1 represents an exemplary synthesis of a compound of formula (A) and can be carried out according to the embodiments described herein. It is contemplated that the exemplary synthesis shown in Scheme 1 may be particularly advantageous. For example, the synthesis employs less toxic starting materials (i.e., using Compound (H) in place of its corresponding analog having bromide at the tosylate position), avoids toxic reagents (i.e., CuCN), and employs less toxic solvents (i.e., using dichloromethane instead of dichloroethane), including at the final step of the synthesis. The synthesis also can utilize milder reaction conditions (i.e., avoids high temperatures needed for cyanation, etc.), can avoid the use of heavy metals, and can require less purification steps (e.g. avoid column chromatography). The particular reaction conditions and reagents employed in Scheme 1 are discussed below.

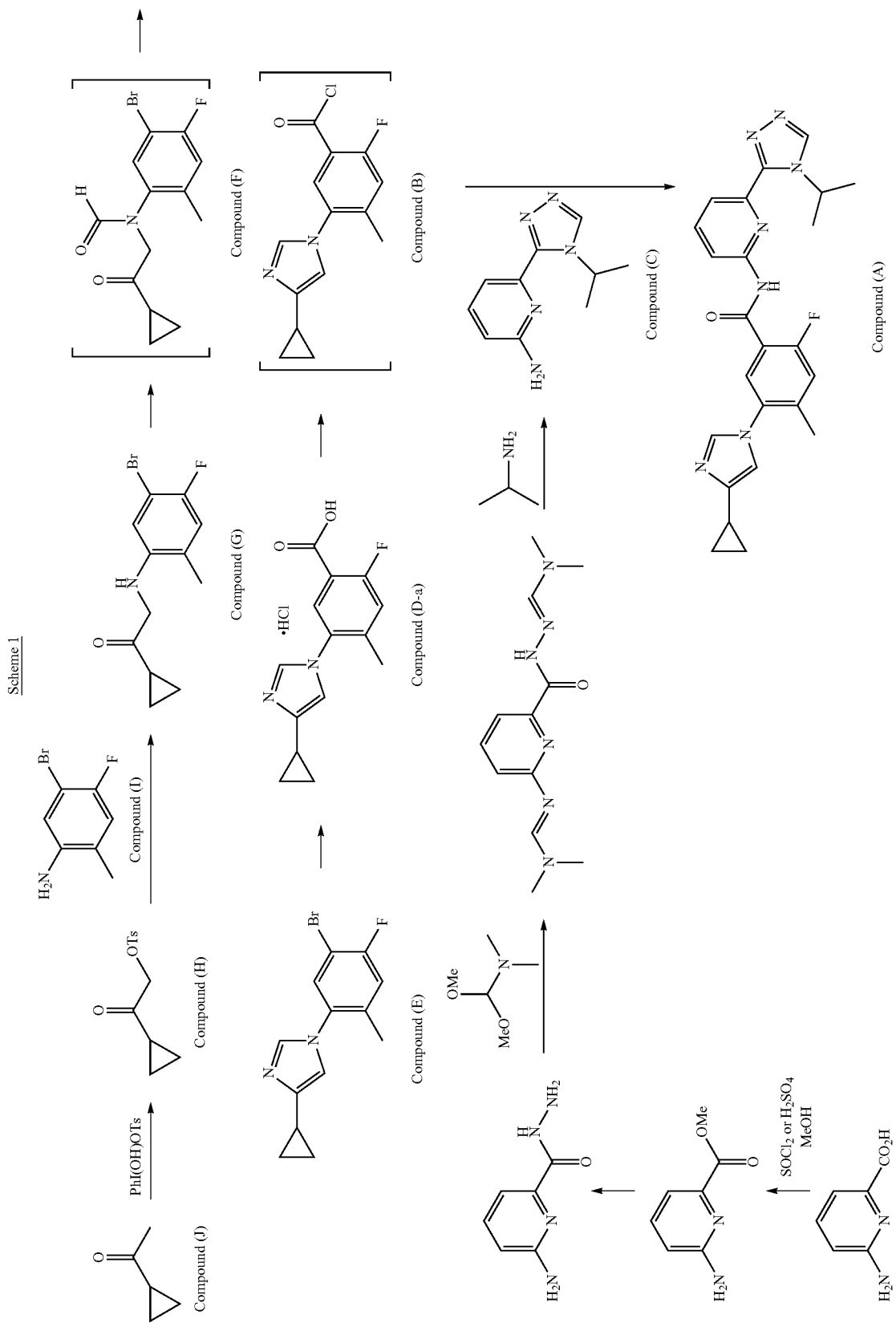

In one embodiment, the present disclosure provides for a process for preparing a compound of formula (A), a salt thereof, or a solvate thereof:

(A)
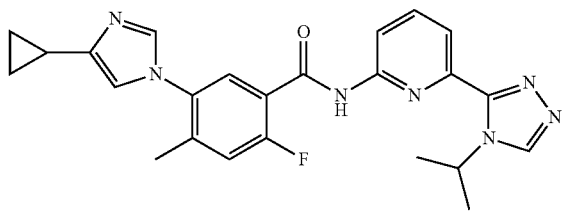

comprising the steps of:
(a) carboxylating a compound of formula (E) or a salt thereof:

(E)
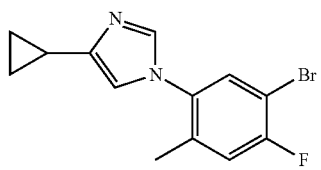

under reaction conditions sufficient to form a compound of formula (D) or a hydrate, solvate, or salt thereof:

(D)
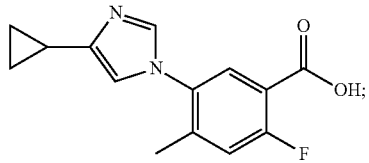

(b) chlorinating a compound of formula (D) or a hydrate, solvate or salt thereof under reaction conditions sufficient to form a compound of formula (B) or a salt thereof:

(B)
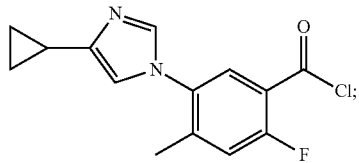

and
(c) contacting a compound of formula (B) or a salt thereof with a compound of formula (C) or a salt thereof:

(C)
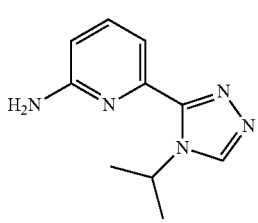

under reaction conditions sufficient to yield a compound of formula (A).

In some embodiments, a compound of formula (E) is a hydrochloride salt. In some embodiments, a compound of formula (B) is a hydrochloride salt. In some embodiments, a compound of formula (D) is a hydrochloride salt. In some embodiments, a compound of formula (D) is a hydrate. In some embodiments, a compound of formula (C) may be a trifluoroacetate salt.

In certain embodiments, the reaction conditions of step (a) comprise a base. In some embodiments, the base may be an organolithium base, such as MeLi, n-BuLi, t-BuLi, and sec-BuLi. In some embodiments, the base may be a Grignard base (e.g., MeMgCl, i-PrMgCl, n-BuMgCl, and PhMgCl). In some embodiments, the base may be isopropyl magnesium chloride.

In some embodiments, the reaction conditions of step (a) comprise a solvent selected from the group consisting of tetrahydrofuran, 2-methyltetrahydrofuran, methyl-tert-butyl ether, and diethyl ether.

In some embodiments, the reaction conditions of step (a) comprise a metallation that occurs at a first temperature and a reaction with $CO_2$ at a second temperature. In some embodiments, the first temperature is about −20° C. to about 40° C., and the second temperature is about −10° C. to about 50° C. In some embodiments, the first temperature is about −5° C. to about 5° C., and the second temperature is about 10° C. to about 20° C.

In certain embodiments, the reaction conditions of step (b) comprise a chlorinating reagent. In some embodiments, the chlorinating reagent may be oxalyl chloride with or without DMF, thionyl chloride, $PCl_5$, or $PCl_3$.

In some embodiments, the reaction conditions of step (b) comprise an additive selected from the group consisting of trimethylsilyl chloride, water, HCl and tetrabutyl ammonium chloride.

In some embodiments, the reaction conditions of step (b) comprise a solvent selected from the group consisting of dichloromethane, acetonitrile, tetrahydrofuran, methyl-tert-butyl ether, and chloroform.

In some embodiments, the reaction conditions of step (b) comprise a temperature of about −20° C. to about 40° C. In some embodiments, the reaction conditions of step (b) comprise a temperature of about 15° C. to about 25° C.

In certain embodiments, the reaction conditions of step (c) comprise an organic base. The organic base may be N,N-diisopropylethylamine, triethylamine, pyridine, and 4-dimethylaminopyridine.

In some embodiments, the reaction conditions of step (c) comprise a solvent selected from the group consisting of dichloromethane, dichloroethane, acetonitrile, tetrahydrofuran, 2-methyltetrahydrofuran toluene, methyl-tert-butyl ether, and chloroform. In some embodiments, the reaction conditions of step (c) comprise a temperature of about 0° C. to about 40° C. In some embodiments, the reaction conditions of step (c) comprise a temperature of about 15° C. to about 25° C.

In one embodiment, the present disclosure provides for a process for preparing a compound of formula (A), a salt thereof, or a solvate thereof:

comprising the steps of:
(a) cyclizing a compound of formula (F):

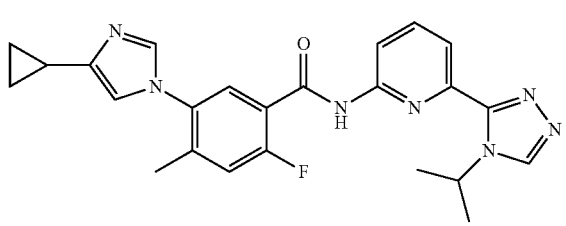
(A)

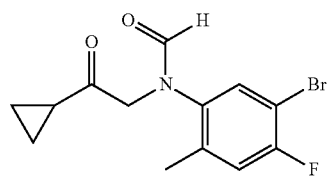
(F)

under reaction conditions sufficient to form a compound of formula (E) or a salt thereof:

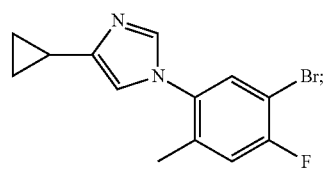
(E)

(b) carboxylating a compound of formula (E) or a salt thereof under reaction conditions sufficient to form a compound of formula (D) or a hydrate, solvate or salt thereof:

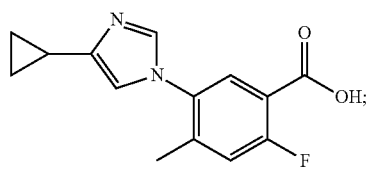
(D)

(c) chlorinating a compound of formula (D) or a hydrate, solvate or salt thereof under reaction conditions sufficient to form a compound of formula (B) or a salt thereof:

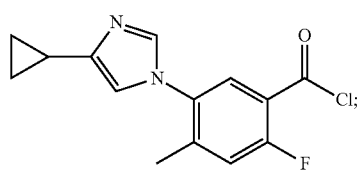
(B)

and
(d) contacting a compound of formula (B) or a salt thereof with a compound of formula (C) or a salt thereof:

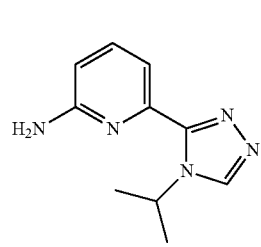
(C)

under reaction conditions sufficient to yield a compound of formula (A).

In some embodiments, a compound of formula (E) is a hydrochloride salt. In some embodiments, a compound of formula (B) is a hydrochloride salt. In some embodiments, a compound of formula (D) is a hydrochloride salt. In some embodiments, a compound of formula (D) is a hydrate. In some embodiments, a compound of formula (C) may be a trifluoroacetate salt.

In certain embodiments, the reaction conditions of step (a) comprise an ammonium reagent. The ammonium reagent may be ammonium acetate, ammonium formate, or ammonium hydroxide. In some embodiments, the reaction conditions of step (a) comprise a solvent selected from the group consisting of acetic acid, toluene, benzene, and isopropanol. In some embodiments, the reaction conditions of step (a) comprise a temperature of about 80° C. to about 120° C. In some embodiments, the reaction conditions of step (a) comprise a temperature of about 110° C. to about 115° C.

In certain embodiments, the reaction conditions of step (b) comprise a base. In some embodiments, the base may be an organolithium base, such as MeLi, n-BuLi, t-BuLi, and sec-BuLi. In some embodiments, the base may be a Grignard base (e.g., MeMgCl, iPrMgCl, n-BuMgCl, and PhMgCl). In some embodiments, the base may be isopropyl magnesium chloride.

In some embodiments, the reaction conditions of step (b) comprise a solvent selected from the group consisting of tetrahydrofuran, 2-methyltetrahydrofuran, methyl-tert-butyl ether, and diethyl ether.

In some embodiments, the reaction conditions of step (b) comprise a metallation that occurs at a first temperature and a reaction with $CO_2$ at a second temperature. In some embodiments, the first temperature is about −20° C. to about 40° C., and the second temperature is about −10° C. to about 50° C. In some embodiments, the first temperature is about −5° C. to about 5° C., and the second temperature is about 10° C. to about 20° C.

In certain embodiments, the reaction conditions of step (c) comprise a chlorinating reagent. In some embodiments, the chlorinating reagent may be oxalyl chloride with or without DMF, thionyl chloride, $PCl_5$, or $PCl_3$.

In some embodiments, the reaction conditions of step (c) comprise an additive selected from the group consisting of trimethylsilyl chloride, water, HCl and tetrabutyl ammonium chloride.

In some embodiments, the reaction conditions of step (c) comprise a solvent selected from the group consisting of dichloromethane, acetonitrile, tetrahydrofuran, methyl-tert-butyl ether, and chloroform.

In some embodiments, the reaction conditions of step (c) comprise a temperature of about −20° C. to about 40° C. In some embodiments, the reaction conditions of step (c) comprise a temperature of about 15° C. to about 25° C.

In certain embodiments, the reaction conditions of step (d) comprise an organic base. The organic base may be N,N-diisopropylethylamine, triethylamine, pyridine, and 4-dimethylaminopyridine.

In some embodiments, the reaction conditions of step (d) comprise a solvent selected from the group consisting of dichloromethane, dichloroethane, acetonitrile, tetrahydrofuran, 2-methyltetrahydrofuran toluene, methyl-tert-butyl ether, and chloroform. In some embodiments, the reaction conditions of step (d) comprise a temperature of about 0° C. to about 40° C. In some embodiments, the reaction conditions of step (d) comprise a temperature of about 15° C. to about 25° C.

In one embodiment, the present disclosure provides a process for preparing a compound of formula (A), a salt thereof, or a solvate thereof:

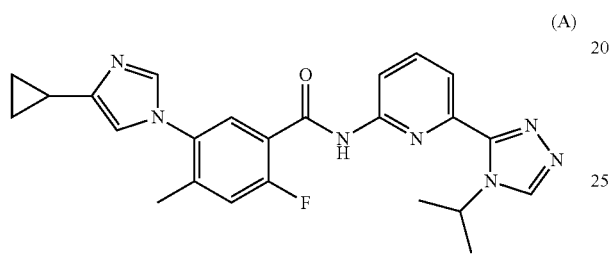

(A)

comprising the steps of:
(a) formylating a compound of formula (G):

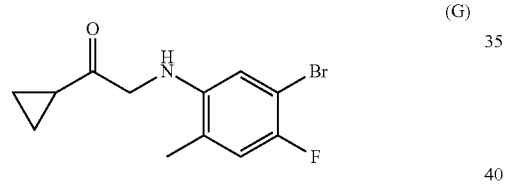

(G)

under reaction conditions sufficient to form a compound of formula (F):

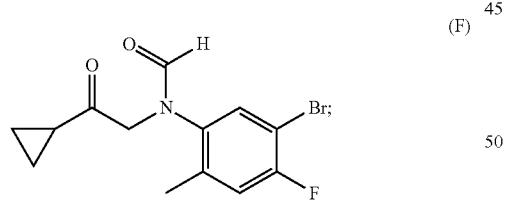

(F)

(b) cyclizing a compound of formula (F) under reaction conditions sufficient to form a compound of formula (E) or a salt thereof:

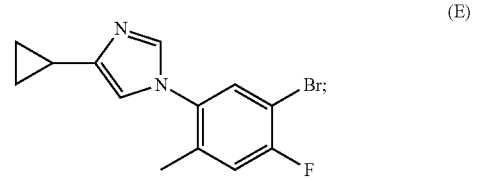 [SMILES: Cc1cc(F)c(Br)cc1-n1cnc(C2CC2)c1]

(E)

(c) carboxylating a compound of formula (E) or a salt thereof under reaction conditions sufficient to form a compound of formula (D) or a hydrate, solvate or salt thereof:

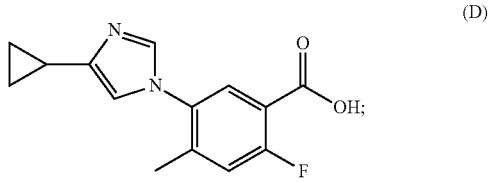 [SMILES: Cc1cc(F)c(C(=O)O)cc1-n1cnc(C2CC2)c1]

(D)

(d) chlorinating a compound of formula (D) or a hydrate, solvate or salt thereof under reaction conditions sufficient to form a compound of formula (B) or a salt thereof:

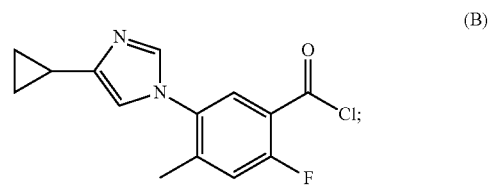 [SMILES: Cc1cc(F)c(C(=O)Cl)cc1-n1cnc(C2CC2)c1]

(B)

and (e) contacting a compound of formula (B) or a salt thereof with a compound of formula (C) or a salt thereof:

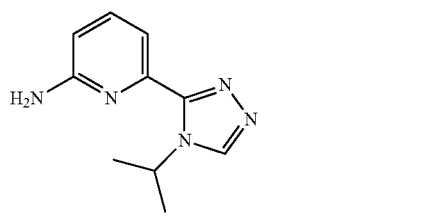

(C)

under reaction conditions sufficient to yield a compound of formula (A).

In some embodiments, a compound of formula (E) is a hydrochloride salt. In some embodiments, a compound of formula (B) is a hydrochloride salt. In some embodiments, a compound of formula (D) is a hydrochloride salt. In some embodiments, a compound of formula (D) is a hydrate. In some embodiments, a compound of formula (C) may be a trifluoroacetate salt.

In certain embodiments, the reaction conditions of step (a) comprise a reagent selected from the group consisting of acetic anhydride and formic acid, acetic acid monoanhydride and carbonic acid, and trifluoroacetic acid anhydride and formic acid.

In some embodiments, the reaction conditions of step (a) comprise a solvent selected from the group consisting of dichloromethane, chloroform, acetonitrile, isopropyl acetate, and tetrahydrofuran. In some embodiments, the reaction conditions of step (a) comprise a temperature of about −10° C. to about 40° C. In some embodiments, the reaction conditions of step (a) comprise a temperature of about 0° C. to about 5° C.

In certain embodiments, the reaction conditions of step (b) comprise an ammonium reagent. The ammonium reagent may be ammonium acetate, ammonium formate, or ammonium hydroxide. In some embodiments, the reaction conditions of step (b) comprise a solvent selected from the group consisting of acetic acid, toluene, benzene, and isopropanol. In some embodiments, the reaction conditions of step (b) comprise a temperature of about 80° C. to about 120° C. In some embodiments, the reaction conditions of step (b) comprise a temperature of about 110° C. to about 115° C.

In certain embodiments, the reaction conditions of step (c) comprise a base. In some embodiments, the base may be an organolithium base, such as MeLi, n-BuLi, t-BuLi, and sec-BuLi. In some embodiments, the base may be a Grignard base (e.g., MeMgCl, iPrMgCl, n-BuMgCl, and PhMgCl). In some embodiments, the base may be isopropyl magnesium chloride.

In some embodiments, the reaction conditions of step (c) comprise a solvent selected from the group consisting of tetrahydrofuran, 2-methyltetrahydrofuran, methyl-tert-butyl ether, and diethyl ether.

In some embodiments, the reaction conditions of step (c) comprise a metallation that occurs at a first temperature and a reaction with $CO_2$ at a second temperature. In some embodiments, the first temperature is about −20° C. to about 40° C., and the second temperature is about −10° C. to about 50° C. In some embodiments, the first temperature is about −5° C. to about 5° C., and the second temperature is about 10° C. to about 20° C.

In certain embodiments, the reaction conditions of step (d) comprise a chlorinating reagent. In some embodiments, the chlorinating reagent may be oxalyl chloride with or without DMF, thionyl chloride, $PCl_5$, or $PCl_3$.

In some embodiments, the reaction conditions of step (d) comprise an additive selected from the group consisting of trimethylsilyl chloride, water, HCl and tetrabutyl ammonium chloride.

In some embodiments, the reaction conditions of step (d) comprise a solvent selected from the group consisting of dichloromethane, acetonitrile, tetrahydrofuran, methyl-tert-butyl ether, and chloroform.

In some embodiments, the reaction conditions of step (d) comprise a temperature of about −20° C. to about 40° C. In some embodiments, the reaction conditions of step (d) comprise a temperature of about 15° C. to about 25° C.

In certain embodiments, the reaction conditions of step (e) comprise an organic base. The organic base may be N,N-diisopropylethylamine, triethylamine, pyridine, and 4-dimethylaminopyridine.

In some embodiments, the reaction conditions of step (e) comprise a solvent selected from the group consisting of dichloromethane, dichloroethane, acetonitrile, tetrahydrofuran, 2-methyltetrahydrofuran toluene, methyl-tert-butyl ether, and chloroform. In some embodiments, the reaction conditions of step (e) comprise a temperature of about 0° C. to about 40° C. In some embodiments, the reaction conditions of step (e) comprise a temperature of about 15° C. to about 25° C.

In one embodiment, the present disclosure provides for a process for preparing a compound of formula (A), a salt thereof, or a solvate thereof:

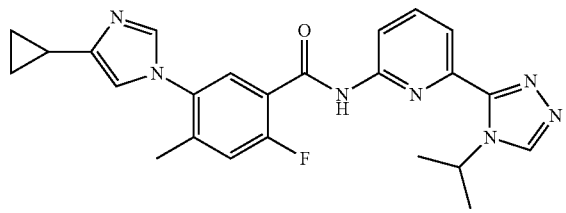

(A)

comprising the steps of:

(a) contacting a compound of formula (H):

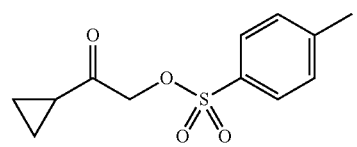

(H)

with a compound of formula (I):

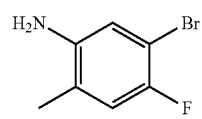

(I)

under reaction conditions sufficient to form a compound of formula (G):

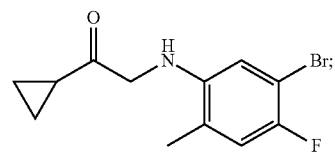

(G)

(b) formylating a compound of formula (G) under reaction conditions sufficient to form a compound of formula (F):

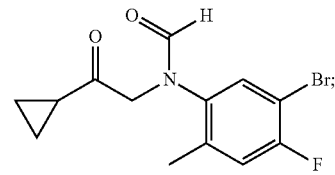

(F)

(c) cyclizing a compound of formula (F) under reaction conditions sufficient to form a compound of formula (E) or a salt thereof:

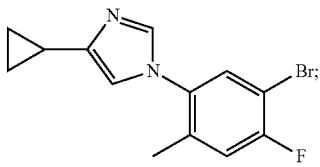

(E)

(d) carboxylating a compound of formula (E) or a salt thereof under reaction conditions sufficient to form a compound of formula (D) or a hydrate, solvate or salt thereof:

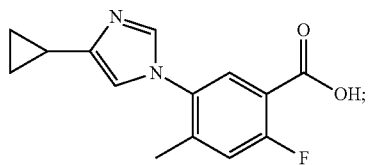

(D)

(e) chlorinating a compound of formula (D) or a hydrate, solvate or salt thereof under reaction conditions sufficient to form a compound of formula (B) or a salt thereof:

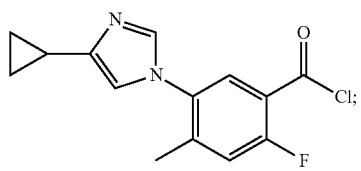

(B)

and (f) contacting a compound of formula (B) or a salt thereof with a compound of formula (C) or a salt thereof

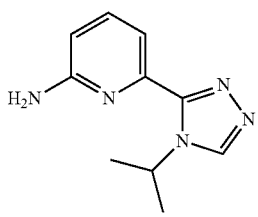

(C)

under reaction conditions sufficient to yield a compound of formula (A).

In some embodiments, a compound of formula (E) is a hydrochloride salt. In some embodiments, a compound of formula (B) is a hydrochloride salt. In some embodiments, a compound of formula (D) is a hydrochloride salt. In some embodiments, a compound of formula (D) is a hydrate. In some embodiments, a compound of formula (C) may be a trifluoroacetate salt.

In certain embodiments, the reaction conditions of step (a) comprise a base. The base may be an organic base (e.g., N,N-diisopropylethylamine, DBU and DMAP), an alkali metal base (e.g., NaH), a hexamethyldisilazane base (e.g., sodium, potassium and lithium hexamethyldisilazide), a carbonate base (e.g., $Cs_2CO_3$, $Na_2CO_3$), or a tert-butoxide (e.g., lithium tert-butoxide, sodium tert-butoxide, potassium tert-butoxide, or magnesium di-tert-butoxide). In some embodiments, the base may be N,N-diisopropylethylamine.

In some embodiments, the reaction conditions of step (a) the reaction conditions of step (a) comprise a solvent selected from the group consisting of toluene, tetrahydrofuran, 2-methyltetrahydrofuran, methyl-tert-butyl ether, acetonitrile, dioxane, benzene, dimethylformamide, dimethylacetamide, and N-methyl-2-pyrrolidone. In some embodiments, the reaction conditions of step (a) comprise a temperature of about −78° C. to about 100° C. In some embodiments, the reaction conditions of step (a) comprise a temperature of about 90° C. to about 100° C.

In certain embodiments, the reaction conditions of step (b) comprise a reagent selected from the group consisting of acetic anhydride and formic acid, acetic acid anhydride and carbonic acid, and trifluoroacetic acid anhydride and formic acid.

In some embodiments, the reaction conditions of step (b) comprise a solvent selected from the group consisting of dichloromethane, chloroform, acetonitrile, isopropyl acetate, and tetrahydrofuran. In some embodiments, the reaction conditions of step (b) comprise a temperature of about −10° C. to about 40° C. In some embodiments, the reaction conditions of step (b) comprise a temperature of about 0° C. to about 5° C.

In certain embodiments, the reaction conditions of step (c) comprise an ammonium reagent. The ammonium reagent may be ammonium acetate, ammonium formate, or ammonium hydroxide. In some embodiments, the reaction conditions of step (c) comprise a solvent selected from the group consisting of acetic acid, toluene, benzene, and isopropanol. In some embodiments, the reaction conditions of step (c) comprise a temperature of about 80° C. to about 120° C. In some embodiments, the reaction conditions of step (c) comprise a temperature of about 110° C. to about 115° C.

In certain embodiments, the reaction conditions of step (d) comprise a base. In some embodiments, the base may be an organolithium base, such as MeLi, n-BuLi, t-BuLi, and sec-BuLi. In some embodiments, the base may be a Grignard base (e.g., MeMgCl, i-PrMgCl, n-BuMgCl, and PhMgCl). In some embodiments, the base may be isopropyl magnesium chloride.

In some embodiments, the reaction conditions of step (d) comprise a solvent selected from the group consisting of tetrahydrofuran, 2-methyltetrahydrofuran, methyl-tert-butyl ether, and diethyl ether.

In some embodiments, the reaction conditions of step (d) comprise a metallation that occurs at a first temperature and a reaction with $CO_2$ at a second temperature. In some embodiments, the first temperature is about −20° C. to about 40° C., and the second temperature is about −10° C. to about 50° C. In some embodiments, the first temperature is about −5° C. to about 5° C., and the second temperature is about 10° C. to about 20° C.

In certain embodiments, the reaction conditions of step (e) comprise a chlorinating reagent. In some embodiments, the chlorinating reagent may be oxalyl chloride with or without DMF, thionyl chloride, $PCl_5$, or $PCl_3$.

In some embodiments, the reaction conditions of step (e) comprise an additive selected from the group consisting of trimethylsilyl chloride, water, HCl and tetrabutyl ammonium chloride.

In some embodiments, the reaction conditions of step (e) comprise a solvent selected from the group consisting of dichloromethane, acetonitrile, tetrahydrofuran, methyl-tert-butyl ether, and chloroform.

In some embodiments, the reaction conditions of step (e) comprise a temperature of about −20° C. to about 40° C. In some embodiments, the reaction conditions of step (e) comprise a temperature of about 15° C. to about 25° C.

In certain embodiments, the reaction conditions of step (f) comprise an organic base. The organic base may be N,N-diisopropylethylamine, triethylamine, pyridine, and 4-dimethylaminopyridine.

In some embodiments, the reaction conditions of step (f) comprise a solvent selected from the group consisting of dichloromethane, dichloroethane, acetonitrile, tetrahydrofuran, 2-methyltetrahydrofuran toluene, methyl-tert-butyl ether, and chloroform. In some embodiments, the reaction conditions of step (f) comprise a temperature of about 0° C. to about 40° C. In some embodiments, the reaction conditions of step (f) comprise a temperature of about 15° C. to about 25° C.

In one embodiment, the present disclosure provides for a process for preparing a compound of formula (A), a salt thereof, or a solvate thereof:

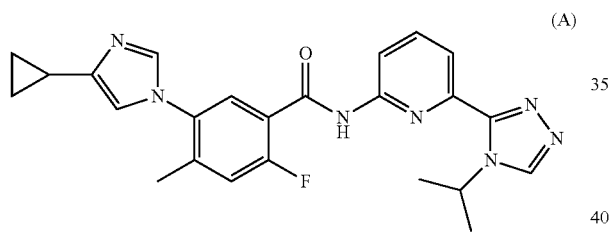
(A)

comprising the steps of:
(a) tosyloxylating a compound of formula (J):

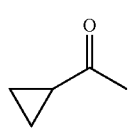
(J)

under reaction conditions sufficient to form a compound of formula (H):

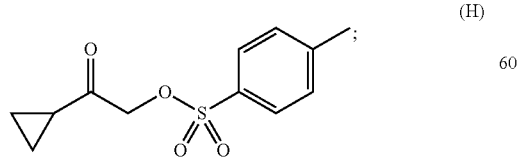
(H)

(b) contacting a compound of formula (H) with a compound of formula (I):

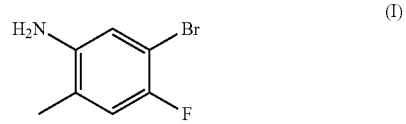
(I)

under reaction conditions sufficient to form a compound of formula (G):

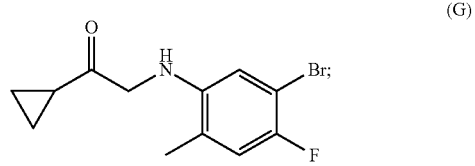 [SMILES: Cc1cc(F)c(Br)cc1NCC(=O)C1CC1]
(G)

(c) formylating a compound of formula (G) under reaction conditions sufficient to form a compound of formula (F):

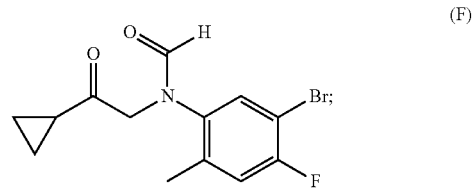 [SMILES: Cc1cc(F)c(Br)cc1N(C=O)CC(=O)C1CC1]
(F)

(d) cyclizing a compound of formula (F) under reaction conditions sufficient to form a compound of formula (E) or a salt thereof:

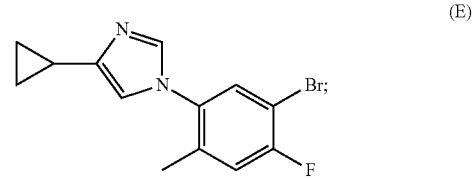 [SMILES: Cc1cc(F)c(Br)cc1-n1cnc(C2CC2)c1]
(E)

(e) carboxylating a compound of formula (E) or a salt thereof under reaction conditions sufficient to form a compound of formula (D) or a hydrate, solvate or salt thereof:

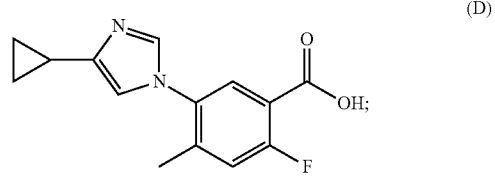 [SMILES: Cc1cc(F)c(C(=O)O)cc1-n1cnc(C2CC2)c1]
(D)

(f) chlorinating a compound of formula (D) or a hydrate, solvate or salt thereof under reaction conditions sufficient to form a compound of formula (B) or a salt thereof:

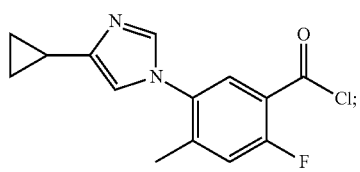

(B)

and (g) contacting a compound of formula (B) or a salt thereof with a compound of formula (C) or a salt thereof:

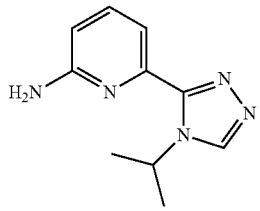

(C)

under reaction conditions sufficient to yield a compound of formula (A).

In some embodiments, a compound of formula (E) is a hydrochloride salt. In some embodiments, a compound of formula (B) is a hydrochloride salt. In some embodiments, a compound of formula (D) is a hydrochloride salt. In some embodiments, a compound of formula (D) is a hydrate. In some embodiments, a compound of formula (C) may be a trifluoroacetate salt.

In certain embodiments, the reaction conditions of step (a) comprise adding Koser's reagent. In some embodiments, the reaction conditions of step (a) comprise a reagent selected from the group consisting of (diacetoxyiodo)benzene organosulfonic acid, (diacetoxyiodo)benzene and p-toluenesulfonic acid, iodosylbenzene/p-toluenesulfonic acid, m-chloroperbenzoic acid/p-toluenesulfonic acid, poly(4-hydroxy tosyloxyiodo)styrenes, N-methyl-O-tosylhydroxylamine, Dess-Martin periodinane/p-toluenesulfonic acid, $HIO_3$/p-toluenesulfonic acid, and o-iodoxybenzoic acid/p-toluenesulfonic acid.

In some embodiments, the reaction conditions of step (a) comprise a solvent selected from the group consisting of acetonitrile, toluene, benzene, tetrahydrofuran, 2-methyltetrahydrofuran, dichloromethane, and chloroform. In some embodiments, the reaction conditions of step (a) comprise a temperature of about 20° C. to about 100° C. In some embodiments, the reaction conditions of step (a) comprise a temperature of about 75° C. to about 80° C.

In certain embodiments, the reaction conditions of step (b) comprise a base. The base may be an organic base (e.g., N,N-diisopropylethylamine, DBU and DMAP), an alkali metal base (e.g., NaH), a hexamethyldisilazane base (e.g., sodium, potassium and lithium hexamethyldisilazide), a carbonate base (e.g., $Cs_2CO_3$, $Na_2CO_3$), and potassium tert-butoxide. In some embodiments, the base may be N,N-diisopropylethylamine.

In some embodiments, the reaction conditions of step (b) the reaction conditions of step (b) comprise a solvent selected from the group consisting of toluene, tetrahydrofuran, 2-methyltetrahydrofuran, methyl-tert-butyl ether, acetonitrile, dioxane, benzene, dimethylformamide, dimethylacetamide, and N-methyl-2-pyrrolidone. In some embodiments, the reaction conditions of step (b) comprise a temperature of about −78° C. to about 100° C. In some embodiments, the reaction conditions of step (b) comprise a temperature of about 90° C. to about 100° C.

In certain embodiments, the reaction conditions of step (c) comprise a reagent selected from the group consisting of acetic anhydride and formic acid, acetic acid monoanhydride and carbonic acid, and trifluoroacetic acid anhydride and formic acid.

In some embodiments, the reaction conditions of step (c) comprise a solvent selected from the group consisting of dichloromethane, chloroform, acetonitrile, isopropyl acetate, and tetrahydrofuran. In some embodiments, the reaction conditions of step (c) comprise a temperature of about −10° C. to about 40° C. In some embodiments, the reaction conditions of step (c) comprise a temperature of about 0° C. to about 5° C.

In certain embodiments, the reaction conditions of step (d) comprise an ammonium reagent. The ammonium reagent may be ammonium acetate, ammonium formate, or ammonium hydroxide. In some embodiments, the reaction conditions of step (d) comprise a solvent selected from the group consisting of acetic acid, toluene, benzene, and isopropanol. In some embodiments, the reaction conditions of step (d) comprise a temperature of about 80° C. to about 120° C. In some embodiments, the reaction conditions of step (d) comprise a temperature of about 110° C. to about 115° C.

In certain embodiments, the reaction conditions of step (e) comprise a base. In some embodiments, the base may be an organolithium base, such as MeLi, n-BuLi, t-BuLi, and sec-BuLi. In some embodiments, the base may be a Grignard base (e.g., MeMgCl, i-PrMgCl, n-BuMgCl, and PhMgCl). In some embodiments, the base may be isopropyl magnesium chloride.

In some embodiments, the reaction conditions of step (e) comprise a solvent selected from the group consisting of tetrahydrofuran, 2-methyltetrahydrofuran, methyl-tert-butyl ether, and diethyl ether.

In some embodiments, the reaction conditions of step (e) comprise a metallation that occurs at a first temperature and a reaction with $CO_2$ at a second temperature. In some embodiments, the first temperature is about −20° C. to about 40° C., and the second temperature is about −10° C. to about 50° C. In some embodiments, the first temperature is about −5° C. to about 5° C., and the second temperature is about 10° C. to about 20° C.

In certain embodiments, the reaction conditions of step (f) comprise a chlorinating reagent. In some embodiments, the chlorinating reagent may be oxalyl chloride with or without DMF, thionyl chloride, $PCl_5$, or $PCl_3$.

In some embodiments, the reaction conditions of step (f) comprise an additive selected from the group consisting of trimethylsilyl chloride, water, HCl and tetrabutyl ammonium chloride.

In some embodiments, the reaction conditions of step (f) comprise a solvent selected from the group consisting of dichloromethane, acetonitrile, tetrahydrofuran, methyl-tert-butyl ether, and chloroform.

In some embodiments, the reaction conditions of step (f) comprise a temperature of about −20° C. to about 40° C. In some embodiments, the reaction conditions of step (f) comprise a temperature of about 15° C. to about 25° C.

In certain embodiments, the reaction conditions of step (g) comprise an organic base. The organic base may be N,N-diisopropylethylamine, triethylamine, pyridine, and 4-dimethylaminopyridine.

In some embodiments, the reaction conditions of step (g) comprise a solvent selected from the group consisting of dichloromethane, dichloroethane, acetonitrile, tetrahydrofuran, 2-methyltetrahydrofuran, toluene, methyl-tert-butyl ether, and chloroform. In some embodiments, the reaction conditions of step (g) comprise a temperature of about 0° C. to about 40° C. In some embodiments, the reaction conditions of step (g) comprise a temperature of about 15° C. to about 25° C.

In one embodiment, provided is a process for preparing a compound of formula (A), salt thereof, or solvate thereof:

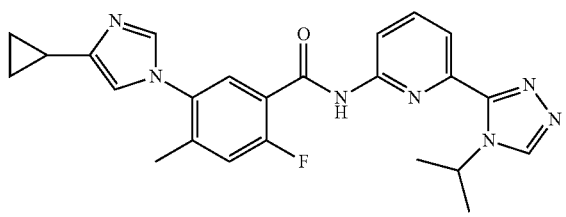
(A)

comprising the steps of:
(a) carboxylating a compound of formula (E) or a salt thereof:

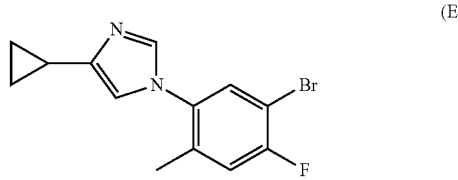
(E)

under reaction conditions sufficient to form a compound of formula (D) or a hydrate, solvate or salt thereof:

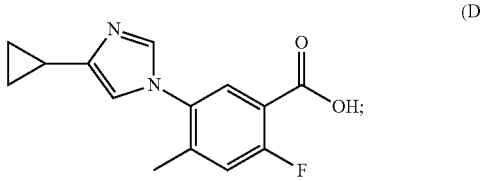 [SMILES: Cc1cc(F)c(C(=O)Cl)cc1-n1cnc(C2CC2)c1]
(D)

(b) contacting a compound of formula (D) or a hydrate, solvate or salt thereof with propylphosphonic anhydride under reaction conditions sufficient to form a compound of formula (R):

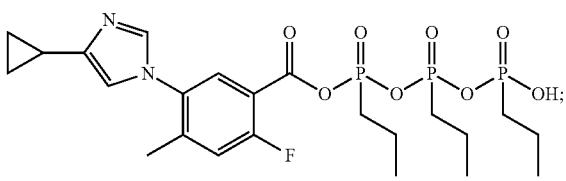
(R)

and
(c) contacting a compound of formula (R) or a salt thereof with a compound of formula (C) or a salt thereof:

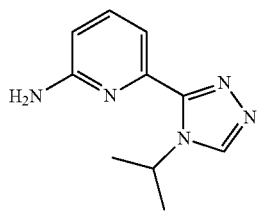
(C)

under reaction conditions sufficient to yield a compound of formula (A).

In some embodiments, a compound of formula (E) is a hydrochloride salt. In some embodiments, a compound of formula (D) is a hydrochloride salt. In some embodiments, a compound of formula (D) is a hydrate.

In some embodiments, a compound of formula (E) is synthesized according to any of the relevant methods described herein.

In certain embodiments, the reaction conditions of step (a) comprise a base. In some embodiments, the base may be an organolithium base, such as MeLi, n-BuLi, t-BuLi, and sec-BuLi. In some embodiments, the base may be a Grignard base (e.g., MeMgCl, i-PrMgCl, n-BuMgCl, and PhMgCl). In some embodiments, the base may be isopropyl magnesium chloride.

In some embodiments, the reaction conditions of step (a) comprise a solvent selected from the group consisting of tetrahydrofuran, 2-methyltetrahydrofuran, methyl-tert-butyl ether, and diethyl ether.

In some embodiments, the reaction conditions of step (a) comprise a metallation that occurs at a first temperature and a reaction with $CO_2$ at a second temperature. In some embodiments, the first temperature is about −20° C. to about 40° C., and the second temperature is about −10° C. to about 50° C. In some embodiments, the first temperature is about −5° C. to about 5° C., and the second temperature is about 10° C. to about 20° C.

In certain embodiments, the reaction conditions of step (b) comprise a solvent selected from the group consisting of dichloromethane, tetrahydrofuran, dimethylformamide, ethyl acetate, methyl-tert-butyl ether, toluene, N-methyl-2-pyrrolidone, N,N-dimethyl acetamide, acetonitrile, dichloroethane, 2-methyltetrahydrofuran, and cyclopentyl methyl ether. In some embodiments, the reaction conditions of step (b) comprise a temperature of about −10° C. to about 60° C. In some embodiments, the reaction conditions of step (b) comprise a temperature of about 0° C. to about 30° C. In some embodiments, the reaction conditions of step (b) comprise a temperature of about 20° C.

In certain embodiments, the reaction conditions of step (b) comprise at least one organic base. The organic base may be organic amine, including but not limited to diisopropylethylamine, 4-dimethylaminopyridine, triethylamine, and N-methyl morpholine, and combinations thereof. In some embodiments, the base may be a carbonate salt, including but not limited to lithium carbonates, sodium carbonates, and cesium carbonates.

Scheme 2 represents an exemplary synthesis of a compound of formula (A) and can be carried out according to the embodiments described herein. It is contemplated that this exemplary synthesis can provide a more time-effective and convergent method for preparing Compound (D). It is also contemplated that this synthesis exhibits the additional advantages of utilizing hydrazide earlier in the synthetic route and employing less toxic starting materials (i.e., using Compound (H) in place of its corresponding analog having bromide at the tosylate position). The particular reaction conditions and reagents employed in Scheme 2 are discussed below.

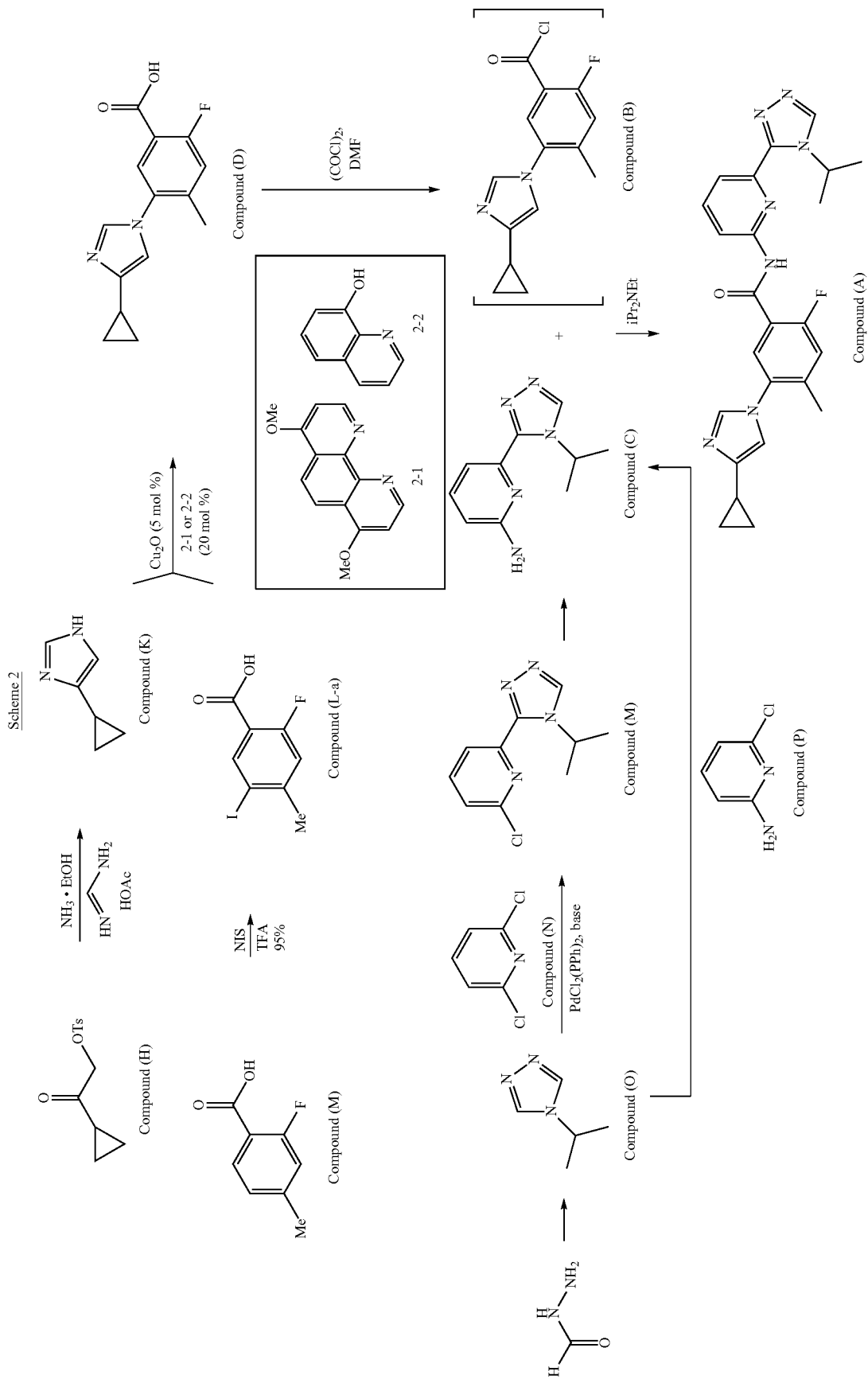

In one embodiment, the present disclosure provides for a process for preparing a compound of formula (A), a salt thereof, or a solvate thereof:

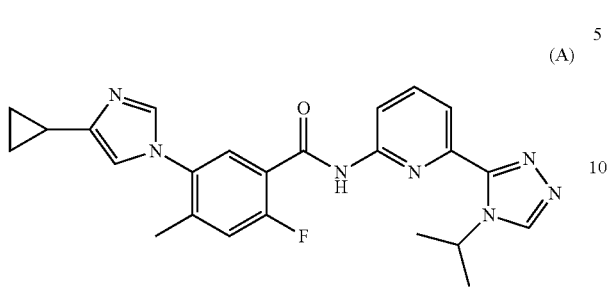

(A)

comprising the steps of:
(a) contacting a compound of formula (K) or a salt thereof:

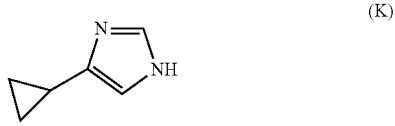

(K)

with a compound of formula (L):

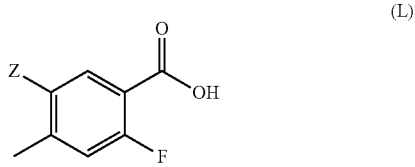

(L)

under reaction conditions sufficient to form a compound of formula (D) or a hydrate, solvate or salt thereof:

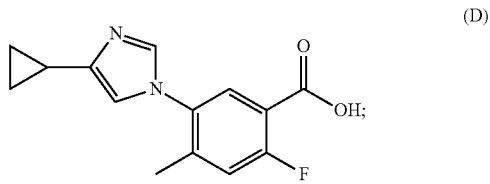 [SMILES: Cc1cc(F)c(C(=O)O)cc1-n1cnc(C2CC2)c1]

(D)

(b) chlorinating a compound of formula (D) or a hydrate, solvate or salt thereof under reaction conditions sufficient to form a compound of formula (B) or a salt thereof:

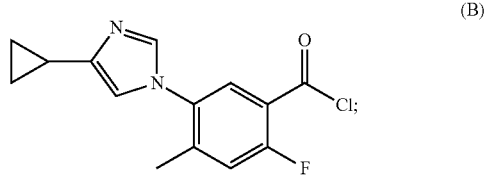 [SMILES: Cc1cc(F)c(C(=O)Cl)cc1-n1cnc(C2CC2)c1]

(B)

and
(c) contacting a compound of formula (B) or a salt thereof with a compound of formula (C) or a salt thereof:

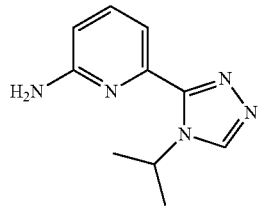

(C)

under reaction conditions sufficient to yield a compound of formula (A).
wherein Z is a leaving group.

In some embodiments, the salt of compound (K) may be a besylate salt. In some embodiments, the salt of compound (B) may be a hydrochloride salt. In some embodiments, the salt of compound (D) may be a hydrochloride salt.

In some embodiments, Z may be a halogen, triflate, tosylate, boronate ester, or boronic acid. In some embodiments, the boronate ester may be allylboronic acid pinacol ester. In some embodiments, Z may be —Cl, —Br, or —I. In some embodiments, Z may be a boronic acid.

In some embodiments, such as when Z may be a halogen, triflate, or tosylate, the reaction conditions of step (a) comprise a base. The base may be a carbonate base (such as $Cs_2CO_3$, $K_2CO_3$ and $Na_2CO_3$) or a phosphate base (such as $K_3PO_4$ or $Na_3PO_4$). In such embodiments, the reaction conditions of step (a) comprise a catalyst. The catalyst may be $Cu_2O$, CuOAc, CuI, CuBr, and [(CuOTf)$_2$-benzene complex]. In such embodiments, a ligand may be included, such as 8-hydroxyquinoline, phenanthroline ligands (such as 4,7-dimethoxy-1,10-phenanthroline and 1,10-phenanthroline), aminoarenethiols (such as 2-((dimethylamino)methyl)benzenethiol), oxime-phospine oxides, phosphoramidites, 2-aminopyrimidine diols (such as 2-aminopyrimidine-4, 6-diol), and oxime-phosphine oxides (such as 2-hydroxybenzaldehyde oxime). Additives may also be included, such as polyethyleneglycol and/or water, $Et_4NHCO_3$ and cetryltrimethylammonium bromide.

In some embodiments, such as when Z may be a halogen, triflate, or tosylate, the reaction conditions of step (a) comprise a solvent selected from the group consisting of N-methyl-2-pyrrolidone, dimethylformamide, N,N-dimethylacetamide, dimethylsulfoxide, butyronitrile, xylenes, propionitrile, dioxane, and toluene. In such embodiments, the reaction conditions of step (a) comprise a temperature of about 80° C. to about 150° C. In some embodiments, the reaction conditions of step (a) comprise a temperature of about 90° C. to about 100° C.

In some embodiments, such as when Z may be a boronate ester or boronic acid, the reaction conditions of step (a) comprise a copper reagent and base. The copper reagent may be $Cu(OAc)_2$, $Cu(OTf)_2$, $Cu_2O$, and CuBr. The base may be triethylamine, pyridine, or N,N-diisopropylethylamine. In some embodiments, the reaction conditions of step (a) comprise a solvent selected from the group consisting of methanol, dichloromethane, and dimethylformamide. In some embodiments, the reaction conditions of step (a) comprise a temperature of about 23° C. to about 100° C. In some embodiments, the reaction conditions of step (a) comprise a temperature of about 23° C.

In certain embodiments, the reaction conditions of step (b) comprise a chlorinating reagent. In some embodiments, the chlorinating reagent may be oxalyl chloride with or without DMF, thionyl chloride, $PCl_5$, or $PCl_3$.

In some embodiments, the reaction conditions of step (b) comprise an additive selected from the group consisting of trimethylsilyl chloride, water, HCl and tetrabutyl ammonium chloride.

In some embodiments, the reaction conditions of step (b) comprise a solvent selected from the group consisting of dichloromethane, acetonitrile, tetrahydrofuran, methyl-tert-butyl ether, and chloroform. In some embodiments, the reaction conditions of step (b) comprise a temperature of about −20° C. to about 40° C. In some embodiments, the reaction conditions of step (b) comprise a temperature of about 15° C. to about 25° C.

In certain embodiments, the reaction conditions of step (c) comprise an organic base. The organic base may be N,N-diisopropylethylamine, triethylamine, pyridine, and 4-dimethylaminopyridine.

In some embodiments, the reaction conditions of step (c) comprise a solvent selected from the group consisting of dichloromethane, dichloroethane, acetonitrile, tetrahydrofuran, 2-methyltetrahydrofuran, toluene, methyl-tert-butyl ether, and chloroform. In some embodiments, the reaction conditions of step (c) comprise a temperature of about 0° C. to about 40° C. In some embodiments, the reaction conditions of step (c) comprise a temperature of about 15° C. to about 25° C.

In certain embodiments, the process for preparing a compound of formula (A) further comprises forming a compound of formula (C), or a salt thereof, by:

(d) transforming a compound of formula (M):

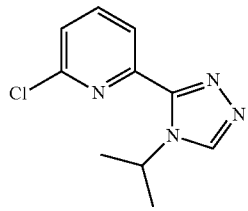

(M)

under reaction conditions sufficient to form a compound of formula (C):

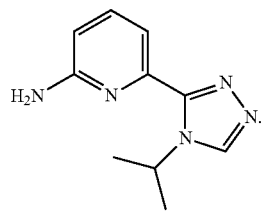

(C)

In such embodiments, the reaction conditions of step (d) comprise a base. The base may be cesium carbonate. In some embodiments, the reaction conditions of step (d) may comprise catalytic Pd(0) (e.g. Pd(dba)₂) or Pd(II) (e.g. Pd(OAc)₂) and a catalytic ligand (e.g., P(t-Bu)₃ and rac-BINAP). In some embodiments, the reaction conditions of step (d) comprise a temperature of about 20° C. to about 90° C. The solvent may be toluene or dioxane.

In certain embodiments, the process for preparing a compound of formula (A) further comprises forming a compound of formula (M) by:

(e) contacting a compound of formula (O):

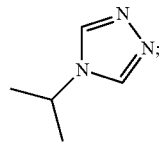

(O)

with a compound of formula (N):

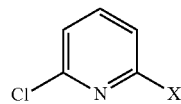

(N)

under reaction conditions sufficient to form a compound of formula (M), wherein X is a halogen, triflate, or trifluoromethanesulfonate. In some embodiments, X may be iodo or bromo.

In such embodiments, the reaction conditions of step (e) comprise a catalyst. The catalyst may be PdCl₂(PPh₃) or other Pd (II) complexes or Pd(0) complexes with trialkyl or triarylphosphine ligands. In some embodiments, the reaction conditions of step (e) comprise a co-catalyst. The co-catalyst may be CuI. In some embodiments, the reaction conditions of step (e) comprise a base. The base may be a carbonate base, such as Cs₂CO₃, K₂CO₃, and Na₂CO₃. In some embodiments, the reaction conditions of step (e) comprise a solvent selected from the group consisting of dioxane, dimethylformamide, dimethaylacetamide, dimethylsulfoxide, butyronitrile, and N-methyl-2-pyrrolidone. In some embodiments, the reaction conditions of step (d) comprise a temperature of about 80° C. to about 150° C. In some embodiments, the reaction conditions of step (d) comprise a temperature of about 95° C. to about 105° C. In certain embodiments, the process for preparing a compound of formula (A) further comprises forming compound of formula (C), or a salt thereof, by:

(d) contacting a compound of formula (O):

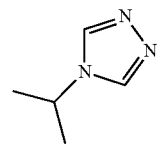

(O)

with a compound of formula (P):

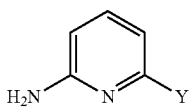

(P)

under reaction conditions sufficient to form a compound of formula (C).

wherein Y is a halogen, triflate, or trifluoromethanesulfonate. In some embodiments, Y may be chloro or bromo.

In some embodiments, the reaction conditions of step (d) comprise a catalyst, such as PdCl₂(PPh₃) or other Pd (II) complexes or Pd(0) complexes with trialkyl or triarylphosphine ligands. In some embodiments, the reaction conditions of step (d) comprise a co-catalyst. The co-catalyst may be CuI. In some embodiments, the reaction conditions of step (d) comprise a base. The base may be a carbonate base, such as $Cs_2CO_3$, $K_2CO_3$, and $Na_2CO_3$. In some embodiments, the reaction conditions of step (d) comprise a solvent selected from the group consisting of dioxane, dimethylformamide, dimethaylacetamide, dimethylsulfoxide, butyronitrile, and N-methyl-2-pyrrolidone. In some embodiments, the reaction conditions of step (d) comprise a temperature of about 80° C. to about 150° C. In some embodiments, the reaction conditions of step (d) comprise a temperature of about 95° C. to about 105° C.

In some embodiments, the reaction conditions of step (d) comprise a metallation step followed by a coupling step. In such embodiments, during the metallation, the reaction conditions of step (d) comprise a reagent selected from the group consisting of an organolithium reagent (such as n-BuLi, t-BuLi, MeLi, and s-BuLi) and a Grignard reagent (such as iPrMgCl and PhMgCl). In some embodiments, the reaction conditions of step (d) comprise $ZnCl_2$, $ZnCl_2$ with LiCl, $ZnBr_2$, or $ZnI_2$. In some embodiments, the reaction conditions of step (d) comprise a solvent selected from the group consisting of tetrahydrofuran, 2-methyltetrahydrofuran, methyl-tert-butyl ether, and diethyl ether. In some embodiments, during the coupling step, the reaction conditions of step (d) comprise a catalyst. The catalyst may be $Pd(PPh_3)_4$ or other Pd (II) complexes or Pd(0) complexes with trialkyl or triarylphosphine ligands. In some embodiments, the reaction conditions of step (d) comprise a solvent selected from the group consisting of dioxane, N-methyl-2-pyrrolidone, tetrahydrofuran, butyronitrile, and toluene.

In some embodiments, the reaction conditions of step (d) comprise a first temperature of about −78° C. to about −40° C. and a second temperature of about 80° C. to about 140° C. In some embodiments, the reaction conditions of step (d) comprise a first temperature of about −55° C. to about −60° C. and a second temperature of about 115° C. to about 125° C. In such embodiments, the metallation occurs at the first temperature, and coupling reaction occurs at the second temperature.

In one embodiment, the present disclosure provides for a process for preparing a compound of formula (D), a salt thereof, or a solvate thereof:

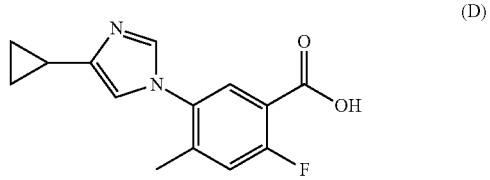 [SMILES: Cc1cc(F)c(C(=O)O)cc1-n1cnc(C2CC2)c1]

(D)

comprising the steps of:
(a) carboalkoxylating a compound of formula (E) or a salt thereof:

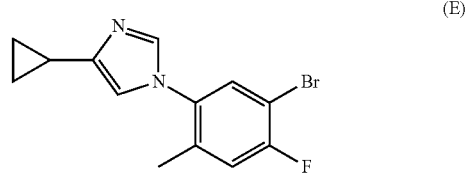 [SMILES: Cc1cc(F)c(Br)cc1-n1cnc(C2CC2)c1]

(E)

under reaction conditions sufficient to form a compound of formula (Q):

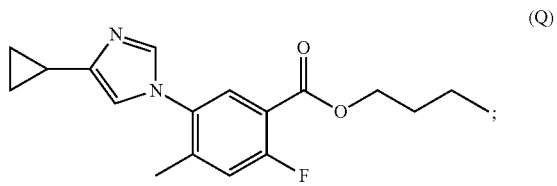 [SMILES: CCCCOC(=O)c1cc(-n2cnc(C3CC3)c2)c(C)cc1F]

(Q)

and (b) hydrolyzing a compound of formula (Q) under reaction conditions sufficient to form a compound of formula (D), a hydrate, solvate or salt thereof.

In certain embodiments, the reaction conditions of step (a) comprise a catalyst and a base. The catalyst may be $PdCl_2(PPh)_3$ or other Pd (II) complexes or Pd(0) complexes. The base may be a carbonate base (such as $K_2CO_3$, $Cs_2CO_3$, and $Na_2CO_3$), an acetate (such as sodium acetate or potassium acetate), or an organic base, such as (tetramethylethylenediamine, triethylamine, and diisopropylethyl amine). In some embodiments, the reaction conditions of step (a) comprise a solvent selected from the group consisting of butanol, dimethylformamide, and mixtures thereof. The reaction conditions of step (a) comprise a carbon monoxide pressure of about 5 psig to about 50 psig or about 5 psig. In some embodiments, the reaction conditions of step (a) comprise a temperature of about 70° C. to about 115° C. In some embodiments, the reaction conditions of step (a) comprise a temperature of about 85° C. to about 95° C.

In certain embodiments, the reaction conditions of step (b) comprise a base. The base may be aqueous sodium hydroxide. In some embodiments, the reaction conditions of step (b) comprise a solvent selected from the group consisting of methanol, tetrahydrofuran, ethanol, propanol, and butanol. In some embodiments, the reaction conditions of step (b) comprise a temperature of about 10° C. to about 60° C. In some embodiments, the reaction conditions of step (b) comprise a temperature of about 20° C. to about 25° C.

Scheme 3 represents an exemplary synthesis of a compound of formula (A) and can be carried out according to the embodiments described herein. The particular reaction conditions and reagents employed in Scheme 3 are discussed below.

Scheme 3

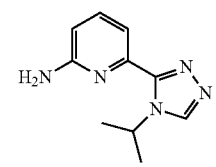

Compound (C)

CO
Pd catalyst, base
―――――――→
DMF, 100° C.

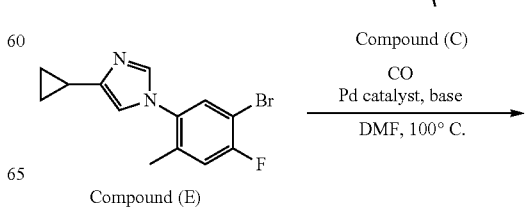

Compound (E)

-continued

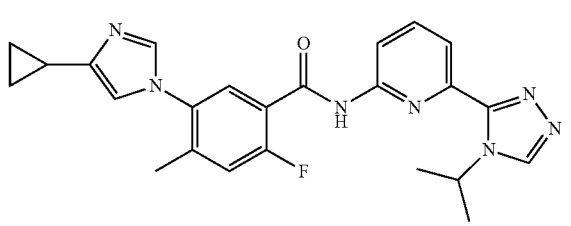

Compound (A)

In one embodiment, the present disclosure provides for a process for preparing a compound of formula (A):

(A)

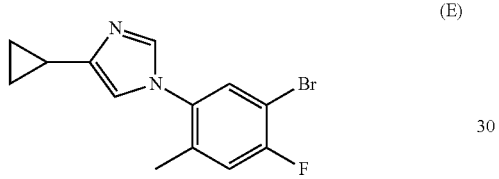

comprising the steps of:
(a) contacting a compound of formula (E) or a salt thereof:

(E)

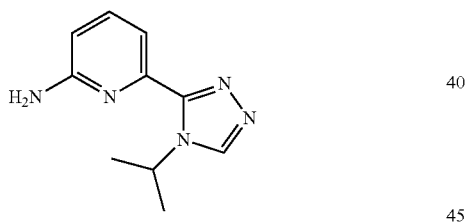

with a compound of formula (C) or a salt thereof:

(C)

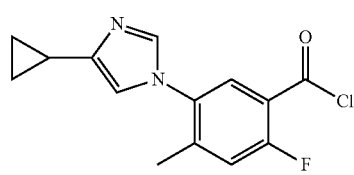 [SMILES: Cc1cc(F)c(C(=O)Cl)cc1-n1cnc(C2CC2)c1]

under reaction conditions sufficient to form a compound of formula (A).

In certain embodiments, the reaction conditions of step (a) comprise a catalyst. The catalyst may be Pd(OAc)$_2$ with Ad$_2$Pd(n-Bu) or other Pd (II) complexes or Pd(0) complexes with trialkyl or triarylphosphine ligands, including but not limited to: Pd(dppf)Cl$_2$, PdCl$_2$ (PPh$_3$)$_2$, PdCl$_2$ (PhCN)$_2$, PdCl$_2$(A-Phos)$_2$, Pd(OAc)$_2$/PPh$_3$, Pd(OAc)$_2$/ PPh$_3$, Pd(OAc)$_2$/dppp, Pd(OAc)$_2$/xantphos, Pd(OAc)$_2$/t-Bu$_3$P. In some embodiments, the reaction conditions comprise a base. The base may be an organic base (such as an triethylamine, tetramethylethylenediamine, and diisopropylethyl amine), a carbonate base (such as Cs$_2$CO$_3$, K$_2$CO$_3$ and Na$_2$CO$_3$), or an acetate base (such as sodium acetate or potassium acetate). In some embodiments, the reaction conditions comprise a solvent selected from the group consisting of dimethylformamide, N-methyl-2-pyrrolidone, dioxane, and toluene. In some embodiments, the reaction conditions comprise a temperature of about 90° C. to about 120° C. In some embodiments, the reaction conditions comprise a temperature of about 100° C. In some embodiments, the reaction conditions comprise a carbon monoxide pressure of about 20 psig to about 60 psig or about 20 psig.

Compounds

In other embodiments, the disclosure provides for intermediate compounds that are useful in the processes described herein. Thus, for instance, one embodiment is a compound of the formula (B) or a salt thereof:

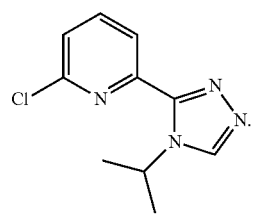

In some embodiments, a compound of formula (B) may be a hydrochloride salt.

Another embodiment is a compound of formula (M):

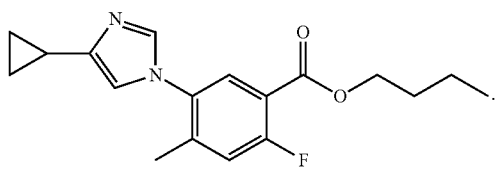 [SMILES: CCCCOC(=O)c1cc(-n2cnc(C3CC3)c2)c(C)cc1F]

Also provided herein are compounds of formula (Q):

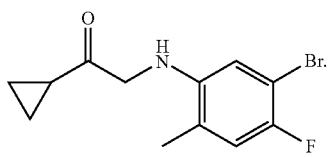 [SMILES: Cc1cc(F)c(Br)cc1NCC(=O)C1CC1]

Also provided herein are compounds of formula (G):

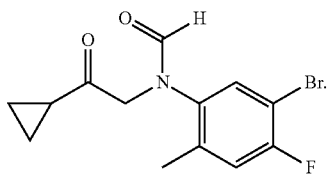 [SMILES: Cc1cc(F)c(Br)cc1N(C=O)CC(=O)C1CC1]

Also provided herein are compounds of formula (F):

Also provided herein are compounds of formula (E):

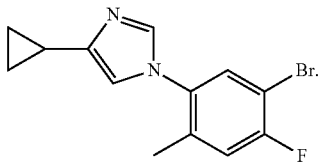 [SMILES: Cc1cc(F)c(Br)cc1-n1cnc(C2CC2)c1]

Also provided herein are compounds of formula (D):

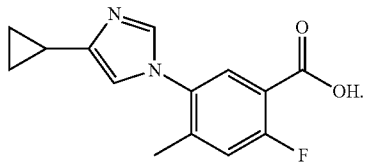 [SMILES: Cc1cc(F)c(C(=O)O)cc1-n1cnc(C2CC2)c1]

In some embodiments, a compound of formula (D) may be a hydrochloride salt. Another embodiment is crystalline 5-(4-cyclopropyl-1H-imidazol-1-1-2-fluoro-4-methylbenzoic acid hydrochloride (Compound of formula (D-a) Form I) characterized by an X-ray powder diffractogram comprising the following peaks: 7.3, 22.3, 23.4, 23.9, and 26.8° 2θ±0.2° 2θ, as determined on a diffractometer using Cu—Kα radiation at a wavelength of 1.5406 Å. The diffractogram comprises additional peaks at 11.5, 13.4, 20.9, and 22.0° 2θ±0.2° 2θ. Compound of formula (D-a) Form I is also characterized by its full X-ray powder diffractogram as substantially shown in FIG. 1. In some embodiments, the diffractogram of a compound of formula (D-a) Form I comprises the following peaks: 7.3, 8.9, 11.5, 13.4, 17.1, 17.8, 18.6, 20.9, 22.0, 22.3, 23.4, 23.9, 26.8, 27.5, 29.6, 31.1, 32.0, and 35.4° 2θ±0.2° 2θ. In some embodiments, a compound of formula (D-a) Form I is characterized by a differential scanning calorimetry (DSC) curve that comprises an endotherm at about 210° C. Compound of formula (D-a) Form I is characterized by its full DSC curve as substantially shown in FIG. 2.

Another embodiment is crystalline 5-(4-cyclopropyl-1H-imidazol-1-1-2-fluoro-4-methylbenzoic acid hydrochloride (Compound of formula (D-a) Form II) characterized by an X-ray powder diffractogram comprising the following peaks: 8.7, 12.1, 25.7, and 26.3° 2θ±0.2° 2θ, as determined on a diffractometer using Cu—Kα radiation at a wavelength of 1.5406 Å. The diffractogram comprises additional peaks at 17.3, 19.0, 22.4, 28.6, and 29.7° 2θ±0.2° 2θ. Compound of formula (D-a) Form II is also characterized by its full X-ray powder diffractogram as substantially shown in FIG. 4. In some embodiments, the diffractogram of a compound of formula (D-a) Form II comprises the following peaks: 8.7, 9.2, 12.1, 17.3, 18.3, 18.6, 19.0, 20.9, 21.1, 21.5, 22.4, 24.2, 25.7, 26.3, 26.7, 28.6, and 29.7° 2θ±0.2° 2θ. In some embodiments, a compound of formula (D-a) Form II is characterized by a differential scanning calorimetry (DSC) curve that comprises an endotherm at about 217° C. Compound of formula (D-a) Form II is characterized by its full DSC curve as substantially shown in FIG. 5.

In some embodiments, a compound of formula (D) may be a hydrate. Another embodiment is crystalline 5-(4-cyclopropyl-1H-imidazol-1-1-2-fluoro-4-methylbenzoic acid hydrate (Compound of formula (D) hydrate Form I) characterized by an X-ray powder diffractogram comprising the following peaks: 9.5, 20.4, 24.3, 26.5, and 28.7° 2θ±0.2° 2θ, as determined on a diffractometer using Cu—Kα radiation at a wavelength of 1.5406 Å. The diffractogram comprises additional peaks at 11.5, 12.8, 13.2, 15.9, 18.5, and 19.0° 2θ±0.2° 2θ. Compound of formula (D) hydrate Form I is also characterized by its full X-ray powder diffractogram as substantially shown in FIG. 7. In some embodiments, the diffractogram of a compound of formula (D) hydrate Form I comprises the following peaks: 9.5, 11.5, 12.8, 13.2, 14.1, 15.9, 17.1, 17.2, 18.5, 19.0, 19.8, 20.4, 22.8, 23.0, 24.3, 24.6, 25.0, 25.6, 26.5, 26.8, 28.7, 29.1, and 30.6° 2θ±0.2° 2θ. In some embodiments, a compound of formula (D) hydrate Form I is characterized by a differential scanning calorimetry (DSC) curve that comprises an endotherm at about 252° C. In some embodiments, the DSC curve further comprises an endotherm at about 89° C. Compound of formula (D) hydrate Form I is characterized by its full DSC curve as substantially shown in FIG. 8.

In some embodiments, a compound of formula (D) may be anhydrous. Another embodiment is crystalline 5-(4-cyclopropyl-1H-imidazol-1-1-2-fluoro-4-methylbenzoic acid (Compound of formula (D) Form I) characterized by an X-ray powder diffractogram comprising the following peaks: 8.7, 15.2, 21.5, and 23.8° 2θ±0.2° 2θ, as determined on a diffractometer using Cu—Kα radiation at a wavelength of 1.5406 Å. The diffractogram comprises additional peaks at 12.4, 14.0, 14.1, 17.4, and 26.2° 2θ±0.2° 2θ. Compound of formula (D) Form I is also characterized by its full X-ray powder diffractogram as substantially shown in FIG. 10. In some embodiments, the diffractogram of a compound of formula (D) Form I comprises the following peaks: 8.7, 12.4, 14.0, 14.1, 15.2, 17.4, 17.9, 18.2, 20.5, 21.5, 22.3, 22.7, 23.3, 23.8, 24.4, 26.2, 28.1, 28.4, and 29.2° 2θ±0.2° 2θ. In some embodiments, a compound of formula (D) Form I is characterized by a differential scanning calorimetry (DSC) curve that comprises an endotherm at about 252° C. Compound of formula (D) Form I is characterized by its full DSC curve as substantially shown in FIG. 11.

Another embodiment is crystalline 5-(4-cyclopropyl-1H-imidazol-1-1-2-fluoro-4-methylbenzoic acid (Compound of formula (D) Form II) characterized by a calculated X-ray powder diffractogram comprising the following peaks: 8.4, 13.6, and 15.5° 2θ±0.2° 2θ, as determined on a diffractometer using Cu—Kα radiation at a wavelength of 1.5406 Å. The calculated diffractogram comprises additional peaks at 9.8, 13.6, and 25.4° 2θ±0.2° 2θ. A mixture of compound of formula (D) Form II and compound of formula (D) Form I is also characterized by its full X-ray powder diffractogram as substantially shown in FIG. 18. In some embodiments, the calculated diffractogram of a compound of formula (D) Form I comprises the following peaks: 5.2, 8.4, 9.8, 10.4, 13.2, 13.6, 14.4, 15.5, 19.5, 25.0, 25.4, and 27.5° 2θ±0.2° 2θ. In some embodiments, a mixture of a compound of formula (D) Form I and Compound of formula (D) Form II is characterized by a differential scanning calorimetry (DSC) curve that comprises an endotherm at about 252° C. In some embodiments, the DSC curve further comprises an endotherm at about 131° C. A mixture of a compound of formula (D) Form I and Compound of formula (D) Form II is characterized by its full DSC curve as substantially shown in FIG. 17.

Figure 13:
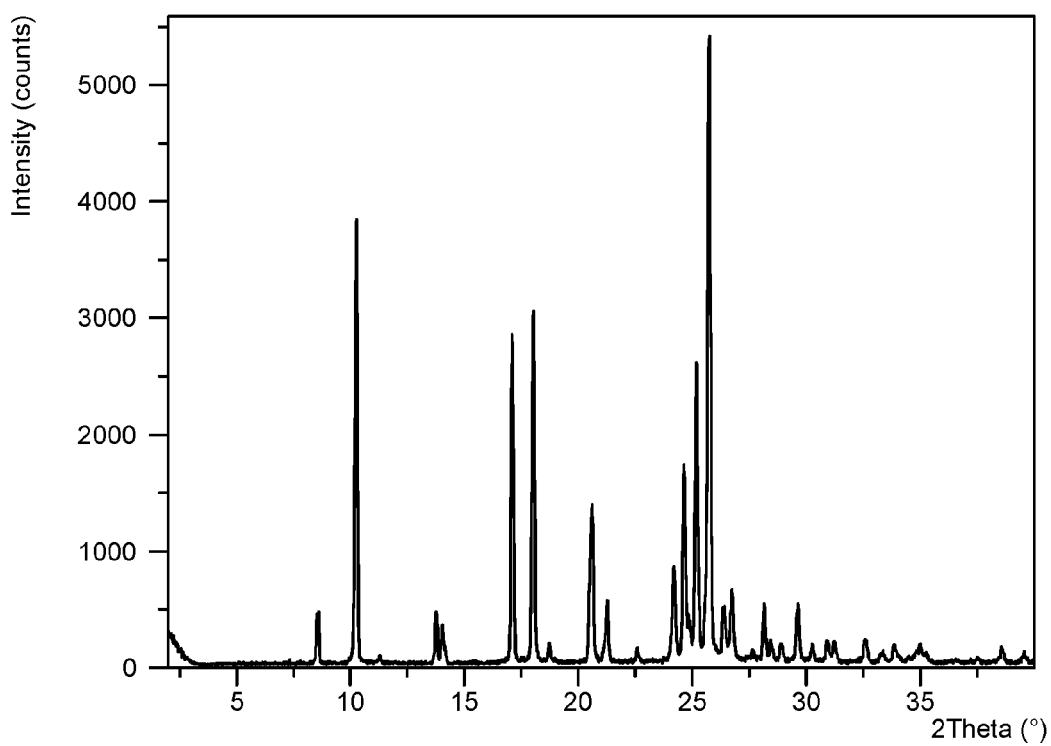
FIG. 13 shows an X-ray powder diffraction (XRPD) of Compound of formula (D) Form III.

Another embodiment is crystalline 5-(4-cyclopropyl-1H-imidazol-1-1-2-fluoro-4-methylbenzoic acid (Compound of formula (D) Form III) characterized by an X-ray powder diffractogram comprising the following peaks: 10.3, 17.1, 18.0, and 25.7° 2θ±0.2° 2θ, as determined on a diffractometer using Cu—Kα radiation at a wavelength of 1.5406 Å. The diffractogram comprises additional peaks at 20.6, 24.2, 24.6, and 25.2° 2θ±0.2° 2θ. Compound of formula (D) Form III is also characterized by its full X-ray powder diffractogram as substantially shown in FIG. 13. In some embodiments, the diffractogram of a compound of formula (D) Form III comprises the following peaks: 8.6, 10.3, 13.8, 14.0, 17.1, 18.0, 20.6, 21.3, 24.2, 24.6, 25.2, 25.7, 26.3, 26.7, 28.2, and 29.6° 2θ±0.2° 2θ. In some embodiments, a compound of formula (D) Form III is characterized by a differential scanning calorimetry (DSC) curve that comprises an endotherm at about 253° C. In some embodiments, the DSC curve further comprises an endotherm at about 164° C.

Figure 14:
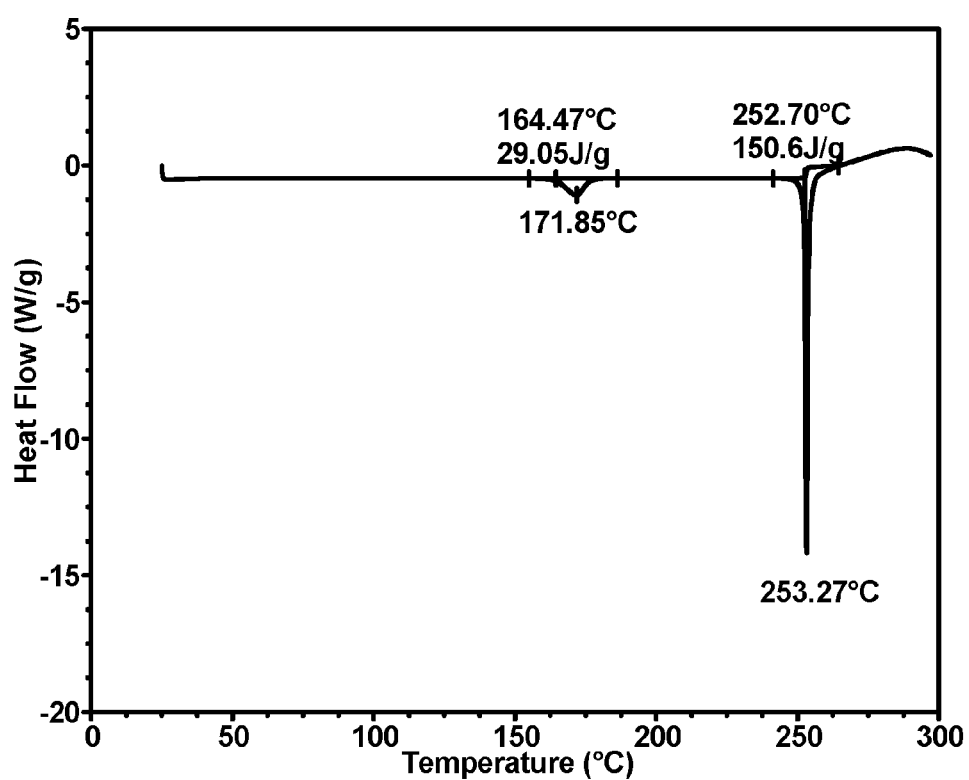
FIG. 14 shows a differential scanning calorimeter (DSC) curve of Compound of formula (D) Form III.

Compound of formula (D) Form III is characterized by its full DSC curve as substantially shown in FIG. 14.

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Example 1: Synthesis of Compound (A)

i)

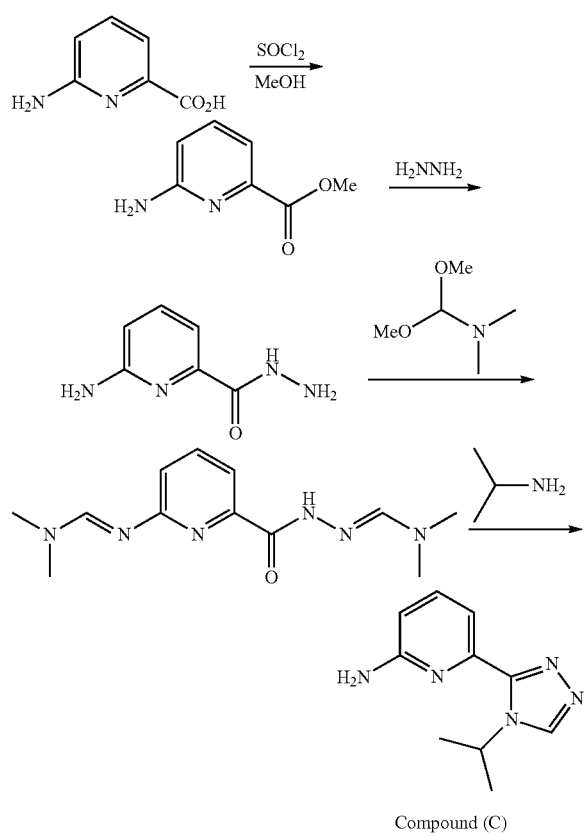

ii)

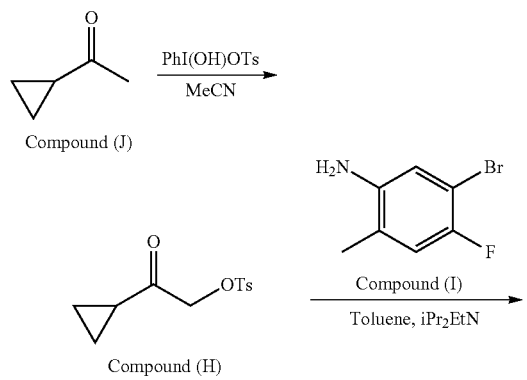

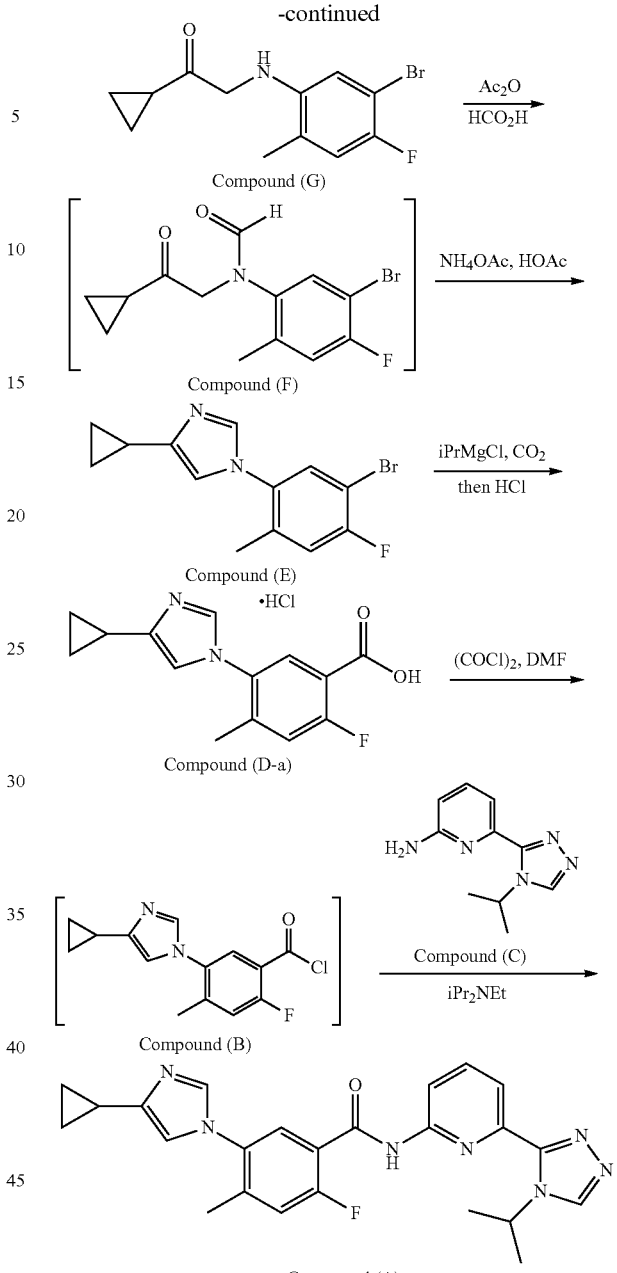

Hydroxytosylation of Compound (J) to Form Compound (H)

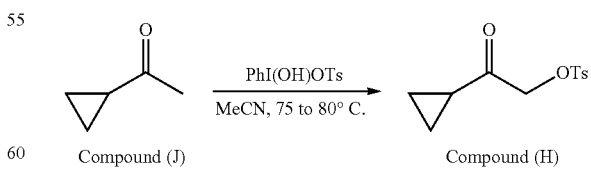

Koser's reagent, PhI(OH)OTs, (1.0 eq.) and acetonitrile (5 vols) are charged to a flask. Cyclopropylmethyl ketone (Compound (J), 1.2 eq.) is charged and the mixture is heated to about 70° C. to about 75° C. Once the reaction is complete, the contents are cooled and concentrated.

The residue is diluted in dichloromethane (about 2.5 vols) and washed with water (2× about 1 to 2 volumes). The organic phase is concentrated to approximately 1.5 vols and the product is triturated with hexanes (about 1.5 to 2 vols) and concentrated to remove dichloromethane and the distilled volume is replaced with hexanes. The slurry is agitated for about two hours, filtered and washed with hexanes. The solids are dried under vacuum at about 40° C. to afford Compound (H). $^1$H NMR (400 MHz, DMSO-$d_6$): δ 7.82 (d, 2H, J=8.0 Hz), 7.49 (d, 2H, J=8.0 Hz), 4.98 (s, 2H), 2.42 (s, 3H), 2.02-2.08 (m, 1H), 0.95-0.91 (m, 2H), 0.89-0.82 (m, 2H). $^{13}$C NMR (100 MHz, DMSO-$d_6$): 202.39, 145.60, 132.76, 130.57, 128.12, 72.98, 21.52, 17.41, 11.39.

Alternative reagents and reaction conditions to those disclosed above may also be employed. For example, in lieu of Koser's reagent, alternative reagents may include, but are not limited to, (diacetoxyiodo)benzene organosulfonic acid, (diacetoxyiodo)benzene and p-toluenesulfonic acid, iodosylbenzene/p-toluenesulfonic acid, m-chloroperbenzoic acid/p-toluenesulfonic acid, poly(4-hydroxy tosyloxyiodo) styrenes, N-methyl-O-tosylhydroxylamine, Dess-Martin periodinane/p-toluenesulfonic acid, HIO$_3$/p-toluenesulfonic acid, and o-iodoxybenzoic acid/p-toluenesulfonic acid. Various solvents, such as toluene, benzene, tetrahydrofuran, 2-methyltetrahydrofuran, dichloromethane, and chloroform, may be employed. The reaction may take place at temperatures that range from about 20° C. to about 100° C.

Alkylation of Compound (H) with Compound (I) to Form Compound (G)

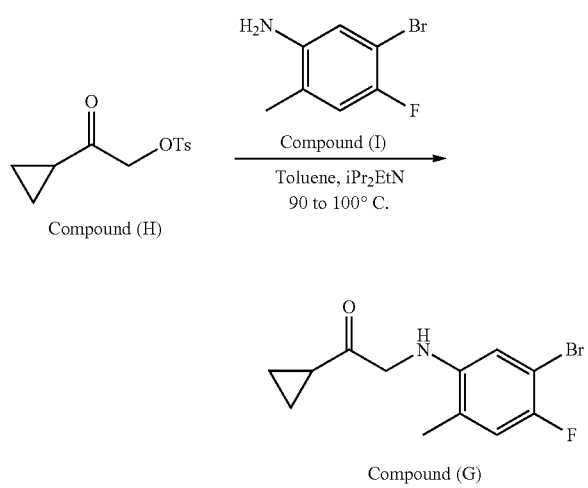

To a mixture of Compound (I) (1.0 equiv) and Compound (H) (1.1 equiv) in toluene (5 vols) is charged iPr$_2$NEt (2.1 equiv). The mixture is heated to about 90 to about 100° C. and aged for about less than 10 hours. Upon completion, the mixture is cooled and diluted with water (about 5 to about 6 vols). The biphasic mixture is separated and the organic solution is washed sequentially with aq. NH$_4$Cl (about 27 wt %, about 2 to about 3 vols), aq. NaHCO$_3$ (about 9 wt %, about 2 to about 3 vols), and aq. NaCl (about 15 wt %, about 1 vols). The organic solution is dried over Na$_2$SO$_4$, filtered, and washed with toluene (about 2 to about 3 vols). The solution is concentrated under vacuum at about 45° C. and the residue is crystallized by the addition of hexane at about 20° C. to about 25° C. and at about 10° C. to about 15° C. The slurry is filtered, washed with cooled isopropanol (about 1 vol) and dried under vacuum at about 37° C. to about 43° C. to afford Compound (G). $^1$H NMR (400 MHz, DMSO-$d_6$): δ 7.05 (d, 1H, J=12.0 Hz), 6.51 (d, 1H, J=8.0 Hz), 5.27 (t, 1H, J=4.0 Hz), 4.17 (d, 2H, J=4.0 Hz), 2.21-2.14 (m, 1H), 2.10 (s, 3H), 0.96-0.86 (m, 4H). $^{13}$C NMR (100 MHz, DMSO-$d_6$): 208.17, 151.63, 149.32, 143.99, 143.97, 123.81, 123.74, 118.13, 117.90, 112.87, 105.09, 104.88, 53.72, 18.33, 17.43, 17.42, 10.85.

Alternative reagents and reaction conditions to those disclosed above may also be employed. For example, alternative bases, including but not limited to organic bases (e.g., DBU and DMAP), alkali metal bases (e.g., NaH), hexamethyldisilazane bases (e.g., sodium, potassium and lithium hexamethyldisilazide), carbonate bases (e.g., Cs$_2$CO$_3$, Na$_2$CO$_3$), and potassium tert-butoxide. Various solvents, such as THF, MTBE, 2-MeTHF, acetonitrile, dioxane, benzene, DMF, DMAc, NMP, may be employed. The reaction may take place at temperatures that range from about −78° C. to about 100° C.

Formylation of Compound (G) to Form Compound (F)

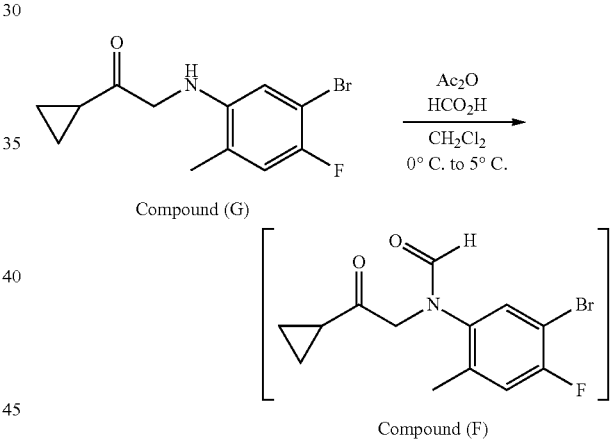

Acetic anhydride (4 equiv) is added to aqueous formic acid (about 3 to about 4 vols) at about 0° C. to about 5° C. and the mixture is agitated. Compound (G) (1.0 equiv) in DCM (about 3 vols) is charged. The reaction is aged at about 0 to about 5° C. until it is deemed complete. Upon reaction completion, water (about 4 vols) is charged and the mixture is adjusted to about pH 8-9 by the addition of 40-50% aqueous NaOH with the content temperature maintained between about 0° C. to about 15° C. The biphasic mixture is separated and the aqueous solution is extracted with dichloromethane (about 6 vols). The organic solution is washed with saturated aqueous NaCl (about 4 vols), dried over Na$_2$SO$_4$, and filtered. Compound (F) is carried forward to the next step as a solution in dichloromethane without further purification. $^1$H NMR (400 MHz, DMSO-$d_6$): δ (mixture of amide rotamers) 8.17 (s, 1H), 8.14 (s, 1H), 7.61 (d, 1H, J=8.0 Hz), 7.45 (d, 1H, J=8.0 Hz), 7.42 (d, 1H, J=12.0 Hz), 7.33 (d, 1H, J=12.0 Hz), 4.87 (s, 2H), 4.68 (s, 2H), 2.25 (s, 3H), 2.16 (s, 3H), 2.12-2.03 (m, 1H), 0.98-0.85 (m, 4H). $^{13}$C NMR (100 MHz, DMSO-d$_6$): 206.68 (204.85), 163.71 (163.22), 158.95 (158.69), 156.51 (156.35), 139.09 (139.02), 138.61 (138.53), 137.58 (137.55), 133.35 (133.34), 132.45, 119.02 (118.79), 118.58 (118.36), 105.35 (105.03), 104.77 (104.55), 58.68, 55.40, 17.84 (17.77).

Alternative reagents and reaction conditions to those disclosed above may also be employed. For example, in lieu of acetic anhydride and formic acid, acetic acid monoanhydride with carbonic acid or trifluoroacetic anhydride with formic acid may be used. Various solvents, such as chloroform, acetonitrile, isopropyl acetate, or THF, may be employed. The reaction may take place at temperatures that range from about −10° C. to about 40° C.

Imidazole Cyclization to Form Compound (E)

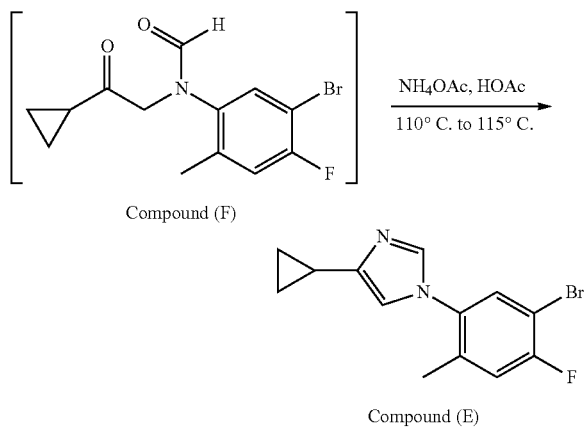

To a solution of Compound (F) (1.0 equiv) in DCM is charged acetic acid (about 5 vols). The solution is concentrated under vacuum at about 35° C. to remove the bulk of DCM and ammonium acetate (3.9 equiv) is added. The mixture is heated to about 110° C. to about 115° C. and agitated until the reaction is deemed complete. The reaction is cooled, diluted with water (about 10 vols) and iPrOAc (about 6 vols). The mixture is adjusted to about pH 8-9 by the addition of 40-50% aqueous NaOH. The biphasic mixture is separated. Sodium chloride (about 0.3 wt equiv wrt Compound (F)) is charged to the aqueous layer and the aqueous layer is extracted with iPrOAc (about 2 vols). The organic solution is washed with water (about 5 vols) and aq. NaCl (about 10 wt %, about 4 to about 5 vols). The solution is concentrated under vacuum and solvent exchanged to about 2-3 vols N,N-dimethylacetamide (DMAc). Water (about 5 to about 6 vols) is charged to afford Compound (E) as a slurry. The slurry is filtered and washed sequentially with DMAc/water, water, and hexanes. The resulting solids are dried under vacuum at about 55° C. to afford Compound (E). $^1$H NMR (400 MHz, DMSO-d$_6$): δ 7.68 (d, 1H, J=4.0 Hz), 7.64 (d, 1H, J=1.0 Hz), 7.46 (d, 1H, J=12.0 Hz), 7.12 (d, 1H, J=1.0 Hz), 2.12 (s, 3H), 1.85-1.79 (m, 1H), 0.81-0.76 (m, 2H), 0.70-0.66 (2H). $^{13}$C NMR (100 MHz, DMSO-d$_6$): 159.11, 156.67, 156.67, 143.94, 137.36, 136.19, 136.11, 134.44, 134.41, 131.21, 131.20, 119.05, 118.82, 116.21, 105.56, 105.34, 17.72, 17.71, 9.26, 7.44.

Alternative reagents and reaction conditions to those disclosed above may also be employed. For example, in lieu of ammonium acetate, alternative sources of ammonia may be used, including but not limited to ammonium formate and ammonium hydroxide. Various solvents, such as toluene, benzene, and isopropanol, may be employed. The reaction may take place at temperatures that range from about 80° C. to about 120° C.

Carboxylation of Compound (E) to Form Compound (D)

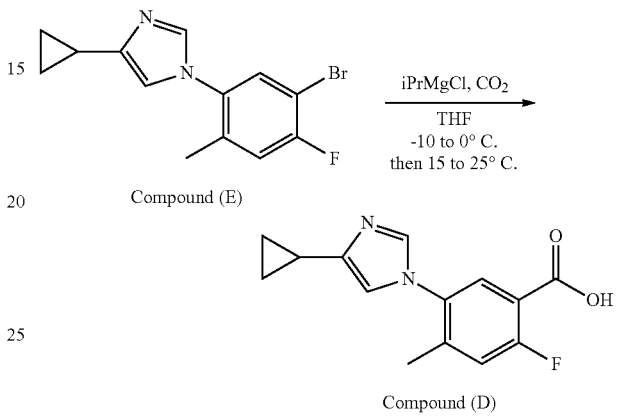

A mixture of Compound (E) (1.0 equiv) in THF (about 15 vols) was cooled to about −10 to about 0° C. and a solution of iPrMgCl (2.0 M in THF, 1.2 equiv) was charged slowly to maintain the internal temperature below about 5° C. The mixture was stirred for about 1 hour at about −5 to about 5° C. after which CO$_2$ was bubbled slowly into the mixture (exothermic). The addition is continued until the exotherm subsides and the internal temperature typically increases to about 15 to about 25° C. after the addition. Upon reaction completion, the mixture is concentrated under vacuum to approximately 3 vols and water (about 6 to about 7 vols) is added, followed by about 1 vol 6M HCl. MTBE (about 10 vols) is added and the biphasic mixture is separated. A solution of 6 M HCl is added slowly to the aqueous layer to adjust the pH (initially at >10) to approximately 4.8. The mixture is seeded with Compound (D) (if necessary), which was formed according to the procedure outlined above, and the resultant slurry is cooled slowly to about 0° C. to about 5° C. and aged. The slurry is filtered, washed with water (about 4 vols), isopropanol (about 4 vols), followed by n-heptane (about 6 vols). The solids are dried under vacuum at about 40° C. to afford Compound (D). $^1$H NMR (400 MHz, DMSO-d$_6$): δ 7.69 (d, 1H, J=2.0 Hz), 7.67 (d, 1H, J=8.0 Hz), 7.40 (d, 1H, J=8.0 Hz), 7.15 (d, 1H, J=2.0 Hz), 2.20 (s, 3H), 1.87-1.80 (m, 1H), 0.81-0.77 (m, 2H), 0.71-0.67 (m, 2H). $^{13}$C NMR (100 MHz, DMSO-d$_6$): 164.52, 164.48, 161.68, 159.12, 143.95, 141.63, 141.53, 137.34, 133.21, 133.18, 129.70, 119.85, 119.61, 118.08, 117.97, 116.25, 18.02, 9.21, 7.48.

Alternative reagents and reaction conditions to those disclosed above may also be employed. For example, alternative bases, including but not limited to organolithium bases (e.g., MeLi, n-BuLi, t-BuLi, and sec-BuLi) and Grignard bases (e.g., MeMgCl, n-BuMgCl, and PhMgCl). Various solvents, such as 2-MeTHF, dioxane, MTBE, and Et$_2$O, may be employed. The reaction may initially take place at temperatures that range from about −20° C. to about 40° C. and then continue at temperature that range from about −10° C. to about 50° C.

Conversion of Compound (D) to Form Compound (D-a)

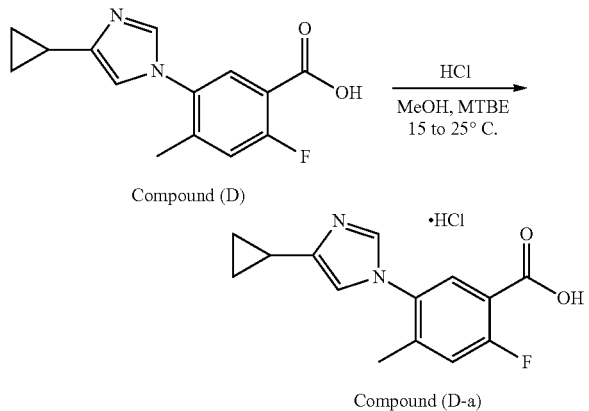

Compound (D)

Compound (D-a)

To a mixture of Compound (D) (1.0 equiv) in methanol (about 4 vols) at about 15° C. to about 25° C. is charged concentrated HCl (1.1 equiv relative to Compound (D)). The mixture is aged until most of the Compound (D) is dissolved, seeded with Compound (D-a) (0.005 equiv), which was formed according to the procedure outlined above, and MTBE (about 3 vols relative to the amount of seed) is charged slowly. The slurry is aged, filtered, and rinsed with MTBE (5 vols) and the solids are dried under vacuum at about 40° C. to afford Compound (D-a). $^1$H NMR (400 MHz, DMSO-$d_6$): δ 9.34 (s, 1H), 8.00 (d, 1H, J=8.0 Hz), 7.76 (d, 1H, J=2.0 Hz), 7.54 (d, 1H, J=12.0 Hz), 2.25 (s, 3H), 2.08-2.01 (m, 1H), 1.05-1.00 (m, 2H), 0.92-0.88 (m, 2H). $^{13}$C NMR (100 MHz, DMSO-$d_6$): 164.08, 164.05, 162.73, 160.14, 142.11, 142.01, 137.11, 135.91, 131.14, 131.11, 130.73, 120.19, 119.96, 118.78, 118.39, 118.27, 17.71, 8.24, 6.13.

Carboxylation of Compound (E) to Form Compound (D) Hydrate

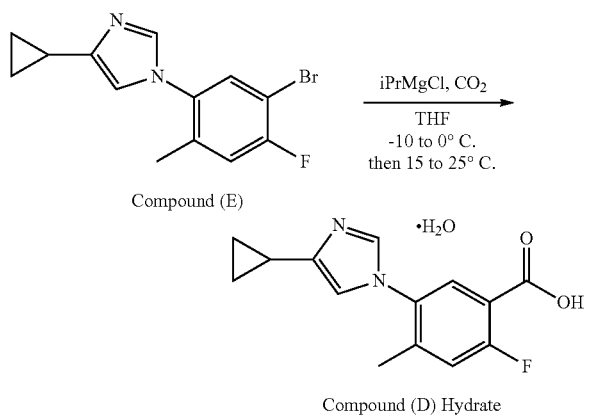

Compound (E)

Compound (D) Hydrate

A mixture of Compound (E) (1.0 equiv) in THF (about 15 vols) was cooled to about −10 to about 0° C. and a solution of iPrMgCl (2.0 M in THF, 1.2 equiv) was charged slowly to maintain the internal temperature below about 5° C. The mixture was stirred for about 1 hour at about −5 to about 5° C. after which CO₂ was bubbled slowly into the mixture (exothermic). The addition is continued until the exotherm subsides and the internal temperature typically increases to about 15 to about 25° C. after the addition. Upon reaction completion, the mixture is concentrated under vacuum to approximately 3 vols and water (about 6 to about 7 vols) is added, followed by about 1 vol 6 M HCl. MTBE (about 10 vols) is added and the biphasic mixture is separated. A solution of 6 M HCl is added slowly to the aqueous layer to adjust the pH (initially at >10) to approximately 4.8. The mixture is seeded with Compound (D) (if necessary), which was formed according to the procedure outlined above, and the resultant slurry is cooled slowly to about 0° C. to about 5° C. and aged. The slurry is filtered and washed with water (about 4 vols). The solids are dried under vacuum at about 40° C. to afford Compound (D) hydrate. $^1$H NMR (400 MHz, DMSO-$d_6$): δ 7.69 (d, 1H, J=2.0 Hz), 7.67 (d, 1H, J=8.0 Hz), 7.40 (d, 1H, J=8.0 Hz), 7.15 (d, 1H, J=2.0 Hz), 2.20 (s, 3H), 1.87-1.80 (m, 1H), 0.81-0.77 (m, 2H), 0.71-0.67 (m, 2H). $^{13}$C NMR (100 MHz, DMSO-$d_6$): 164.52, 164.48, 161.68, 159.12, 143.95, 141.63, 141.53, 137.34, 133.21, 133.18, 129.70, 119.85, 119.61, 118.08, 117.97, 116.25, 18.02, 9.21, 7.48.

Alternative reagents and reaction conditions to those disclosed above may also be employed. For example, alternative bases, including but not limited to organolithium bases (e.g., MeLi, n-BuLi, t-BuLi, and sec-BuLi) and Grignard bases (e.g., MeMgCl, n-BuMgCl, and PhMgCl). Various solvents, such as 2-MeTHF, dioxane, MTBE, and Et₂O, may be employed. The reaction may initially take place at temperatures that range from about −20° C. to about 40° C. and then continue at temperature that range from about −10° C. to about 50° C.

Acid Chloride Formation Using Compound (D-a) to Form Compound (B)

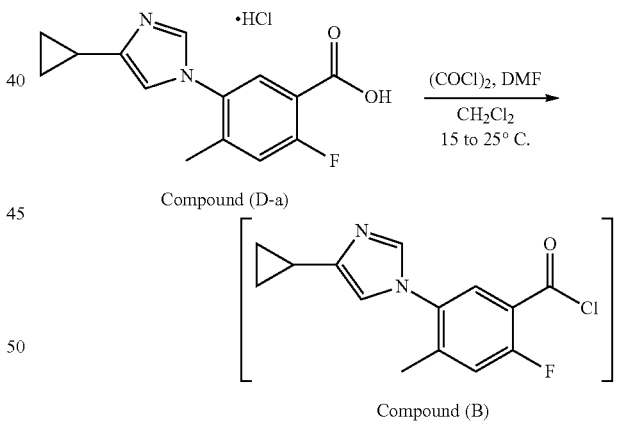

Compound (D-a)

Compound (B)

To a mixture of Compound (D-a) (1.0 equiv), DCM (about 10 vols) and DMF (0.1 equiv), a solution of oxalyl chloride (about 1.7 equiv) was slowly charged to maintain the internal temperature below about 30° C. The mixture was stirred for about 1 hour at about 20° C. after which time the mixture is distilled to about about 4 vols total volume. DCM (about 5 vols) is repeatedly charged and the mixture distilled to about 4 vols total volume. DCM is then charged to bring the total volume to about 12 vols of Compound (B). The solution is carried forward to the next step without further purification.

Alternative reagents and reaction conditions to those disclosed above may also be employed. For example, in lieu of Compound (D-a), compound (D) may be used. Additionally, in lieu of oxalyl chloride and DMF, thionyl chloride, PCl$_5$, and PCl$_3$ may be used. Various solvents, such as MeCN, THF, and MTBE, may be employed. In some embodiments, additives may be used, including but not limited to trimhetylsilyl chloride, water, HCl, or tetrabutyl ammonium chloride. The reaction may take place at temperatures that range from about −20° C. to about 40° C.

Acid Chloride Formation Using Compound (D) Hydrate to Form Compound (B)

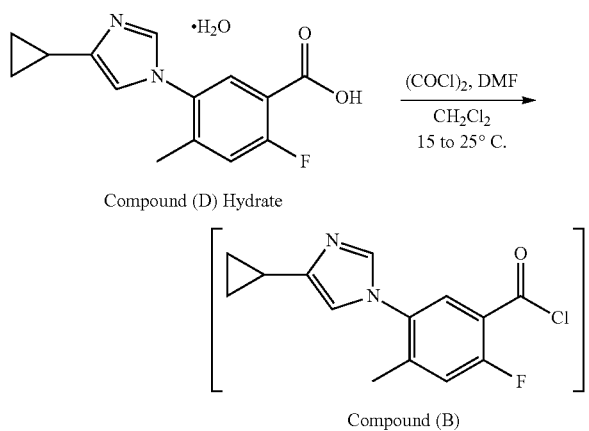

To a mixture of Compound (D) hydrate (1.0 equiv), DCM (about 10 vols) and DMF (0.1 equiv), a solution of oxalyl chloride (1.2 equiv) was slowly charged to maintain the internal temperature below about 30° C. The mixture was stirred for about 1 hour at about 20° C. after which time the mixture is distilled to about about 4 vols total volume. DCM (about 5 vols) is repeatedly charged and the mixture distilled to about 4 vols total volume. DCM is then charged to bring the total volume to about 12 vols of Compound (B). The solution is carried forward to the next step without further purification.

Alternative reagents and reaction conditions to those disclosed above may also be employed. For example, in lieu of Compound (D) hydrate, compound (D) may be used. Additionally, in lieu of oxalyl chloride and DMF, thionyl chloride, PCl$_5$, and PCl$_3$ may be used. Various solvents, such as MeCN, THF, and MTBE, may be employed. In some embodiments, additives may be used, including but not limited to trimethylsilyl chloride, water, HCl, or tetrabutyl ammonium chloride. The reaction may take place at temperatures that range from about −20° C. to about 40° C.

Amide Bond Formation to Form Compound (A)

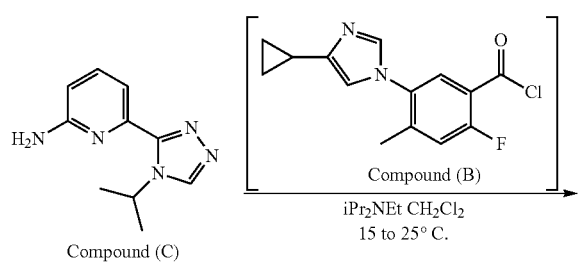

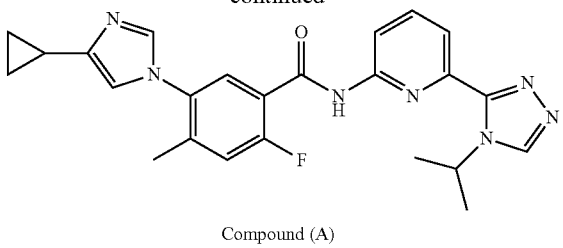

Compound (A)

Compound (C) was synthesized as described in U.S. Pat. No. 8,742,126, which is hereby incorporated by reference in its entirety.

To a solution of Compound (B) (about 1 equiv in about 12 vols DCM) was charged diisopropylethyl amine (1.0 equiv) followed by Compound (C) (1.05 equiv). Upon reaction completion, 5% aqueous sodium hydroxide (about 5 vols) is added and the layers of the biphasic mixture are separated. A solution of 10% aqueous citric acid (about 2 vols) is charged to the organic layer and the layers of the biphasic mixture are separated. Water (about 5 vols) is charged to the organic layer and the layers of the biphasic mixture are separated. The organic solution is filtered, and the solution is solvent swapped to about 15% DCM in EtOH under vacuum at about 45° C. The mixture is seeded with about 0.001 equiv of Compound (A), which was synthesized as described by U.S. Pat. No. 8,742,126, and the resultant slurry is aged at about 45° C. An additional 2-3 vols solvent is distilled in vacuo and then heptane (about 10 vols) is charged slowly and the slurry is aged, cooled to about 20° C., filtered and washed with 1:2 EtOH:heptane (about 3 vols). The solids are dried under vacuum at about 40° C. to afford Compound (A). Characterization data for Compound (A) matches that disclosed in U.S. Pat. No. 8,742,126.

Alternative reagents and reaction conditions to those disclosed above may also be employed. For example, alternative bases may be used, including but not limited to Et$_3$N, pyridine, and DMAP. Various solvents, such as 2-MeTHF, toluene, MTBE, and chloroform, may be employed. The reaction may take place at temperatures that range from about 0° C. to about 40° C.

In lieu of Compound (B), Compound (D) or activated esters thereof may be employed. Coupling reagents may also be employed; non-limiting examples of such reagents include propane phosphonic acid anhydride (T3P®), 1,1'-carbonyldiimidazole, EDC/HOBt or other imide coupling reagents, isobutylchloroformate (to generate an isobutyl ester), and pivoyl chloride (to generate a pivalate ester).

Example 2: Alternative Synthesis of Compound (D)

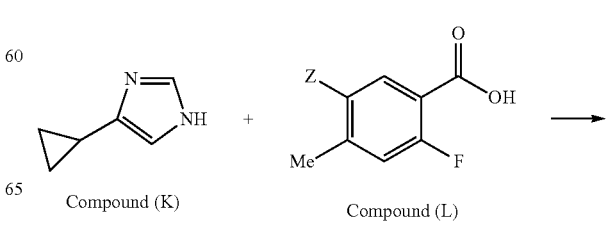

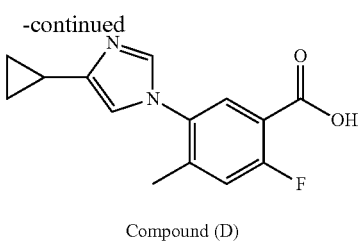

Compound (D)

Coupling of Compound (K) and Compound (L-a) to provide Compound (D)

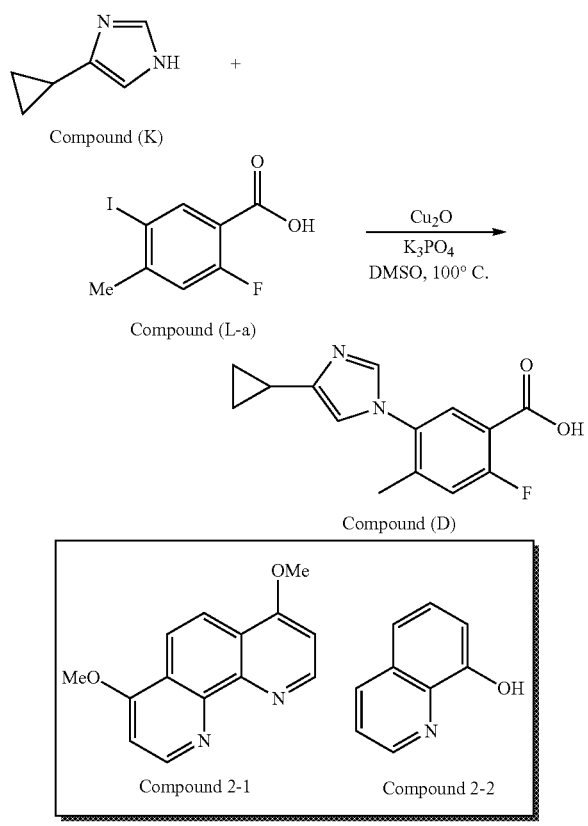

Compound (L-a) (1.0 eq), Compound (K) (1.5 eq), potassium phosphate (5.0 eq), copper (I) oxide (0.05 eq), and 8-hydroxyquinoline, Compound 2-2 (0.2 eq) were combined with degassed DMSO (about 6 vols). The reaction mixture was heated to about 95° C. to about 105° C. and stirred for about 22 h. Upon reaction completion, the mixture was cooled to ambient temperature and diluted with water (about 6 vols) and isopropyl acetate (about 5 vols). The aqueous layer was washed with isopropyl acetate (about 5 vols), and the pH was adjusted to about 6 by the addition of 8 M HCl. The solution was seeded with about about 0.003 equiv of Compound (D) seed, which was synthesized as described in U.S. Pat. No. 8,742,126, and the pH was further adjusted to pH about 4.8. The resultant slurry was cooled to about 0° C. for about 2 h, filtered, and washed with cold dilute HCl (pH about 4.8, about 2 vols) and cold isopropyl alcohol (about 2 vols) to provide Compound (D). $^1$H NMR (400 MHz, DMSO-$d_6$): δ 7.69 (d, 1H, J=2.0 Hz), 7.67 (d, 1H, J=8.0 Hz), 7.40 (d, 1H, J=8.0 Hz), 7.15 (d, 1H, J=2.0 Hz), 2.20 (s, 3H), 1.87-1.80 (m, 1H), 0.81-0.77 (m, 2H), 0.71-0.67 (m, 2H). $^{13}$C NMR (100 MHz, DMSO-$d_6$): 164.52, 164.48, 161.68, 159.12, 143.95, 141.63, 141.53, 137.34, 133.21, 133.18, 129.70, 119.85, 119.61, 118.08, 117.97, 116.25, 18.02, 9.21, 7.48.

Alternative reagents and reaction conditions to those disclosed above may also be employed. For example, alternative bases may be used, including but not limited to carbonate bases (such as $Cs_2CO_3$, $K_2CO_3$, and $Na_2CO_3$). In lieu of $Cu_2O$, alternative catalysts may be used, such as CuOAc, CuI, CuBr, and [(CuOTf)$_2$-benzene complex]. Non-limiting examples of alternative ligands include phenanthroline ligands (such as 4,7-dimethoxy-1,10-phenanthroline (Compound 2-1) and 1,10-phenanthroline), aminoarenethiols (such as 2-((dimethylamino)methyl)benzenethiol), oxime-phospine oxides, phosphoramidites, 2-aminopyrimidine diols (such as 2-aminopyrimidine-4,6-diol), and oxime-phosphine oxides (such as 2-hydroxybenzaldehyde oxime). In some embodiments, additives may be used, including but not limited to polyethyleneglycol and/or water, $Et_4NHCO_3$, and cetryltrimethylammonium bromide.

In lieu of Compound (L-a), alternative starting material can be used, including but not limited to 5-bromo-2-fluoro-4-methylbenzoic acid, 2-fluoro-4-methyl-5-(((trifluoromethyl)sulfonyl)oxy)benzoic acid, and 2-fluoro-4-methyl-5-(tosyloxy)benzoic acid. Additionally, in lieu of the free base of Compound (K), various salts of Compound (K) may be used, such as the besylate salt.

Various solvents may be used, including but not limited to DMF, DMAc, DMSO, butyronitrile, xylenes, EtCN, dioxane, and toluene. The reaction may take place at temperatures that range from about 80° C. to about 150° C.

Coupling of Compound (L-b) with Compound (K) to Provide Compound (D)

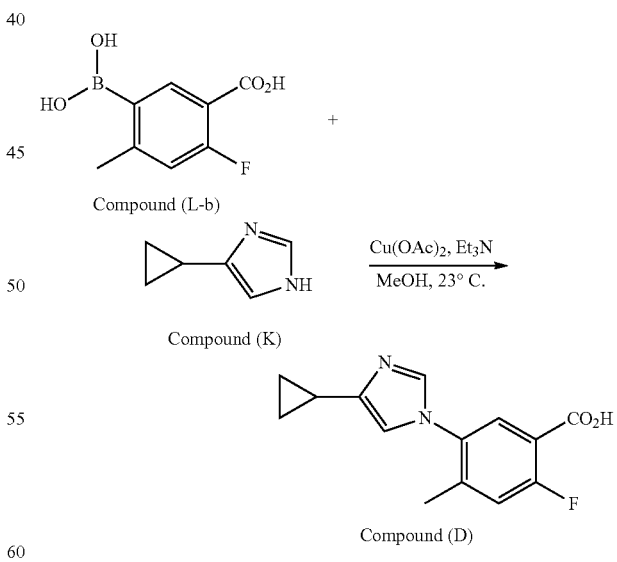

Compound (L-b) (1 equiv), Compound (K) (1.2 equiv), and $Cu(OAc)_2$ (1 equiv) was added methanol (about 20 vols) followed by pyridine (2.2 equiv). The mixture was then stirred at about 23° C. for about 16 h, then at about 45° C. for about 4 h. The reaction mixture was diluted with methanol (about 60 vols), filtered though a pad of celite and concentrated in vacuo to afford Compound (D). ¹H NMR (400 MHz, DMSO-d₆): δ 7.69 (d, 1H, J=2.0 Hz), 7.67 (d, 1H, J=8.0 Hz), 7.40 (d, 1H, J=8.0 Hz), 7.15 (d, 1H, J=2.0 Hz), 2.20 (s, 3H), 1.87-1.80 (m, 1H), 0.81-0.77 (m, 2H), 0.71-0.67 (m, 2H). ¹³C NMR (100 MHz, DMSO-d₆): 164.52, 164.48, 161.68, 159.12, 143.95, 141.63, 141.53, 137.34, 133.21, 133.18, 129.70, 119.85, 119.61, 118.08, 117.97, 116.25, 18.02, 9.21, 7.48.

Alternative reagents and reaction conditions to those disclosed above may also be employed. For example, in lieu of Compound (L-b), 2-fluoro-4-methyl-5-(4,4,5,5-tetramethyl-1,3,2-dioxaborolan-2-yl)benzoic acid may be used. In lieu of Compound (K), the besylate salt of Compound (K) may be used.

Various copper reagents can be employed, such as Cu(OTf)₂, Cu₂O, and CuBr. Alternative bases include but are not limited to triethylamine and N,N-diisopropylethylamine. Various solvents, such as DCM and DMF, may be employed. The reaction may take place at temperatures that range from about 23° C. to about 100° C. and under an atmosphere of oxygen or nitrogen.

Example 3: Alternative Synthesis of Compound (C)

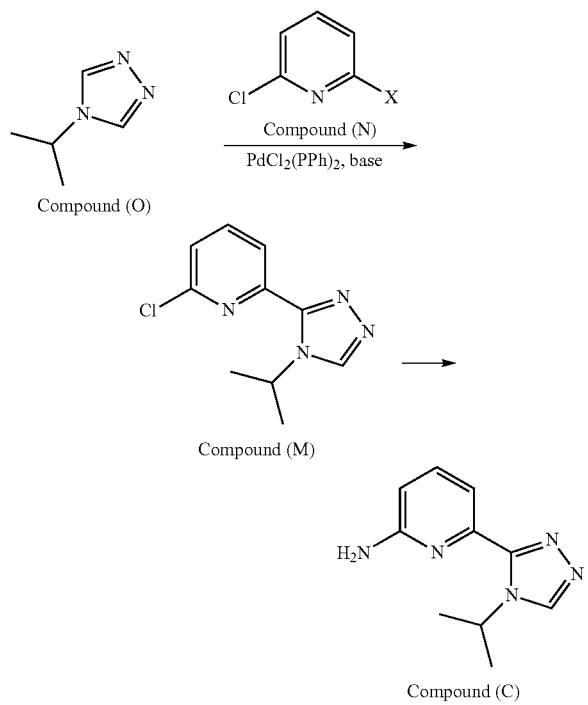

Coupling of Compound (O) with Compound (N-a) to Form Compound (M)

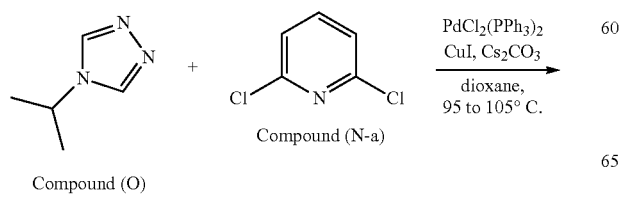

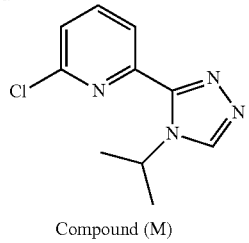

Compound (M)

To a mixture of Compound (O) (1.0 equiv), Compound (N-a) (1.6 equiv), PdCl₂(PPh₃)₂ (65 mol %), Cs₂CO₃ (2.0 equiv), and CuI (4.7 mol %) was charged dioxane (10 mL). The mixture was degassed and then heated to about 95° C. to about 105° C. After a period of about 20 hours, the mixture was cooled to ambient temperature. The reaction mixture was diluted with EtOAc (about 10 vols), washed with water (about 10 vols) and the layers of the biphasic mixture were separated. The organic layer was dried over MgSO₄ and concentrated in vacuo. The crude residue was purified by silica gel chromatography to afford Compound (M). ¹H NMR (400 MHz, DMSO-d₆): δ 8.95 (s, 1H), 8.16-8.04 (m, 2H), 7.67 (d, 1H, J=8.4 Hz), 5.34 (sep, 1H, J=6.6 Hz), 1.50 (d, 6H, 6.6 Hz). ¹³C NMR (100 MHz, DMSO-d₆): 149.90, 149.58, 148.36, 144.11, 141.62, 125.27, 122.92, 48.91, 23.42.

Alternative reagents and reaction conditions to those disclosed above may also be employed. For example, alternative catalysts may be other Pd (II) complexes or Pd(0) complexes with trialkyl or triarylphosphine ligands, including but not limited to: Pd(PPh₃)₄, Pd₂dba₃/PPh₃, Pd(OAc)₂/dppf, Pd₂dba₃/dppp, Pd(OAc)₂/PPh₃, Pd(OAc)₂/dppe, Pd₂dba₃/dppf. Various bases may be used, such as a carbonate base (e.g. K₂CO₃ or Na₂CO₃). Various solvents, such as DMF, DMAc, DMSO, butyronitrile, and NMP, may be employed. The reaction may take place at temperatures that range from about 80° C. to about 150° C.

Conversion of Compound (M) to Form Compound (C)

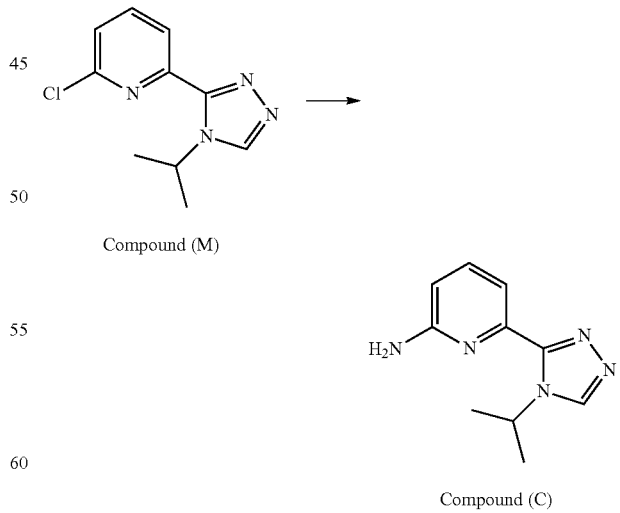

To a mixture of Compound (M) (1.0 equiv), Pd(OAc)₂ (2.0 mol %), rac-BINAP (3.0 mol %), and Cs₂CO₃ (1.4 equiv), was charged dioxane (about 9 vols) followed by benzophenone imine (2.0 equiv). The mixture was degassed, sealed and then heated to about 75° C. to about 85° C. under nitrogen. After a period of about 20 hours, the mixture was cooled to ambient temperature, and HCl (6 M, about 8 vols) was charged until the pH of the reaction mixture was about 1 to about 2. The solution was maintained at ambient temperature for about 15 minutes, then NaOH (30 wt. %, about 1 to about 2 vols) was charged until the pH of the reaction mixture was about 8-9. The reaction mixture was concentrated in vacuo, slurried in MeOH (about 22 vols), and filtered to remove gross solids, which were washed with MeOH (2× about 3 vols). The resulting solution was concentrated in vacuo, adsorbed onto celite and purified by silica gel chromatography to provide compound (C). LRMS [M+H]$^+$: 204.08.

Alternative reagents and reaction conditions to those disclosed above may also be employed. For example, alternative catalysts may be other Pd (II) complexes or Pd(0) complexes with trialkyl or triarylphosphine ligands, including but not limited to: Pd(PPh$_3$)$_4$, Pd$_2$dba$_3$/PPh$_3$, Pd(OAc)$_2$/dppf, Pd$_2$dba$_3$/dppp, Pd(OAc)$_2$/PPh$_3$, Pd(OAc)$_2$/dppe, Pd$_2$dba$_3$/dppf, Pd$_2$dba$_3$/CyJohnPhos, Pd$_2$dba$_3$/P(t-Bu)$_3$. Various ammonia sources may be used such as LiHMDS or ammonium hydroxide. Various carbonate bases (e.g. K$_2$CO$_3$ or Na$_2$CO$_3$) or phosphate bases such as K$_3$PO$_4$ may be used. Various solvents, such as THF, DMAc, DMSO, and NMP, may be employed. The reaction may take place at temperatures that range from about 75° C. to about 150° C. and pressures ranging from about 15 to about 50 psig.

Example 4: Alternative Synthesis of Compound (C)

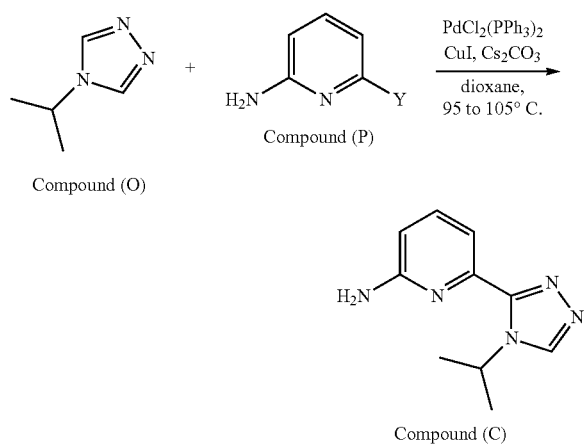

Coupling of Compound (O) with Compound (P-a) to Form Compound (C)

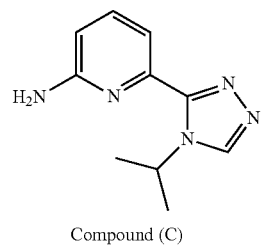

Compound (C)

To a mixture of Compound (O) (1.0 equiv), Compound (P-a) (1.0 equiv), PdCl$_2$(PPh$_3$)$_2$ (10 mol %), Cs$_2$CO$_3$ (2.0 equiv), and CuI (4.7 mol %) was charged dioxane (about 20 vols). The mixture was degassed and then heated to about 95° C. to about 105° C. After a period of about 20 to about 40 hours, the mixture was cooled to ambient temperature. The reaction mixture was diluted with EtOAc (about 40 vols) and the organic layer was washed with water (about 40 vols). The layers of the biphasic mixture were separated and the aqueous phase was extracted with EtOAc (about 40 vols). The combined organic phases were concentrated in vacuo. To the residue was charged IPA (about 20 vols), and the resulting suspension was stirred at about 40° C. to about 50° C. for about 1 h and then stirred at ambient temperature for about 16 h. The suspension was cooled to about 5° C., filtered and washed with cold IPA (about 4 vols). The resulting solids were dried at about 40° C. to afford Compound (C). $^1$H NMR (400 MHz, DMSO-d$_6$): δ 8.77 (s, 1H), 7.51 (t, 1H, J=8.0 Hz), 7.18 (d, 1H, J=4.0 Hz), 6.53 (d, 1H, J=8.0 Hz), 6.17 (s, 1H), 5.53 (sep, 1H, J=8.0 Hz), 1.42 (d, 6H, J=8.0 Hz). $^{13}$C NMR (100 MHz, DMSO-d$_6$): 159.59, 151.18, 146.25, 142.97, 138.41, 111.90, 108.88, 48.12, 23.55.

Alternative reagents and reaction conditions to those disclosed above may also be employed. For example, alternative catalysts may be other Pd (II) complexes or Pd(0) complexes with trialkyl or triarylphosphine ligands, including but not limited to: Pd(PPh$_3$)$_4$, Pd$_2$dba$_3$/PPh$_3$, Pd(OAc)$_2$/dppf, Pd$_2$dba$_3$/dppp; Pd(OAc)$_2$/PPh$_3$; Pd(OAc)$_2$/dppe; Pd$_2$dba$_3$/dppf, Pd(OAc)$_2$/(m-tolyl)$_3$P, Pd(OAc)$_2$/JohnPhos; PdCl$_2$dppf, Pd(OAc)$_2$/(o-tolyl)$_3$P; PdCl$_2$(AmPhos)$_2$; Pd(OAc)$_2$/(cyclohexanlyl)$_3$P. Various bases may be used, such as a carbonate base (e.g. K$_2$CO$_3$ or Na$_2$CO$_3$). Various solvents, such as DMF, DMAc, DMSO, butyronitrile, and NMP, may be employed. The reaction may take place at temperatures that range from about 80° C. to about 150° C.

Coupling of Compound (O) with Compound (P-b) to form Compound (C)

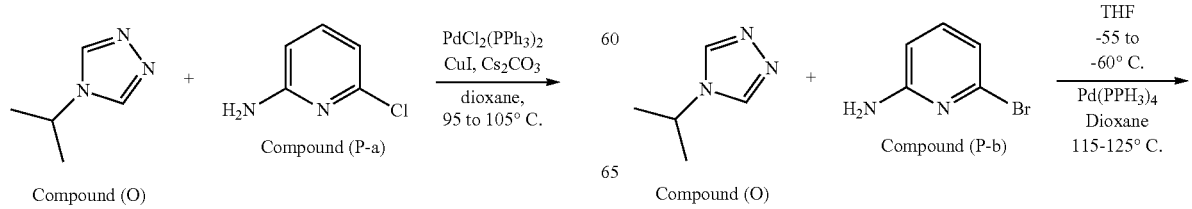

-continued

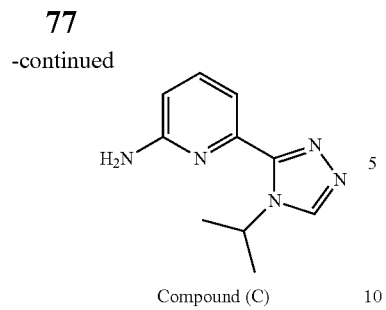

Compound (C)

A solution of Compound (O) (1.0 equiv) in THF (about 20 vols) was degassed with nitrogen. The solution was cooled to about −55° C. to about −70° C. and a solution of n-BuLi (1.6 M solution in hexane, 1.0 equiv) was added over about 15 to about 20 minutes. The suspension was stirred for about 15 to about 25 minutes at about −55° C. to about −60° C., followed by the slow addition of ZnCl$_2$ (0.5 M solution in THF, 1 equiv). The suspension was stirred for about 30 minutes and warmed to ambient temperature. To a separate flask was charged Compound (P-b) (1.0 equiv) and Pd(PPh$_3$)$_4$ (231 mg, 4.4 mol %) in dioxane (about 20 vols). The mixture was degassed and transferred to the flask containing the organozinc intermediate. The mixture was sealed and heated to about 115° C. to about 125° C. for about 15 hours then cooled to ambient temperature. The reaction mixture was concentrated in vacuo at ambient temperature and triturated with MTBE (about 10 mL) to afford Compound (C). $^1$H NMR (400 MHz, DMSO-d$_6$): δ 8.77 (s, 1H), 7.51 (t, 1H, J=8.0 Hz), 7.18 (d, 1H, J=4.0 Hz), 6.53 (d, 1H, J=8.0 Hz), 6.17 (s, 1H), 5.53 (sep, 1H, J=8.0 Hz), 1.42 (d, 6H, J=8.0 Hz). $^{13}$C NMR (100 MHz, DMSO-d$_6$): 159.59, 151.18, 146.25, 142.97, 138.41, 111.90, 108.88, 48.12, 23.55.

Alternative reagents and reaction conditions to those disclosed above may also be employed. For example, for the metallation, in lieu of n-BuLi, other organolithium reagents (such as t-BuLi, MeLi, and s-BuLi) or Grignard reagents (such as iPrMgCl and PhMgCl) may be used. In lieu of 1 equivalent of ZnCl$_2$, 0.5 equivalent of ZnCl$_2$ or ZnCl$_2$ with LiCl, ZnBr$_2$, or ZnI$_2$ can be used. Alternative solvents to THF can include 2-MeTHF, MTBE, or Et$_2$O, and this reaction may take place at temperatures that range from about −78° C. to about −40° C.

Additionally, during the coupling reaction, alternative catalysts may be other Pd (II) complexes or Pd(0) complexes with trialkyl or triarylphosphine ligands, such as Pd(PPh$_3$)$_4$. Various solvents, such as NMP, THF, butyronitrile, and toluene, may be employed. The reaction may take place at temperatures that range from about 80° C. to about 140° C.

Example 5: Alternative Synthesis for Compound (D)

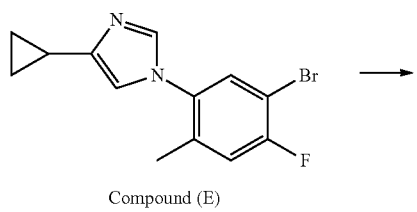

Compound (E)

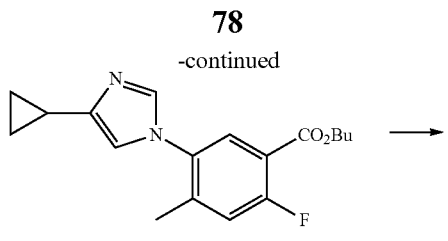

Compound (Q)

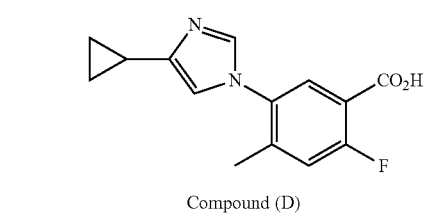

Compound (D)

Carboalkoxylation to Form Compound (Q)

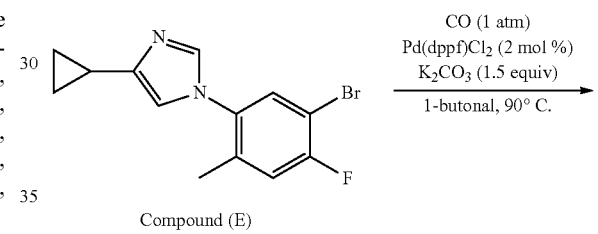

Compound (E)

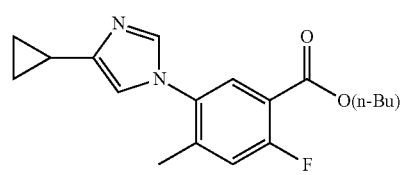

Compound (Q)

To a reaction flask was added 1-butanol (7 volumes). Compound (E) (1 equiv) was added followed by K$_2$CO$_3$ (1.5 equiv) and Pd(dppf)Cl$_2$ (0.02 equiv) and the reaction was placed under a CO atmostphere. The reaction mixture was heated at about 90° C. until reaction completion. The reaction contents were cooled to ambient temperature, the reaction mixture was filtered through a pad of Celite to remove solids, and then rinsed forward with EtOAc. The mother liquor was washed with water and brine, and dried over Na$_2$SO$_4$, filtered, and concentrated to afford Compound (Q). Purification by flash chromatography afforded Compound (Q): $^1$H NMR (400 MHz, CDCl$_3$) δ 7.77 (d, J=6.7 Hz, 1H), 7.39 (s, 1H), 7.08 (d, J=10.8 Hz, 1H), 6.74 (s, 1H), 4.31 (t, J=6.6 Hz, 2H), 2.20 (s, 3H), 1.87 (m, 1H), 1.73 (tt, J=6.7, 6.6 Hz, 3H), 1.43 (tq, J=7.3, 7.4 Hz), 0.94 (t, J=7.4 Hz, 3H), 0.88

(m, 2H), 0.79 (m, 2H); Exact mass for $C_{18}H_{22}N_2O_2F$ [M+H], 317.2. Found [M+H], 317.

Alternative reagents and reaction conditions to those disclosed above may also be employed. For example, alternative catalysts may be used. Non-limiting examples include other Pd (II) complexes or Pd(0) complexes with trialkyl or triarylphosphine ligands, such as $PdCl_2(dppf)$ or $Pd(OAc)_2$ with $PPh_3$, xantphos, $tBu_3P$-$HBF_4$, dppe, dppb, dpcb, tBu-dppf, and $(Ad)_2P(nBu)$. Alternative bases can be used, such as other carbonate bases (such as $Cs_2CO_3$, and $Na_2CO_3$), NaOAc, KOAc, or organic bases such as TMEDA, $Et_3N$, and $iPr_2NEt$. Various solvents may be employed, such as 1-butanol with other co-solvents (e.g. DMF). The reaction may take place at temperatures that range from about 70° C. to about 115° C. and at CO pressures of about 5 to about 50 psig.

Hydrolysis of Compound (Q) to Compound (D)

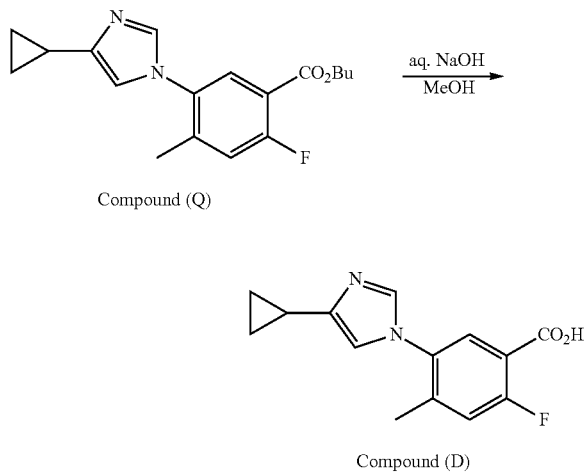

Compound (Q)

Compound (D)

To a reaction flask was added Compound (Q) (1.0 equiv) and MeOH (7 volumes). A 25% NaOH solution (5 equiv) was then added dropwise. Consumption of Compound (D) was observed after about 1.5 hours at which point the pH of the solution was carefully adjusted to about 1 by the addition of 6 N HCl. Methanol was removed under vacuum to afford a solid which was isolated by filtration. The crude product was first triturated in THF and then filtered. This solid was then triturated in $CH_2Cl_2$/MeOH (9:1) and filtered. Concentration of the mother liquor afforded Compound (D). $^1H$ NMR (400 MHz, $CD_3OD$) δ 8.87 (s, 1H), 7.94 (d, J=6.6 Hz, 1H), 7.43 (s, 1H), 7.31 (d, J=11.5 Hz, 1H), 2.21 (s, 3H), 1.96 (m, 1H), 1.04 (m, 2H), 0.81 (m, 2H); LRMS: Calculated mass for $C_{14}H_{14}N_2O_2F$ [M+H], 261.1. Found [M+H], 261.

Alternative reagents and reaction conditions to those disclosed above may also be employed. For example, an alternative hydroxide base, including but not limited to KOH, LiOH, and CsOH, may be used in lieu of NaOH. Various solvents may be employed, such as THF, EtOH, and 2-propanol. The reaction may take place at temperatures that range from about 0° C. to about 50° C.

Example 6: Alternative Synthesis of Compound (A)

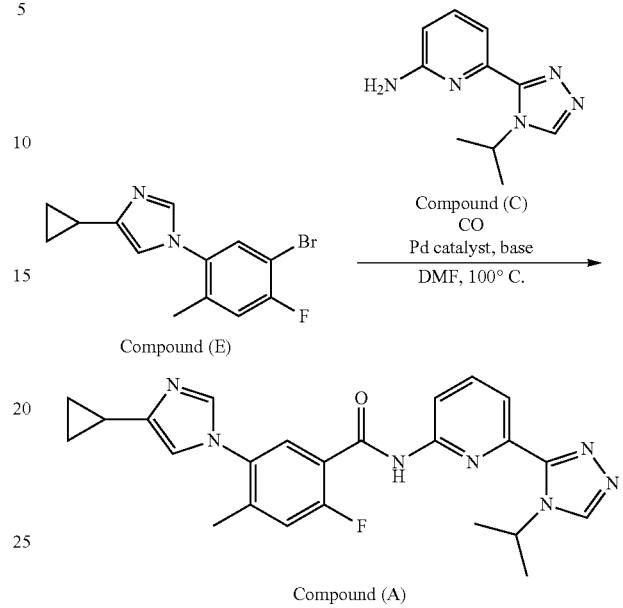

Compound (E)

Compound (A)

Compound (E) (1 equiv.), Compound (C) (1 equiv.), DMF (about 16 vols), $Et_3N$ (1.5 equiv.), $Pd(OAc)_2$ (0.02 equiv.), and $Ad_2P(n-Bu)$ (0.04 equiv.) were combined and the contents were purged with $N_2$ followed by CO and then pressurized with CO (20 psi). The reaction mixture was heated to about 95° C. to about 105° C. After about 24 hours, the reaction was allowed to cool to about 20° C. to about 30° C. to afford Compound (A).

Alternative reagents and reaction conditions to those disclosed above may also be employed. For example, alternative catalysts may be used. Non-limiting examples include other Pd (II) complexes or Pd(0) complexes with trialkyl or triarylphosphine ligands, such as $PdCl_2(PPh_3)_2$, $PdCl_2(A$-$Phos)_2$ or $Pd(OAc)_2$ with $PPh_3$. Alternative bases can be used, including but not limited to other organic bases (such as $iPr_2NEt$ and TMEDA) and inorganic bases (such as NaOAc, KOAc, $Na_2CO_3$, and $Cs_2CO_3$). Various solvents, NMP, dioxane, and toluene, may be employed. The reaction may take place at temperatures that range from about 90° C. to about 120° C. and at CO pressures of about 20 psig to about 60 psig.

Example 7: Alternative Synthesis of Compound (A)

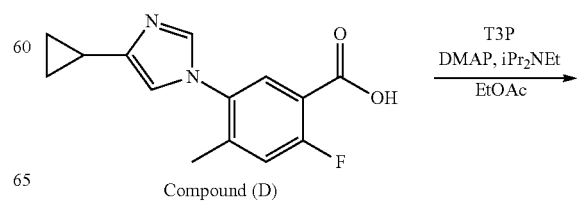

Compound (D)

-continued

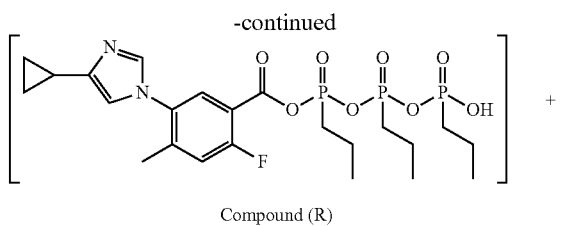

Compound (R)

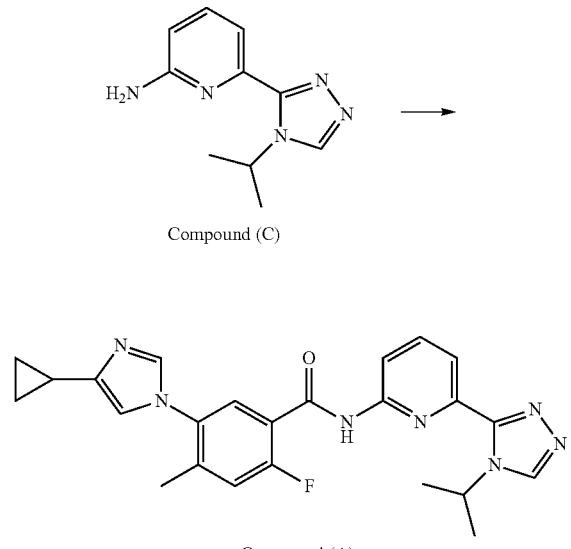

Compound (C)

Compound (A)

Compound (D) (1.0 equiv), Compound (C) (1.05 equiv), 4-(dimethylamino)pyridine (1.0 equiv), ethyl acetate (about 4 V) and diisopropylethylamine (1.2 equiv) were combined and the resulting slurry was charged T3P® as a 50 wt % solution in ethyl acetate (2.0 equiv) over about 3 min at about 20° C. During the addition, a small exotherm was observed. The mixture was stirred at about 20° C. for about 24 h. After reaction completion, 0.5 M aqueous hydrochloric acid (about 5 vols was added, and the mixture was stirred for about 15 min. Stirring was then stopped, and the phases were allowed to separate. Then, the aqueous phase was reintroduced to the reactor. The pH of the aqueous solution was then adjusted to about 7 with a 5 wt % solution of aqueous sodium hydroxide (about 12 vols). The resulting slurry was stirred for about 12 h at about 20° C. and then filtered, and the reactor was rinsed forward with water (about 3 vols). The filter cake was washed with isopropanol (2 vols), and the resulting solids were dried under vacuum at about 45° C. to provide Compound (A).

Alternative reagents and reaction conditions to those disclosed above may also be employed. For example, in lieu of T3P®, other coupling reagents may be used, including but not limited to 1,1'-carbonyldiimidazole, isobutyl chloroformate, pivoyl chloride, EDC-HCl/HOBt, thionyl chloride, and 4-(4,6-dimethoxy-1,3,5-triazin-2-yl)-4-methylmorpholinium chloride. Alternative bases may be used, including but not limited organic amines (such as trialkyl amine bases (for example, triethylamine), N-methyl morpholine, and the like) and carbonates (such as lithium carbonates, sodium carbonates, cesium carbonates, and the like). Various solvents, such as DCM, THF, DMF, ethyl acetate, MTBE, toluene, NMP, DMAc, acetonitrile, dichloroethane, 2-MeTHF, and cyclopentyl methyl ether, may be employed. The reaction may take place at temperatures that range from about −10° C. to about 60° C. or from about 0° C. to about 30° C.

Example 8: Alternative Synthesis of Compound (C)

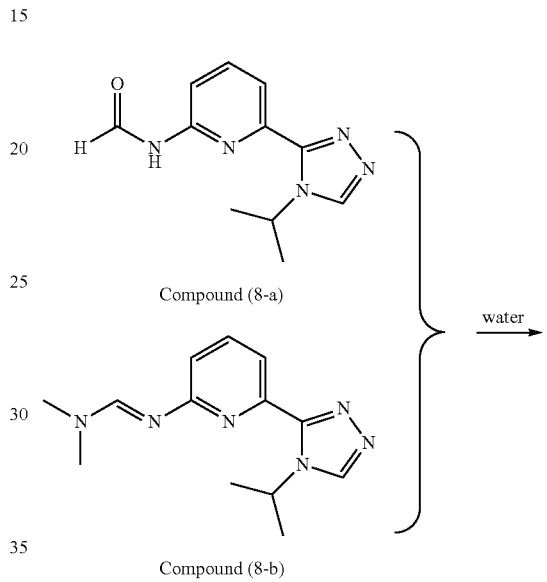

Compound (8-a)

Compound (8-b)

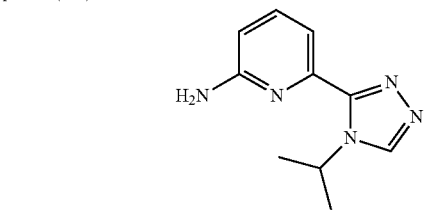

Compound (C)

The mixture of Compound (8-a) and Compound (8-b) is dissolved in about 10 volumes of process water. The solution is heated to about 80° C., and the solution is allowed to age for about 6 hours. Upon reaction completion, the solution is cooled to about 60° C. The reaction mixture is seeded with 0.001 equiv of Compound (C), which was obtained by suitable means, and cooled to about 0° C. Compound (C) is filtered from the cold aqueous solution to yield the product.

Alternative reagents and reaction conditions to those disclosed above may also be employed. For example, instead of the mixture of Compuond (8-a) and (8-b), the reaction may be carried out with Compound (8-a) or Compound (8-b). Additionally, other organic acids may be used, including but not limited to acetic acid and trifluoroacetic acid. Various solvents, such as toluene, dimethylacetamide, NMP, and 2-MeTHF, may be employed. The reaction may take place at temperatures that range from about 80° C. to about 110° C. or about 100° C.

Example 9: Alternative Synthesis of Compound (C)

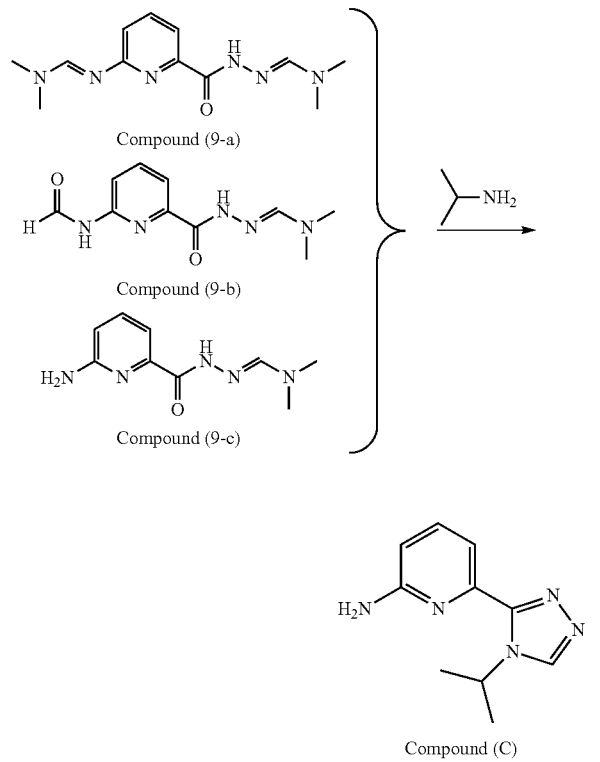

Compound (9-a)

Compound (9-b)

Compound (9-c)

Compound (C)

Compound (C) may be synthesized as described in U.S. Pat. No. 8,742,126, which is hereby incorporated by reference in its entirety. Additionally, when starting with Compound (9-a), it was found that Compound (C) may be formed through two additional intermediates, Compound (9-b) and Compound (9-c). LRMS for Compound (9-b): Calculated mass, $C_{14}H_{14}N_2O_2F$ [M+H], 235.1. Found [M+H], 235.9. LRMS for Compound (9-c): Calculated mass, $C_{14}H_{14}N_2O_2F$ [M+H], 207.1. Found [M+H], 208.

Alternative reagents and reaction conditions to those disclosed above may also be employed. For example, in lieu of acetic acid, other organic acids may be used, including but not limited to trifluoroacetic acid. Various solvents, such as toluene, dimethylacetamide, NMP, 2-MeTHF, acetic acid, and water, may be employed. The reaction may take place at temperatures that range from about 80° C. to about 110° C. or about 100° C.

Example 10: Alternative Synthesis of Compound (C)

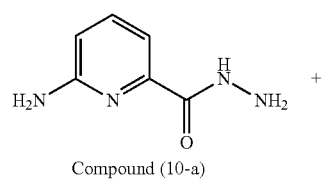

Compound (10-a)

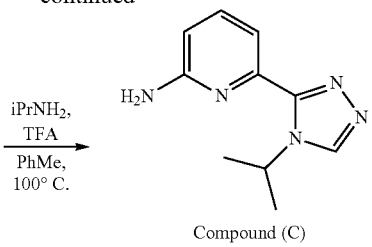

Compound (C)

Compound (10-a) (1 equiv), toluene (about 20 vols), N-isopropylformamide (3.00 equiv), isopropylamine (3.00 equiv) and trifluoroacetic acid (2.50 equiv) were sequentially combined. The vial was sealed and heated to about 100° C. After about 22 h, the vial was cooled to room temperature and the contents were analyzed by HPLC. Compound (C) was observed by HPLC.

Alternative reagents and reaction conditions to those disclosed above may also be employed. For example, other organic acids may be used, including but not limited to acetic acid. Various solvents, such as dimethylacetamide, NMP, and acetic acid, may be employed. The reaction may take place at temperatures that range from about 80° C. to about 110° C. or about 100° C.

Example 11: Alternative Synthesis of Compound (C)

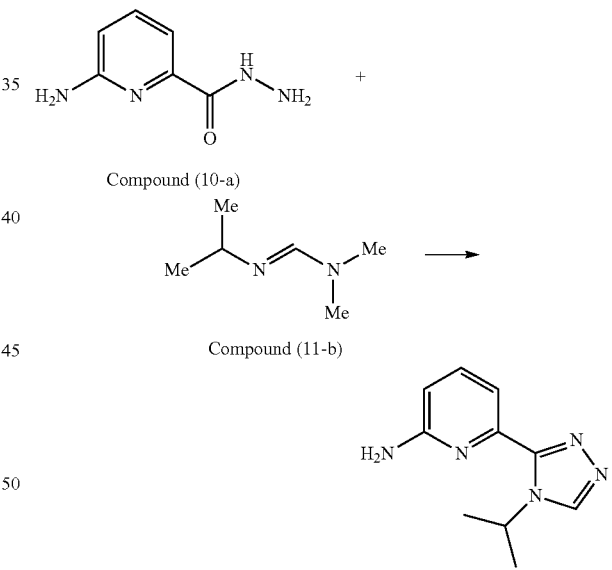

Compound (10-a)

Compound (11-b)

Compound (C)

Compound (10-a) (1.0 equiv), toluene (about 12 volumes), 79 wt % (E)-N-isopropyl-N,N-dimethylformimidamide (3.0 equiv), isopropylamine (3.0 equiv) and trifluoroacetic acid 2.5 equiv) were combined and heated to about 100° C. After about 22 h, the reaction mixture was cooled to room temperature. The mixture was seeded with Compound (C), which was obtained by suitable means, and cooled to about 0° C. After about 30 min, the heterogeneous mixture was filtered and the vial was rinsed forward with toluene (about 25 vols). The solid was collected and dried under vacuum at about 40° C. to provide Compound (C).

Alternative reagents and reaction conditions to those disclosed above may also be employed. For example, organic acids may be used, including but not limited to acetic acid. Various solvents, such as acetic acid, dimethylacetamide, and NMP, may be employed. Alternative organic amines may also be added. The reaction may take place at temperatures that range from about 80° C. to about 110° C. or about 90° C. to about 100° C.

Example 12: Alternative Synthesis of Compound (C)

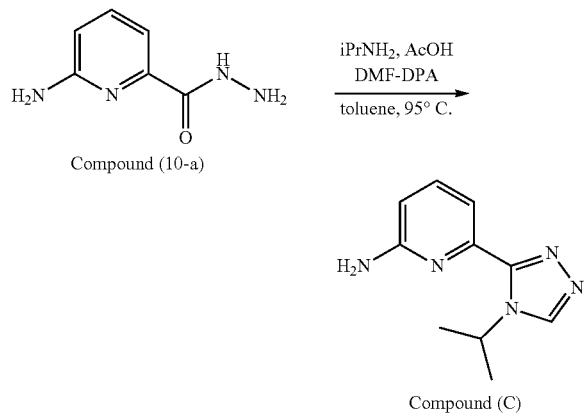

A suitable reactor fitted with a reflux condenser was charged with acyl hydrazide (1 equiv), toluene (6 volumes), isopropylamine (7.20 equiv) and N,N-dimethylformamide dipropyl acetal (2.70 equiv). To the resulting slurry was charged acetic acid (1.50 equiv) over about 2 min at about 20° C. During the addition, an exotherm was observed. The mixture was heated to about 95° C. for about 20 h. After reaction completion, the mixture was concentrated under vacuum at about 80° C. The mixture was diluted with water (10 volumes), and the resulting biphasic solution was concentrated under vacuum at about 80° C. Water was added (3 volumes), and the solution is heated to about 85° C. The resulting solution was cooled to about 60° C. and seeded with Compound (C), which was obtained by suitable means. The resulting slurry was aged for about 30 min and then cooled to about 20° C. over about 1 h and aged for about 15 h. The resulting slurry was cooled to about 5° C. and aged for about 3 h. The cold slurry is filtered and the reactor is rinsed forward with cold water (15 mL). The resulting solids were dried under vacuum at about 40° C. to give Compound (C).

Alternative reagents and reaction conditions to those disclosed above may also be employed. For example, alternative formamide reagents may be used, such as dimethyl formamide diethyl acetal, dimethyl formamide diisopropyl acetal, dimethyl formamide disec-butyl acetal, dimethyl formamide diisobutyl acetal, and the like. Other organic acids may be used, including but not limited to trifluoroacetic acid, chloroacetic acid, and methanesulfonic acid. Various solvents, such as acetic acid, dimethylacetamide, 2-MeTHF, NMP, isobutyl acetate, isobutanol, water, and isopropyl acetate, may be employed. The reaction may take place at temperatures that range from about 75° C. to about 110° C. or about 100° C.

Example 13: Forms of Compound (D)

Crystalline forms of Compound (D), and salts and hydates thereof, were analyzed by XRPD, DSC and TGA. XRPD patterns were collected with a PANalytical X'Pert PRO MPD diffractometer using mostly the following experimental setting: 45 kV, 40 mA, K$\alpha$1=1.5406 Å, scan range 2-40° 2θ, step size 0.0167° 2θ. The DSC analysis was conducted on a TA Instruments Q2000 differential scanning calorimeter using about 2 to about 3 mg of material, 10° C./min heating rate over the range of (−30° C.)-300° C. The TGA data were obtained on TA Instruments 2950 and Q5000 thermogravimetric analyzers using about 2 to about 5 mg of material, 10° C./min heating rate over the range of 25-350° C.

1.1 Compound of Formula (D-a) Form I

Figure 2:
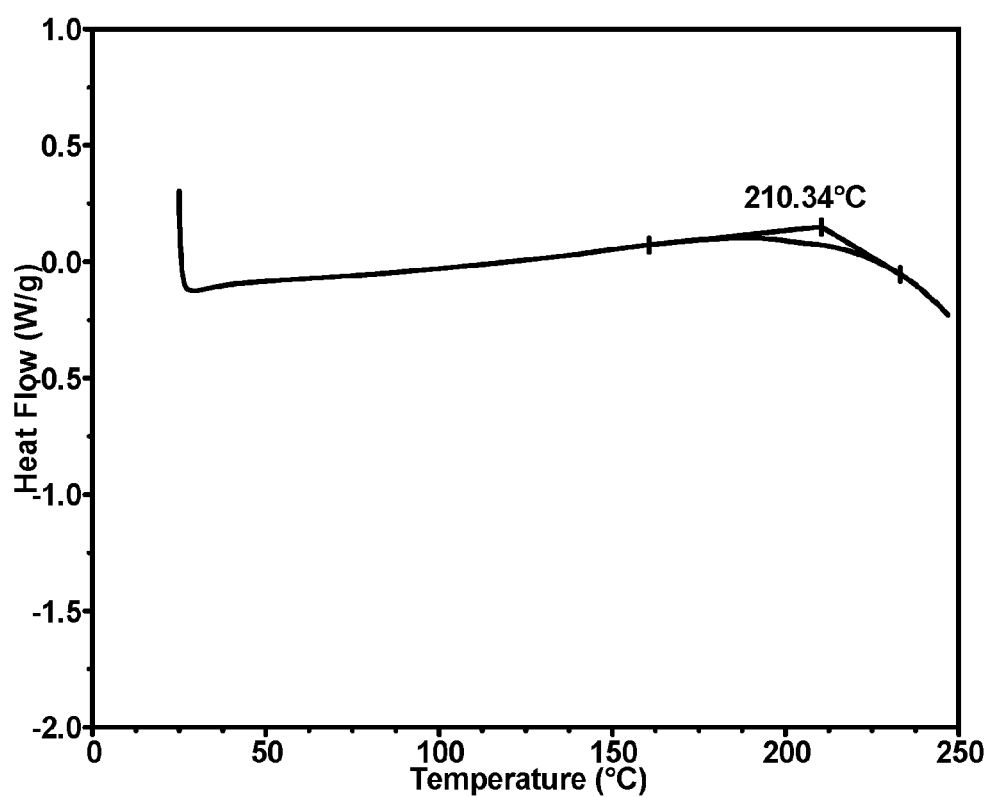
FIG. 2 shows a differential scanning calorimeter (DSC) curve of Compound of formula (D-a) Form I.
Figure 3:
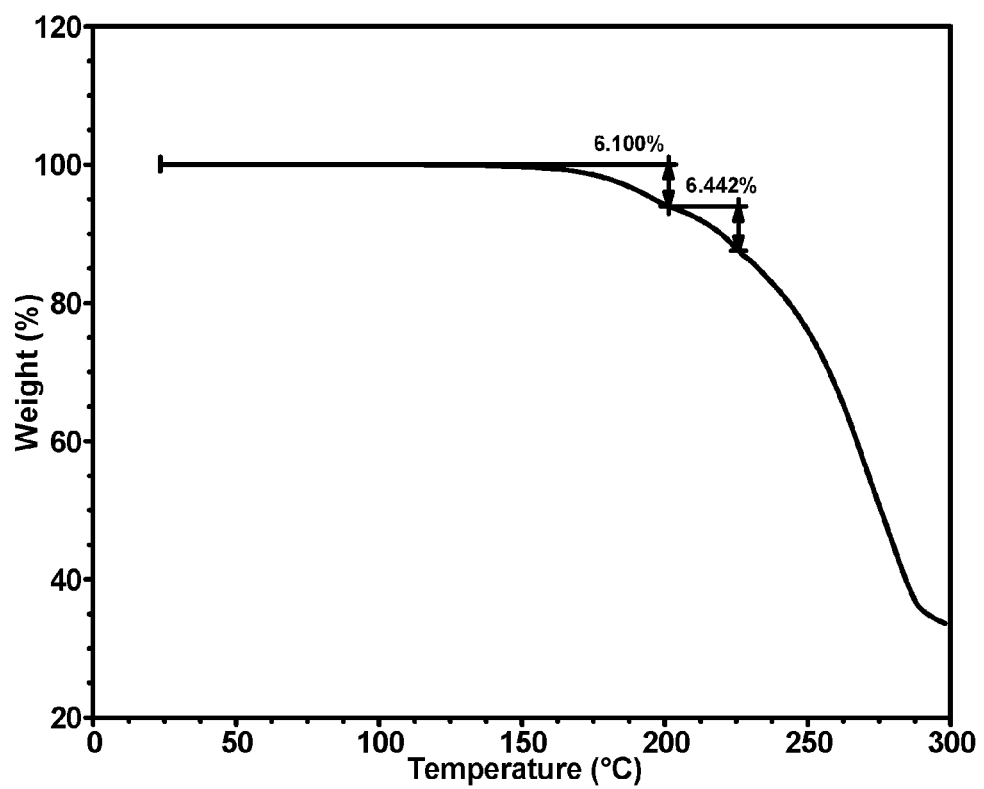
FIG. 3 shows a thermogravimetric analysis (TGA) of Compound of formula (D-a) Form I.

Compound of Formula (D-a) Form I is prepared as described in Example 1 and is an anhydrous crystalline form obtained from MeOH/MTBE (1:4) solvent system. Compound of Formula (D-a) Form I was characterized by XRPD, DSC and TGA. XRPD pattern is presented in FIG. 1. TGA did not show any weight loss below about 150° C., about 6% weight loss was observed at about 150 to about 200° C., and about 6.4% weight loss at about 200 to about 240° C., followed by decomposition (FIG. 3). This weight loss could correspond to the loss of HCl (1 equivalent HCl=12.3%). DSC thermogram showed possible endotherm with onset at about 210° C. (FIG. 2). Compound of Formula (D-a) Form I is a kinetic form, which eventually converts to thermodynamically more stable Compound of Formula (D-a) Form II after the slurry equilibration.

1.2 Compound of Formula (D-a) Form II

Compound of Formula (D-a) Form II is prepared as described in Example 1 and is an anhydrous crystalline form obtained from MeOH/MTBE (1:4) solvent mixture after about 15 hrs equilibration. Compound of Formula (D-a) Form II was characterized by XRPD, DSC and TGA.

Figure 4:
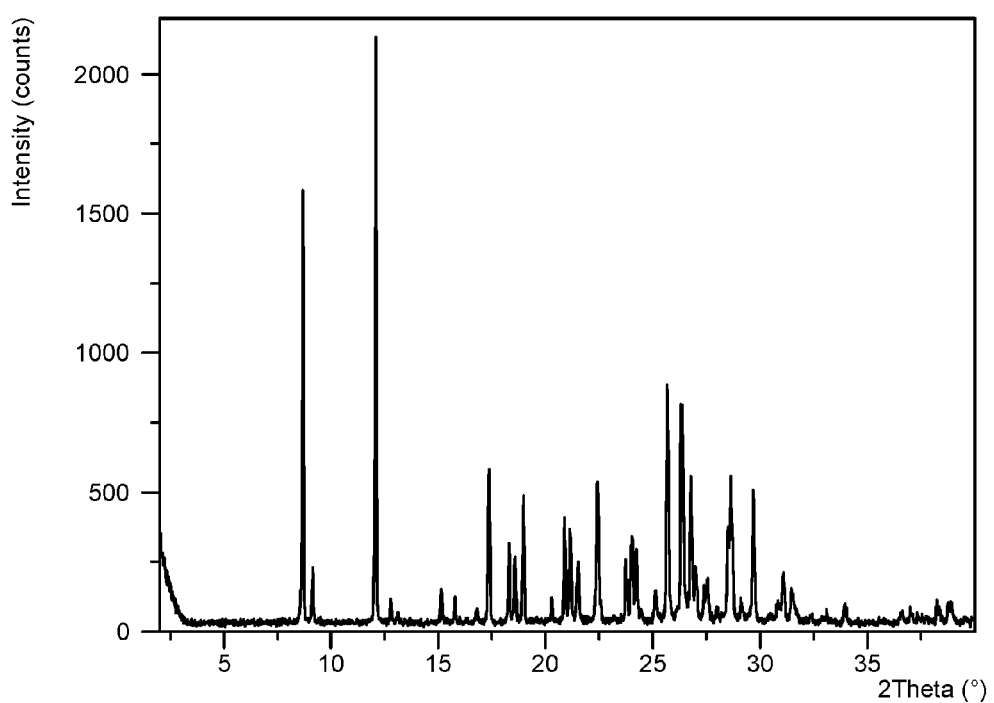
FIG. 4 shows an X-ray powder diffraction (XRPD) of Compound of formula (D-a) Form II.
Figure 5:
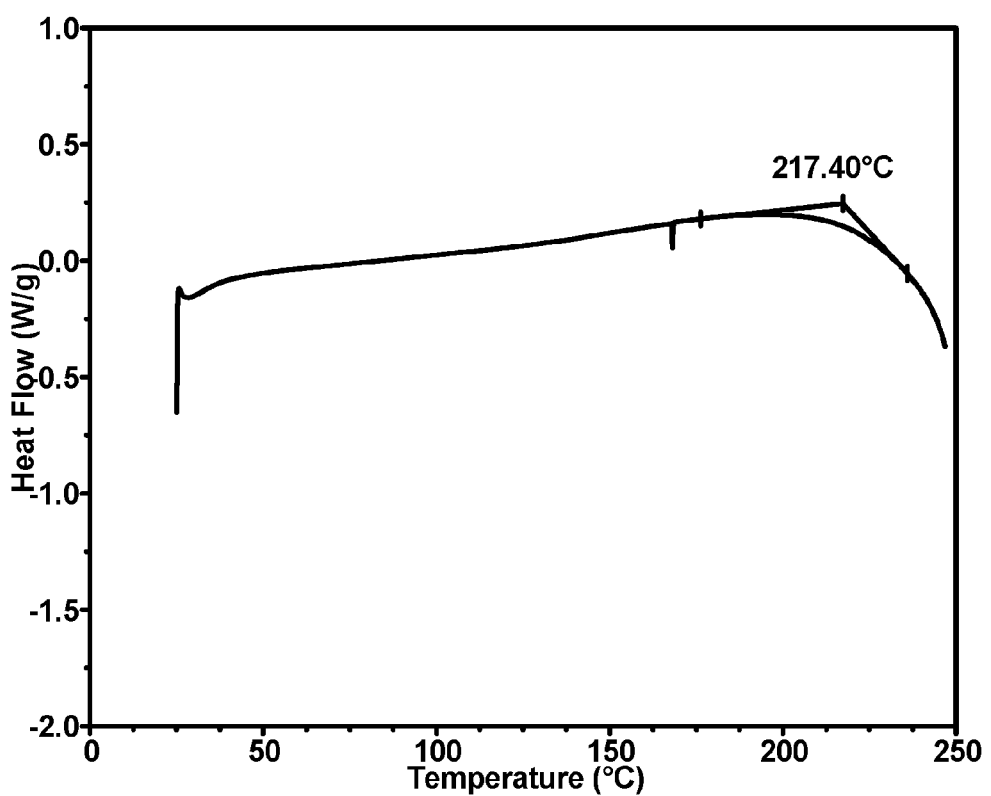
FIG. 5 shows a differential scanning calorimeter (DSC) curve of Compound of formula (D-a) Form II.
Figure 6:
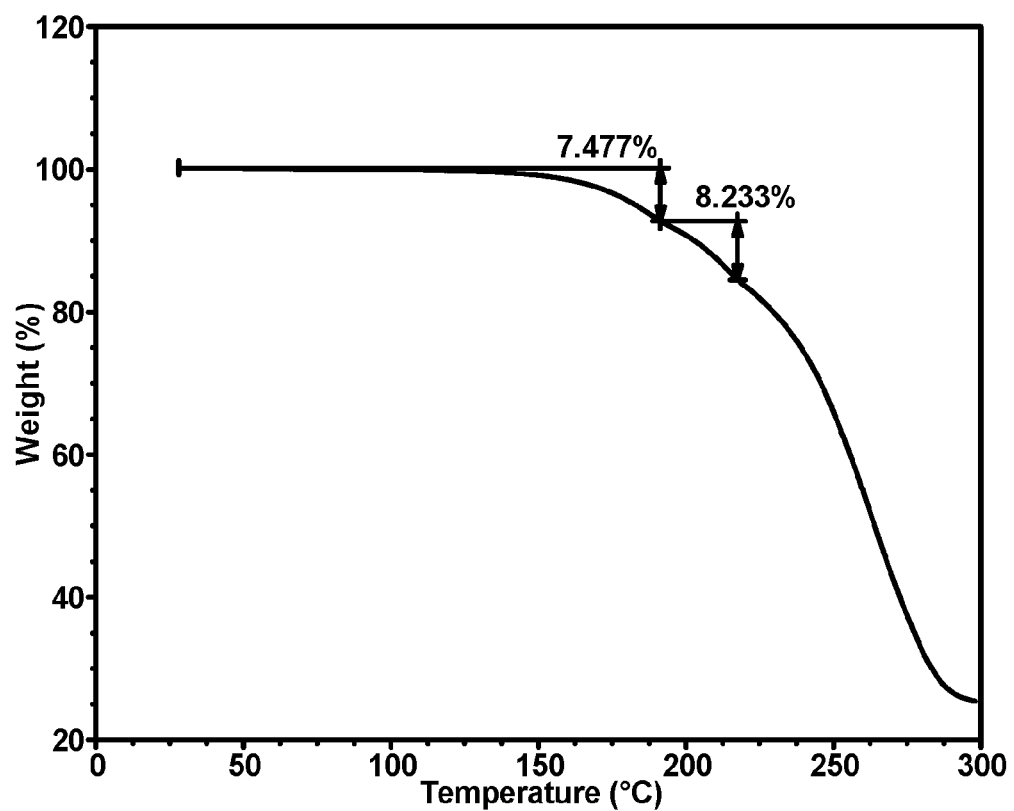
FIG. 6 shows a thermogravimetric analysis (TGA) of Compound of formula (D-a) Form II.

XRPD pattern is presented in FIG. 4. TGA did not show any weight loss below about 150° C., about 7.5% weight loss was observed at about 150 to about 190° C. and about 8.2% weight loss at about 190 to about 220° C. most likely corresponding to the loss of HCl (slightly more than 1 equivalent), followed by decomposition (FIG. 6). DSC thermogram showed possible endotherm with onset at about 217° C. (FIG. 5). Compound of Formula (D-a) Form II is a thermodynamically more stable form than Compound of Formula (D-a) Form I, which was confirmed by competitive slurry experiments in MeOH and in MeOH/MTBE (1:4) at room temperature.

2.1 Compound of Formula (D) Hydrate Form I

Figure 7:
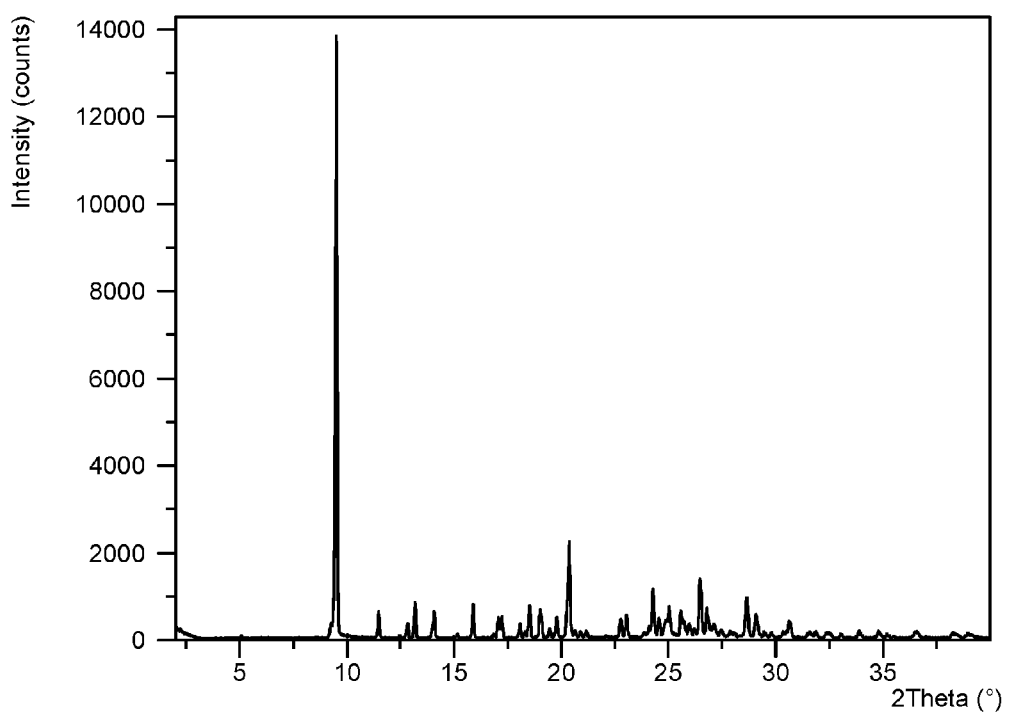
FIG. 7 shows an X-ray powder diffraction (XRPD) of Compound of formula (D) hydrate Form I.
Figure 8:
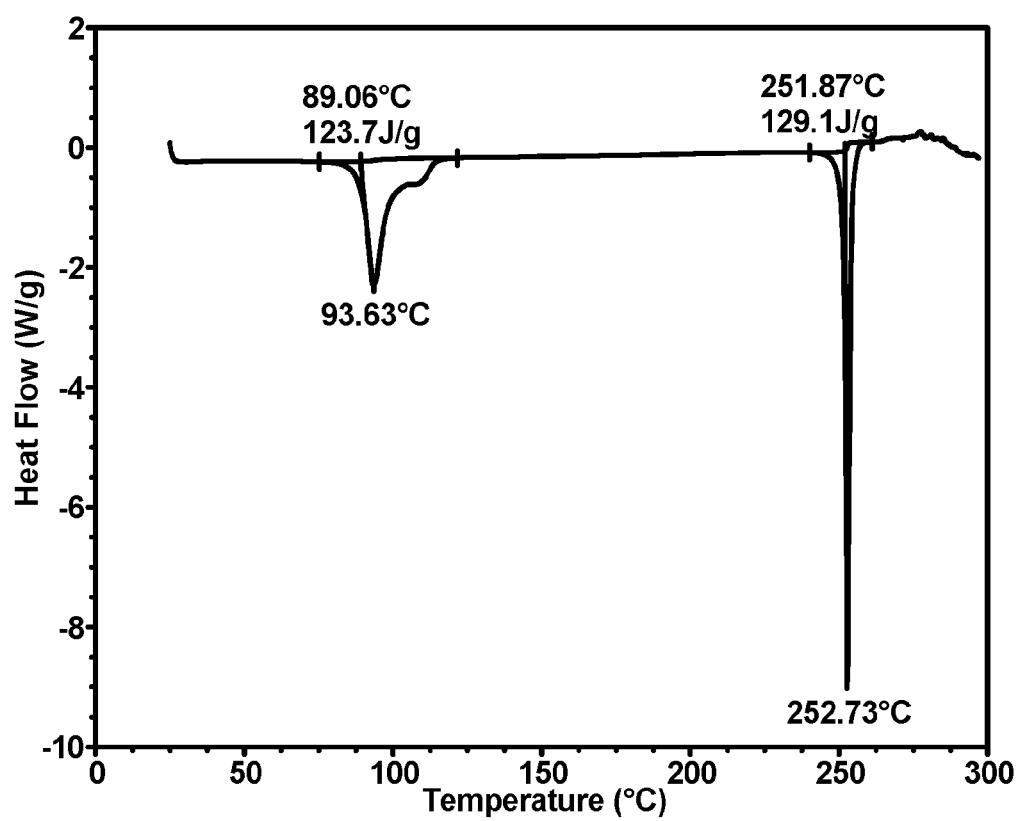
FIG. 8 shows a differential scanning calorimeter (DSC) curve of Compound of formula (D) hydrate Form I.
Figure 9:
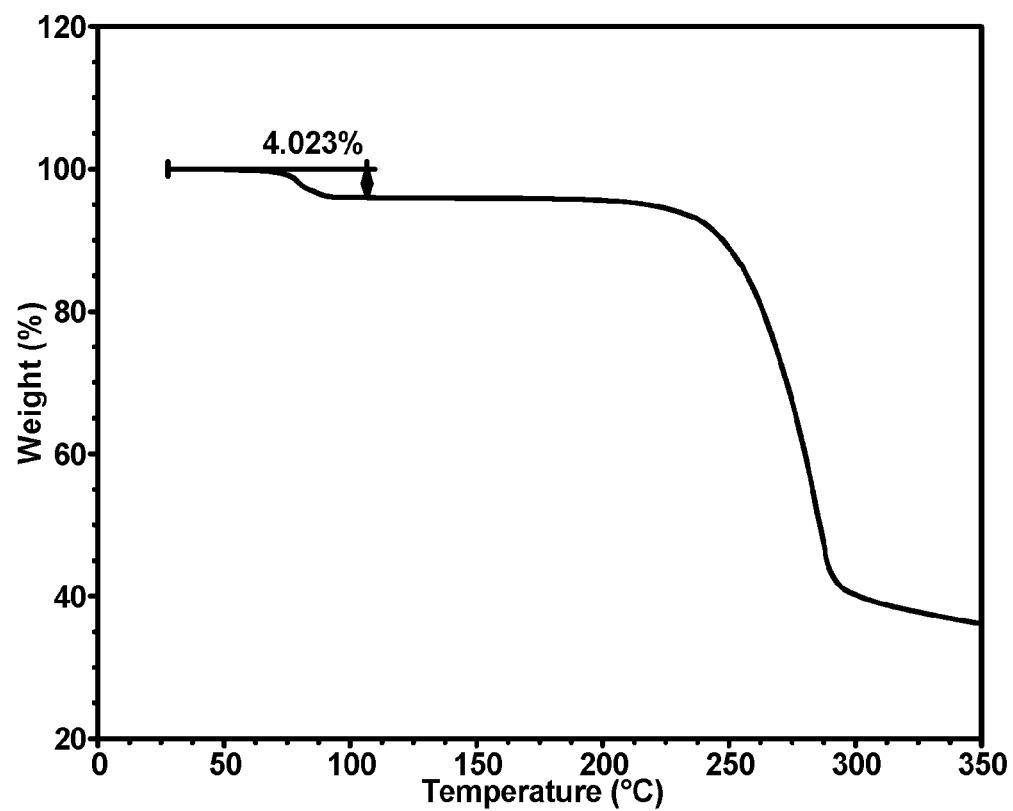
FIG. 9 shows a thermogravimetric analysis (TGA) of Compound of formula (D) hydrate Form I.

Compound of Formula (D) hydrate Form I was isolated from the current process Compound of Formula (D) zwitterion and was obtained by pH adjustment to pH about 5 in water. Initial characterization of Compound of Formula (D) hydrate Form I was performed using XRPD, DSC, TGA and KF. XRPD pattern was crystalline with some preferred orientation (FIG. 7). TGA showed about 4.0% step weight loss at about 50 to about 110° C. (FIG. 9). DSC showed broad endotherm with onset at about 89° C. corresponding to the solvent loss, followed by sharp endotherm with onset at about 252° C. (FIG. 8). KF analysis showed about 3.3% water, which corresponds to about 0.5 equivalents of water. This material was designated as Compound of Formula (D) hydrate Form I.

A stable form screen of Compound of Formula (D) hydrate Form I was performed in an attempt to determine the stability of Compound of Formula (D) hydrate Form I in different organic solvents. Table 1 summarizes the experimental details and results. Compound of Formula (D) hydrate Form I (about 50 to about 60 mg) was slurried in about 1 mL of chosen solvent. Solids were analyzed by XRPD after about 1 day and about 2 weeks of equilibration at room temperature. After about 1 day of stirring, all water miscible solvents (MeCN, MeOH, EtOH, IPA, acetone, and THF) afforded Form I. Solids in DCM were consistent with Compound of Formula (D) hydrate Form I. XRPD patterns of the solids from 2-MeTHF, EtOAc, and IPAc showed a mixture of Compound of Formula (D) Form I and Compound of Formula (D) hydrate Form I. After about 2 weeks of equilibration, Compound of Formula (D) Form I was also obtained in EtOAc and IPAc in addition to previously mentioned solvents. No from change was observed in DCM. A mixture of Compound of Formula (D) Form I and Compound of Formula (D) hydrate Form I was still observed in 2-MeTHF. These data suggest that hydrated form (Compound of Formula (D) hydrate Form I) could be easily converted to an anhydrous form (Compound of Formula (D) Form I) in water miscible solvents.

2.2 Hydrate Screen of Compound of Formula (D) Form I and of Compound of Formula (D) Form II A hydrate screen of Compound of Formula (D) was performed using a mixture of anhydrous forms of Compound of Formula (D) Form II and of Compound of Formula (D) Form I and EtOH/water solvent mixtures with different water activities (Table 1). Compound of Formula (D) Form II and Compound of Formula (D) Form I (about 20 to about 40 mg) was slurried in about 1 mL of EtOH/water or water. Samples were analyzed after about 1 day and after about 2 weeks of equilibration at room temperature. Pure anhydrous Compound of Formula (D) Form I was obtained after 1 day in mixtures with about 0.2 to about 0.4 water activity. However, after 2 weeks of equilibration a new form was obtained in EtOH/water with 0.4 water activity. This form was designated as Compound of Formula (D) Form III. Compound of Formula (D) hydrate Form I was obtained in solvents with about 0.5 to about 1.0 water activity after 1 day and after about 2 weeks.

TABLE 1

Hydrate screen of Compound of Formula (D) Form II and Compound of Formula (D) Form I.

| Water activity in EtOH/ water | water amount (mL) | EtOH amount (mL) | XRPD after 1 day (wet) | Solubility (mg/mL) | XRPD after 2 weeks (wet) |
| --- | --- | --- | --- | --- | --- |
| 0.2 | 0.031 | 0.969 | Form I | 7.27 | Form I |
| 0.3 | 0.066 | 0.934 | Form I | 8.06 | Form I |
| 0.4 | 0.077 | 0.923 | Form I | 7.86 | Form III |
| 0.5 | 0.097 | 0.903 | Hydrate Form I | 8.16 | Hydrate Form I |
| 0.6 | 0.149 | 0.851 | Hydrate Form I | 6.59 | Hydrate Form I |
| 0.7 | 0.263 | 0.737 | Hydrate Form I | 6.88 | Hydrate Form I |
| 0.8 | 0.481 | 0.519 | Hydrate Form I | 6.56 | Hydrate Form I |
| 0.9 | 0.825 | 0.175 | Hydrate Form I | 3.93 | Hydrate Form I |
| 1.0 | 1.0 | 0 | Hydrate Form I | 3.32 | Hydrate Form I |

2.3 Stable Form Screen of Compound of Formula (D) Hydrate Form I

A stable form screen of Compound of Formula (D) hydrate Form I was performed in an attempt to determine the stability of Compound of Formula (D) hydrate Form I in different organic solvents. Table 2 summarizes the experimental details and results. Compound of Formula (D) hydrate Form I (about 50 to about 60 mg) was slurried in 1 mL of chosen solvent. Solids were analyzed by XRPD after 1 day and 2 weeks of equilibration at room temperature. After 1 day of stirring, all water miscible solvents (MeCN, MeOH, EtOH, IPA, acetone, and THF) afforded Compound of Formula (D) Form I. Solids in DCM were consistent with Compound of Formula (D) hydrate Form I. XRPD patterns of the solids from 2-MeTHF, EtOAc, and IPAc showed a mixture of Compound of Formula (D) Form I and Compound of Formula (D) hydrate Form I. After about 2 weeks of equilibration, Compound of Formula (D) Form I was also obtained in EtOAc and IPAc in addition to previously mentioned solvents. No form change was observed in DCM. A mixture of Compound of Formula (D) Form I and Compound of Formula (D) hydrate Form I was still observed in 2-MeTHF. These data suggest that hydrated form (Compound of Formula (D) hydrate Form I) could be easily converted to an anhydrous form (Compound of Formula (D) Form I) in water miscible solvents.

TABLE 2

Stable form screen of Compound of Formula (D) Hydrate Form I.

| Solvent | XRPD in 1 day (wet) | Solubility (mg/mL) | XRPD in 2 weeks |
| --- | --- | --- | --- |
| MeCN | Form I | 0.40 | Form I |
| MeOH | Form I | 20.67 | Form I |
| EtOH | Form I | 6.18 | Form I |
| IPA | Form I | 2.90 | Form I |
| Acetone | Form I | 1.99 | Form I |
| DCM | Hydrate | 0.19 | Hydrate |
| THF | Form I | 11.79 | Form I |
| 2-MeTHF | Form I + Hydrate | 4.48 | Form I + Hydrate |
| EtOAc | Form I + 1 peak of Hydrate | 0.73 | Form I |
| IPAc | Form I + Hydrate | 0.45 | Form I |

2.4 Competitive Slurries of Compound of Formula (D) Form III and Form I

Three anhydrous forms of Compound of Formula (D) were observed to date: Compound of Formula (D) Form I, Compound of Formula (D) Form II, and Compound of Formula (D) Form III. Compound of Formula (D) Form II was found to be a less stable form than and Compound of Formula (D) Form I. Compound of Formula (D) Form II converted to Compound of Formula (D) Form I in EtOH/water with about 0.2 to about 0.4 water activity as was discussed above.

Compound of Formula (D) Form I, however, converted to another anhydrous form—Compound of Formula (D) Form III—in EtOH/water with 0.4 water activity after 2 weeks of equilibration. In an attempt to confirm the stability of Compound of Formula (D) Form I and Compound of Formula (D) Form III, a competitive slurry experiment was conducted using acetone as a solvent. The solids were analyzed by XRPD after 1 day and 8 days of stirring at room temperature. A mixture of forms Compound of Formula (D) Form I and Compound of Formula (D) Form III was observed after 1 day. However, full conversion of Compound of Formula (D) Form I to Compound of Formula (D) Form III was observed after 8 days suggesting that Compound of Formula (D) Form III is thermodynamically more stable form than Compound of Formula (D) Form I.

2.5 Compound of Formula (D) Form I

Figure 10:
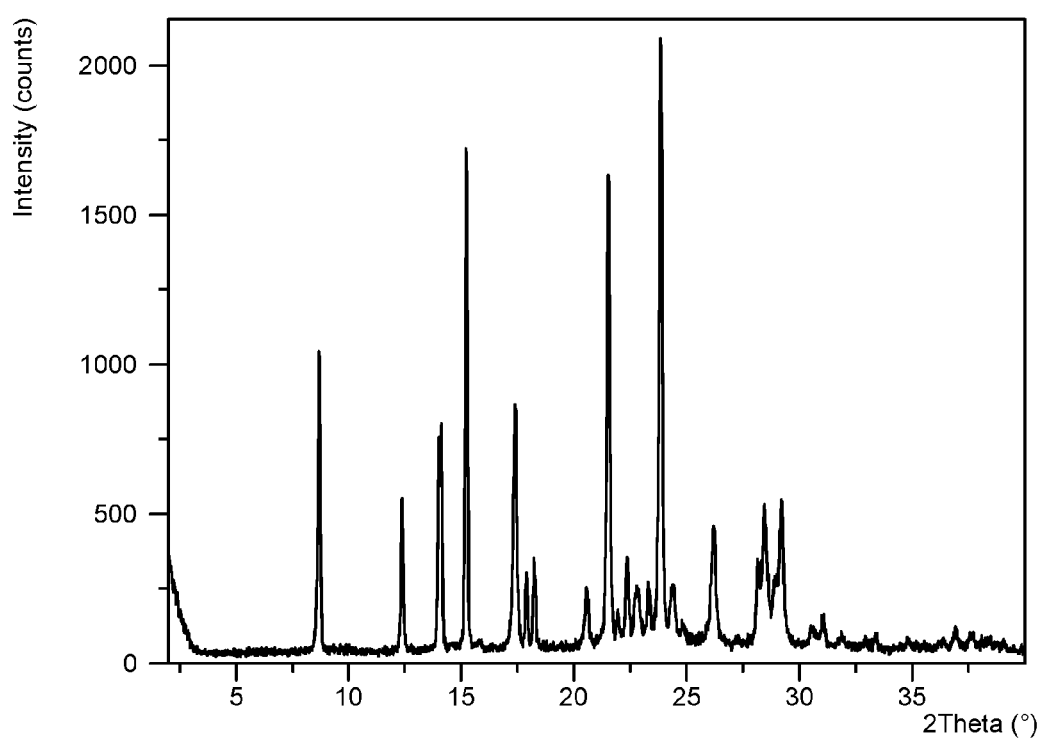
FIG. 10 shows an X-ray powder diffraction (XRPD) of Compound of formula (D) Form I.
Figure 11:
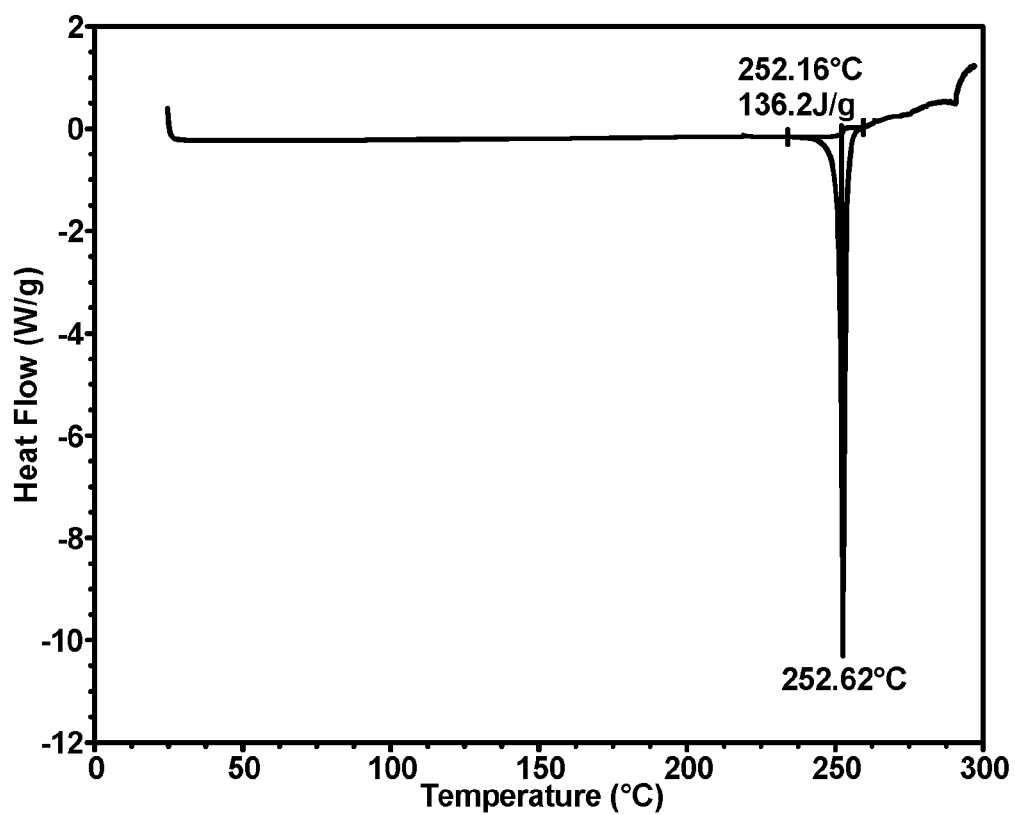
FIG. 11 shows a differential scanning calorimeter (DSC) curve of Compound of formula (D) Form I.
Figure 12:
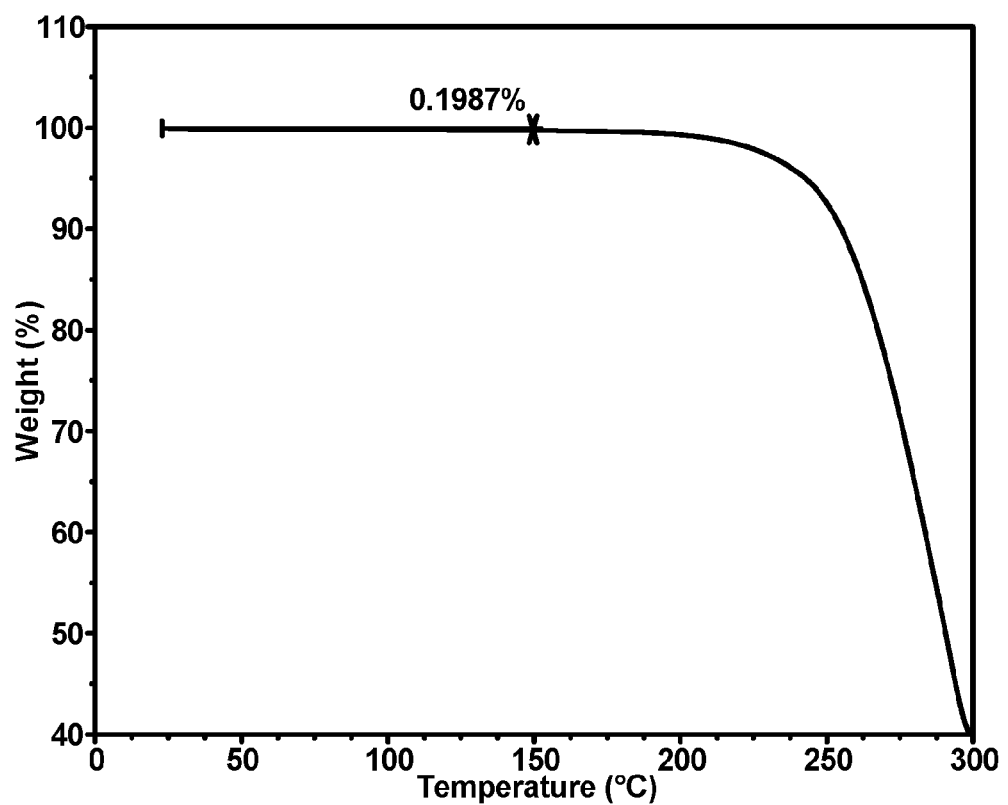
FIG. 12 shows a thermogravimetric analysis (TGA) of Compound of formula (D) Form I.

Compound of Formula (D) Form I was obtained after the isothermal hold of Compound of Formula (D) hydrate Form I at about 150° C. XRPD pattern is presented in FIG. 10. Compound of Formula (D) Form I was also obtained after KF analysis of Compound of Formula (D) Form II and Compound of Formula (D) Form I at about 180° C. Slurries of Compound of Formula (D) hydrate Form I in water miscible organic solvents also afforded Compound of Formula (D) Form I (MeCN, MeOH, EtOH, IPA, acetone, and THF). TGA showed about 0.2% continuous weight loss below about 150° C. (FIG. 10). DSC thermogram afforded single endotherm with onset at about 252° C. (FIG. 11). DVS analysis showed that Form I is slightly hygroscopic with only about 0.5% moisture uptake at 90% RH. No form change was observed after DVS.

Compound of Formula (D) Form I is a stable anhydrous form and is more stable than Compound of Formula (D) Form II. However, competitive slurries with Compound of Formula (D) Form III showed that Compound of Formula (D) Form I is less stable than Compound of Formula (D) Form III. Form I converts to Compound of Formula (D) hydrate Form I in EtOH/water at 0.5-1.0 water activity.

2.6 Compound of Formula (D) Form I and Compound of Formula (D) Form II

Figure 16:
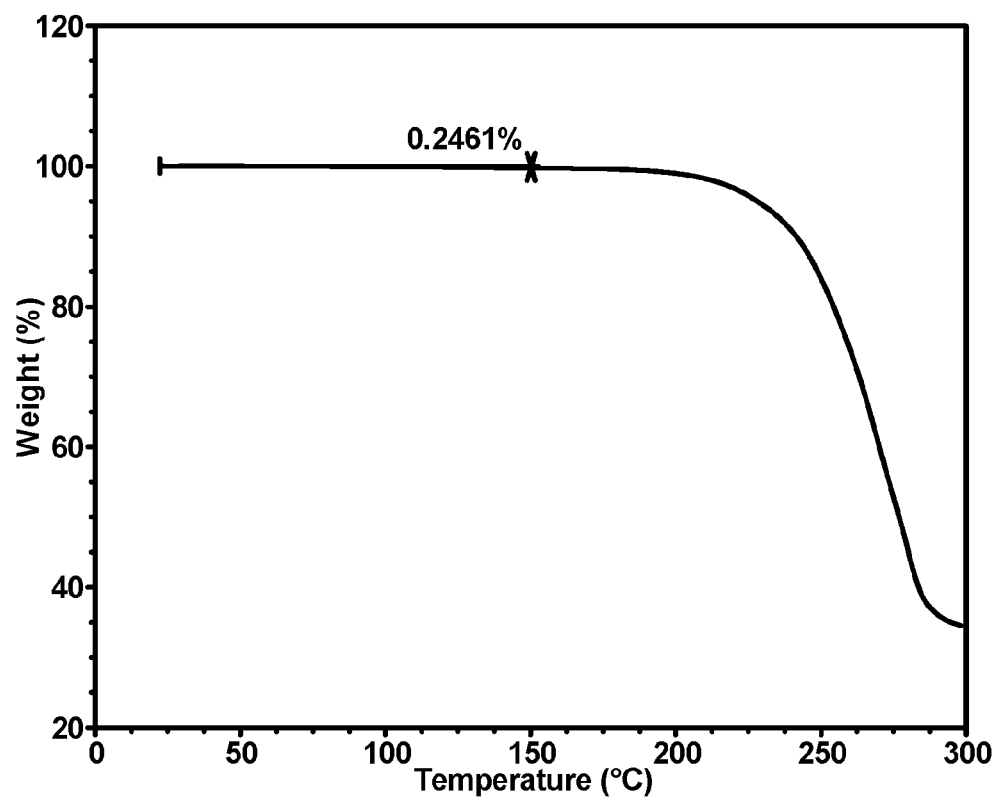
FIG. 16 shows a thermogravimetric analysis (TGA) of Compound of formula (D) Form II and Compound of formula (D) Form I.
Figure 17:
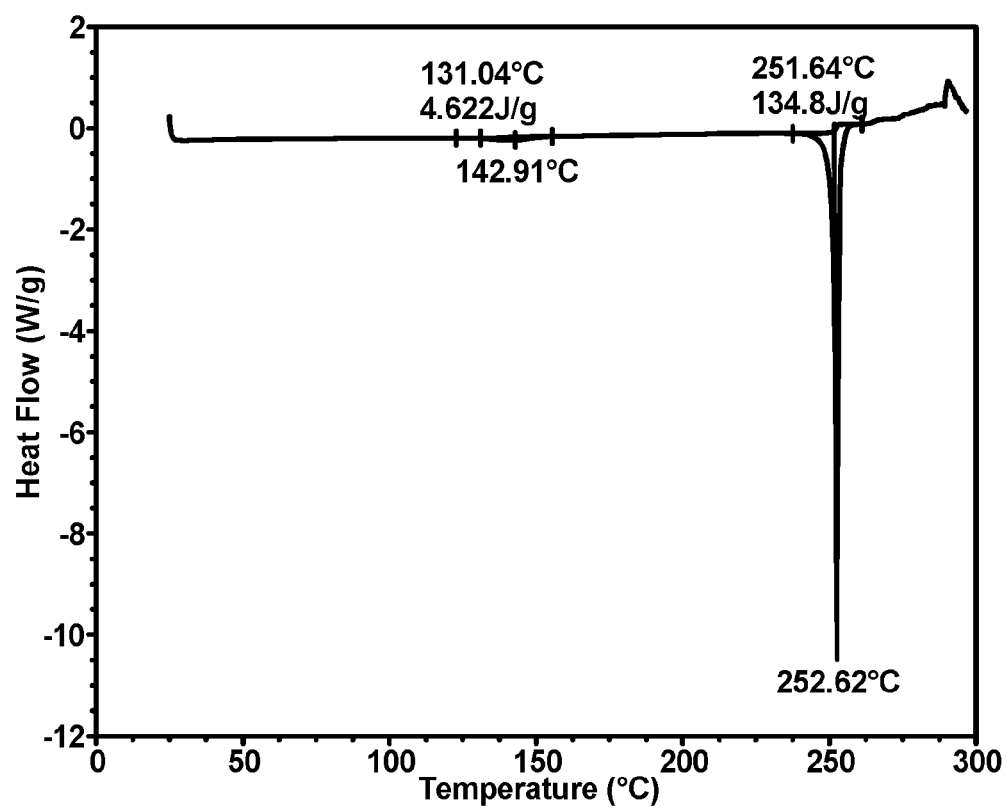
FIG. 17 shows a differential scanning calorimeter (DSC) curve of Compound of formula (D) Form II and Compound of formula (D) Form I.
Figure 18:
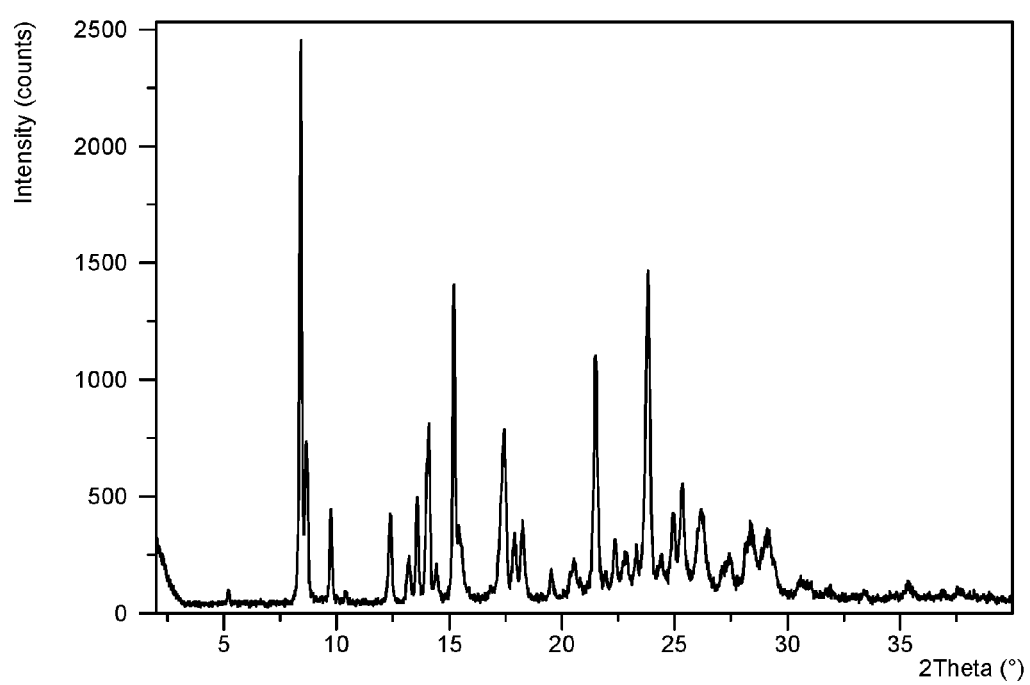
FIG. 18 shows an X-ray powder diffraction (XRPD) of Compound of formula (D) Form II and Compound of formula (D) Form I.

Compound of Formula (D) Form II was obtained in a mixture with Compound of Formula (D) Form I after vacuum drying at about 70° C. of Compound of Formula (D) hydrate Form I. XRPD pattern is presented in FIG. 18. The following characteristic peaks of compound of Formula (D) Form II were detected by subtraction of peaks of compound of Formula (D) Form I from the mixture: 5.2, 8.4, 9.8, 10.4, 13.2, 13.6, 14.4, 15.5, 19.5, 25.0, 25.4, and 27.5° 2θ±0.2° 2θ. TGA showed about 0.2% continuous weight loss below about 150° C. (FIG. 16). DSC thermogram afforded small endotherm with onset at about 131° C. most likely corresponded to the form conversion, and sharp endotherm with onset at about 252° C. (FIG. 17). KF analysis of Compound of Formula (D) Form II and Compound of Formula (D) I at about 110° C. showed 0% water. No form conversion was observed after KF at 110° C. KF analysis at about 180° C. showed 0.08% water. XRPD pattern of the solids after KF at 180° C. was consistent with Compound of Formula (D) Form I.

Compound of Formula (D) Form II is a less stable anhydrous form than Compound of Formula (D) Form I. Compound of Formula (D) Form II fully converts to Compound of Formula (D) Form I after heating to >150° C., and after the slurry in EtOH/water at 0.2-0.4 water activity. Compound of Formula (D) Form II converts to Compound of Formula (D) hydrate Form I in EtOH/water at 0.5-1.0 water activity.

2.7 Compound of Formula (D) Form III

Figure 15:
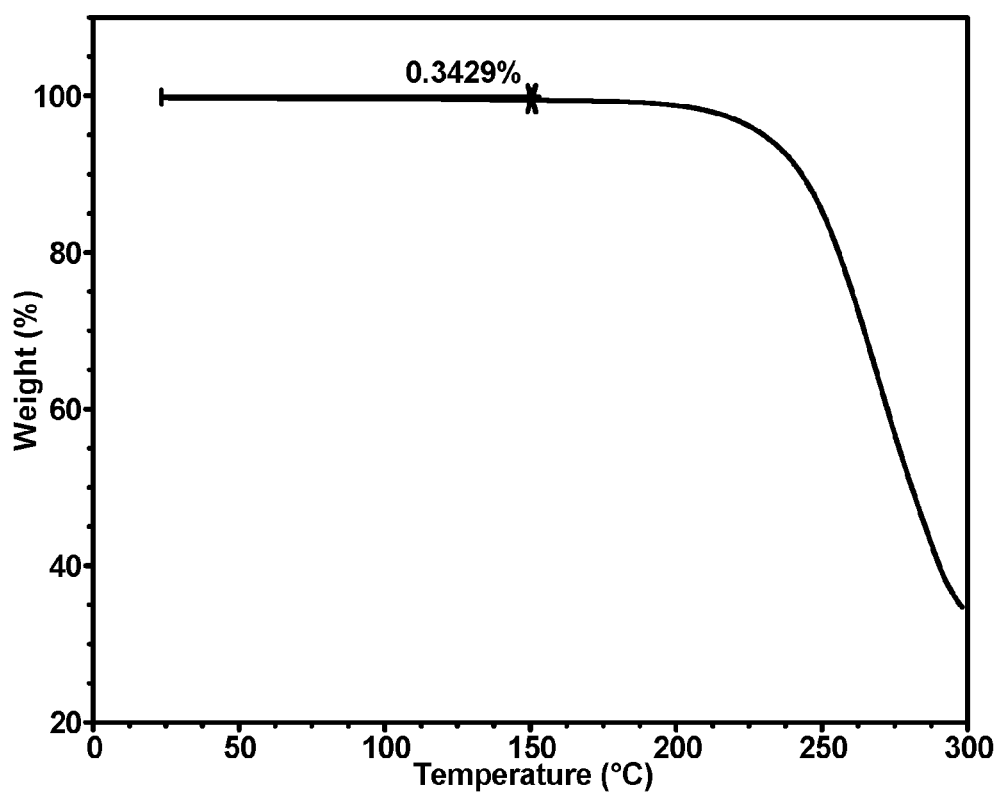
FIG. 15 shows a thermogravimetric analysis (TGA) of Compound of formula (D) Form III.

Compound of Formula (D) Form III was obtained from EtOH/water (0.4 water activity) mixture after 2 weeks slurry of Compound of Formula (D) Form II and Compound of Formula (D) Form I. XRPD pattern of Form III is presented in FIG. 13. TGA shows about 0.3% continuous weight loss below about 150° C. (FIG. 15). DSC thermogram afforded endotherm with onset at about 164° C. most likely corresponded to the form conversion, and sharp endotherm with onset at about 253° C. (FIG. 14). KF at about 110° C. showed 0% water and no form conversion. KF at about 200° C. showed 0.27% water and afforded solids with XRPD pattern consistent with Compound of Formula (D) Form I.

However, Compound of Formula (D) Form III was found to be more stable than Compound of Formula (D) Form I based on competitive slurries of Compound of Formula (D) Form I and Compound of Formula (D) Form III in acetone. Full conversion of Compound of Formula (D) Form I to Compound of Formula (D) Form III was observed after 8 days of slurry at RT. Slurry experiment showed that Compound of Formula (D) Form III converted to Compound of Formula (D) hydrate Form I in EtOH/water (0.9 water activity) overnight.

2.8 Drying Study of Compound of Formula (D) Hydrate Form I

Based on XRPD data, form conversion was observed for Compound of Formula (D) hydrate Form I after KF analysis at 110° C. The TGA drying study was performed as summarized in Table 3. The sample of Compound of Formula (D) hydrate Form I was heated up to 150° C. at 10° C./min and was held at this temperature for 10 min, followed by cooling to RT and XRPD analysis. XRPD pattern of this material was mostly consistent with XRPD pattern of the solids obtained after KF of hydrate Form I (at 110° C.) with some missing peaks, and it was designated as Compound of Formula (D) Form I.

In an attempt to scale up Compound of Formula (D) Form I, Compound of Formula (D) hydrate Form I was dried under vacuum at 70° C. for 3 days (over weekend). XRPD pattern afforded a mixture of Compound of Formula (D) Form I and Compound of Formula (D) Form II.

TABLE 3

TGA drying study of Compound of Formula (D) Hydrate Form I.

| Method | Results |
|---|---|
| 1) Heat to 150° C. at 10° C./min and hold at 150° C. for 10 min; 2) XRPD | 1) 3.9% weight loss; 2) New form by XRPD - Compound of Formula (D) Form I |

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

What is claimed is:

1. Crystalline 5-(4-cyclopropyl-1H-imidazol-1-1-2-fluoro-4-methylbenzoic acid hydrochloride (Compound of formula (D-a) Form II) characterized by an X-ray powder diffractogram comprising the following peaks: 8.7, 12.1, 25.7, and 26.3° 2θ±0.2° 2θ, as determined on a diffractometer using Cu—K☐ radiation at a wavelength of 1.5406 Å.

2. Compound of formula (D-a) Form II according to claim 1, wherein the diffractogram comprises additional peaks at 17.3, 19.0, 22.4, 28.6, and 29.7° 2θ±0.2° 2θ.

3. Compound of formula (D-a) Form II according to claim 1, wherein the diffractogram is substantially as shown in FIG. 4.

4. Compound of formula (D-a) Form II according to claim 1, characterized by a differential scanning calorimetry (DSC) curve that comprises an endotherm at about 217° C.

5. Compound of formula (D-a) Form II according to claim 1, wherein the DSC curve is substantially as shown in FIG. 5.

* * * * *

UNITED STATES PATENT AND TRADEMARK OFFICE
CERTIFICATE OF CORRECTION

PATENT NO. : 9,771,328 B2
APPLICATION NO. : 15/413154
DATED : September 26, 2017
INVENTOR(S) : Joshua R. Dunetz Page 1 of 3

It is certified that error appears in the above-identified patent and that said Letters Patent is hereby corrected as shown below:

In the Specification

In Column 13, Lines 15-16 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 13, Lines 22-23 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 13, Lines 29-30 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 13, Lines 36-37 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 13, Lines 42-43 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 13, Lines 48-49 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 54, Line 1 please replace the following text "formula (0)" with -- formula (O) --.

In Column 54, Line 39 please replace the following text "formula (0)" with -- formula (O) --.

Signed and Sealed this
Sixteenth Day of April, 2019

Andrei Iancu
*Director of the United States Patent and Trademark Office*

CERTIFICATE OF CORRECTION (continued)
U.S. Pat. No. 9,771,328 B2

In Column 59, Lines 18-19 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 59, Lines 36-37 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 59, Lines 55-56 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 60, Lines 4-6 please replace the following text "about 252° C. In some embodiments, the DSC curve further comprises an endotherm at about 89° C." with -- about 252 °C. In some embodiments, the DSC curve further comprises an endotherm at about 89 °C. --.

In Column 60, Lines 10-12 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 60, Line 25 please replace the following text "252° C." with -- 252 °C. --.

In Column 60, Lines 28-29 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 60, Lines 45-47 please replace the following text "about 252° C. In some embodiments, the DSC curve further comprises an endotherm at about 131° C." with -- about 252 °C. In some embodiments, the DSC curve further comprises an endotherm at about 131 °C. --.

In Column 60, Lines 51-52 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Column 60, Lines 66-67 please replace the following text "about 253° C. In some embodiments, the DSC curve further comprises an endotherm at about 164° C." with -- about 253 °C. In some embodiments, the DSC curve further comprises an endotherm at about 164 °C. --.

In Column 62, Line 59 please replace the following text "75 to 80° C." with -- 75 to 80 °C. --.

In Column 63, Line 44 please replace the following text "100° C." with -- 100 °C. --.

In Column 63, Line 59 please replace the following text "100° C." with -- 100 °C. --.

In Column 70, Line 28 please replace the following text "45° C." with -- 45 °C. --.

CERTIFICATE OF CORRECTION (continued)
U.S. Pat. No. 9,771,328 B2

In Column 70, Line 31 please replace the following text "45° C." with -- 45 °C. --.

In Column 84, Line 17 please replace the following text "100° C." with -- 100 °C. --.

In Column 90, Line 9 please replace the following text "110° C." with -- 110 °C. --.

In the Claims

In Claim 1, Column 90, Lines 48-49 please replace the following text "5-(4-cyclopropyl-1H-imidazol-1-1-2-fluoro-4-methylbenzoic acid" with -- 5-(4-cyclopropyl-1H-imidazol-1-yl)-2-fluoro-4-methylbenzoic acid --.

In Claim 1, Column 90, Line 53 please replace the following text "Cu - K☐" with -- Cu-Kα --.

In Claim 4, Column 90, Line 62 please replace the following text "217° C." with -- 217 °C. --.